(12) United States Patent
Rothstein et al.

(10) Patent No.: US 6,808,893 B1
(45) Date of Patent: Oct. 26, 2004

(54) GLUTAMATE TRANSPORTER ASSOCIATED PROTEINS AND METHODS OF USE THEREOF

(75) Inventors: Jeffrey D. Rothstein, Catonsville, MD (US); Mandy Jackson, Baltimore, MD (US); Glen Lin, Columbus, OH (US); Robert Law, Owings Mills, MD (US); Irina Orlov, Baltimore, MD (US)

(73) Assignee: The Johns Hopkins University School of Medicine, Baltimore, MD (US)

( * ) Notice: Subject to any disclaimer, the term of this patent is extended or adjusted under 35 U.S.C. 154(b) by 260 days.

(21) Appl. No.: 09/695,795

(22) Filed: Oct. 23, 2000

Related U.S. Application Data

(60) Provisional application No. 60/161,007, filed on Oct. 23, 1999, and provisional application No. 60/206,157, filed on May 22, 2000.

(51) Int. Cl.[7] .................. C12N 15/00; C12N 15/63; C12N 15/85; C12N 15/86; C07N 21/04

(52) U.S. Cl. .................. 435/69.1; 435/320.1; 435/325; 536/23.1; 536/23.5; 530/350

(58) Field of Search ................. 536/23.1, 23.5; 435/325, 69.1, 320.1; 530/350

(56) References Cited

PUBLICATIONS

Skolnick et al., 2000, Trends in Biotech. 18:34–39.*
Bork, P., 2000, Genome Research 10:398–400.*
Doerks et al., 1998, Trends in Genetics 14:248–250.*
Smith et al., 1997, Nature Biotechnology 15:1222–1223.*
Brenner, S., 1999, Trends in Genetics 15:132–133.*
Bork, P., 1996, Trends in Genetics 12:425–427.*
Pilbeam et al., 1993, Bone 14: 717–720.*
Katan and Allen, 1999, FEBS Letters, 452: 36–40.*
Levine, H 3rd, 1999, Mol. Neurobiol., 19(2): 111–149.*
Katan, et al, 1999, FEBS Letters 452:36–40.*

* cited by examiner

*Primary Examiner*—Gary Kunz
*Assistant Examiner*—Sandra Wegert
(74) *Attorney, Agent, or Firm*—Gray Cary Ware & Freidenrich, LLP

(57) ABSTRACT

Glutamate Transporter Associated Proteins and nucleotide encoding Glutamate Transporter Associated Proteins are provided. Also provided is a method for identifying a compound that modulates a cellular response mediated by a Glutamate Transporter Associated Protein. A method is further provided for identifying a compound that inhibits an interaction between a Glutamate Transporter Associated Protein and a glutamate transporter protein. A method is provided for treating a disorder associated with glutamate transport.

8 Claims, 26 Drawing Sheets

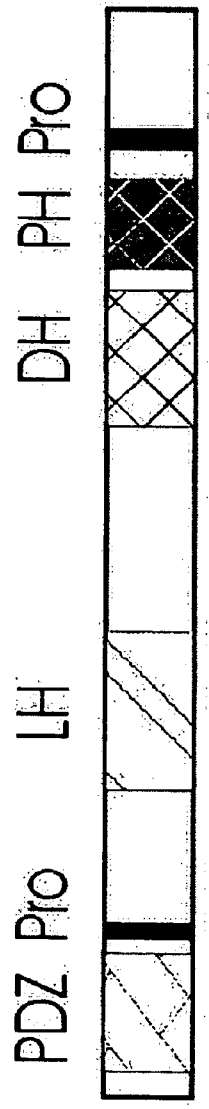
FIGURE 1A
FIGURE 1B

Retinoic Acid Treatment (picomol/μL/hr)

FIGURE 14A

ATGAGCAGCACCCTGTCACCCACTGACTTCGACAGCTTGGAGATCCAGGGCCAGTACAGTGA
CATCAACAACCGCTGGGACCTGCCCGACTCAGATTGGGACAATGACAGCAGTTCAGCCCGCC
TCTTTGAGAGGTCCAGAATTAAGGCCCTGGCAGATGAGCGAGAAGCCGTGCAGAAGAAAACC
TTCACCAAGTGGGTGAACTCCCACCTGGCCCGGGTGACATGCCGGGTGGGAGACCTGTACAG
CGACCTGCGGGACGGGCGCAACCTCCTGAGGCTCCTGGAGGTGCTCTCGGGAGAGACCCTGC
CAAAACCCACCAAGGGCCGGATGCGGATTCACTGCCTGGAGAATGTCGACAAAGCACTGCAG
TTCCTGAAGGAGCAGAAGGTGCACCTGGAAAACATGGGCTCCCACGACATTGTGGATGGGAA
CCACCGTCTGACCCTTGGGCTAGTGTGGACCATCATCCTCCGATTTCAGATCCAAGACATCA
GTGTGGAGACAGAAGACAACAAGGAGAAGAAGTCAGCCAAGGATGCCCTGCTGCTGTGGTGC
CAGATGAAGACTGCAGGGTATCCCAATGTCAATGTGCACAACTTTACCACCAGTTGGAGAGA
TGGGCTGGCCTTTAATGCCATTGTGCACAAACACCGGCCAGACCTGTTGGATTTTGAGTCCC
TGAAGAAGTGTAACGCACACTACAATCTGCAGAATGCTTTCAATCTGGCTGAAAAGGAACTT
GGCCTGACGAAGCTCCTGGATCCTGAAGATGTGAACGTAGACCAACCCGATGAGAAGTCCAT
CATCACCTACGTGGCCACTTACTACCACTACTTCTCGAAGATGAAGGCCCTGGCTGTGGAAG
GCAAAGGATTGGCAAGGTCCTGGACCATGCCATGGAGGCAGAACACCTGGTAGAGAAATAT
GAGTCCCTGGCCTCTGAACTGCTGCAGTGGATCGAGCAAACGATTGGGACCTTCAATGACCG
ACAGCTGGCCAACTCCCTGAGTGGCGTCCAGAACCAGCTGCAGTCTTTCAATTCCTACCGCA
CGGTGGAGAAGCCACCCAAGTTCACAGAGAAAGGGAACTTGGAGGTGTTGCTCTTCACCATC
CAGAGTAAGCTGCGGGCCAACAACCAGAAAGTCTACACACCACGCGAAGGCCGGCTCATCTC
GGACATCAACAAGGCCTGGGAGCGGCTAGAGAAAGCCGAACATGAGCGAGAGCTGGCCCTGC
GCACGGAGCTGATCCGCCAGGAGAAGCTGGAGCAACTGGCTGCTCGCTTCGACCGCAAGGCT
GCCATGCGGGAGACCTGGCTCAGTGAGAACCAGCGCCTCGTCTCCCAGGACAACTTTGGCCT
GGAGCTGGCAGCAGTGGAGGCAGCAGTGCGGAAGCATGAAGCCATTGAGACAGACATTGTGG
CCTACAGCGGCCGGGTGCAAGCGGTGGACGCCGTAGCCGCAGAACTGGCCGCTGAGCATTAC
CATGACATTAAGCGCATTGCGGCGCGGCAGAACAACGTGGCCCGGCTCTGGGACTTCTTACG
AGAGATGGTGGCCGCCCGCCGTGAGCGGCTCCTTCTCAACCTGGAGCTGCAGAAGGTGTTTC
AGGACCTGCTCTACCTCATGGACTGGATGGCAGAGATGAAGGGCCGGCTGCAGTCTCAGGAC
CTAGGCAAGCATCTGGCTGGAGTGGAAGATCTACTGCAACTACACGAACTGGTGGAGGCGGA
CATTGCAGTTCAGGCTGAGAGGGTGCGAGCGGTCAGCGCCTCTGCCCTGCGCTTCTGCGACC
CAGGGAAAGAGTATAGACCTTGCGGCCCGCAGCTAGTGTCAGAGAGGGTAGCCACTCTGGAG
CAGAGCTATGAGGCCCTGTGCGAATTGGCAGCAACTCGAAGGGCCCGACTGGAAGAGTCCCG
TCGTCTCTGGAGGTTCCTCTGGGAAGTGGGTGAGGCCGAGGCCTGGGTTCGGGAGCAGCAGC
ACCTCCTGGCCTCAGCTGAGACAGGCCGGGACCTGACTGGTGTCCTCCGCCTGCTCAATAAG
CACACAGCCCTACGGGGTGAGATGAGTGGCCGCCTGGGGCCCCTGAAGCTCACCCTGGAACA
AGGTCAGCAGTTAGTTGCCGAGGGCCACCCTGGAGCTAACCAAGCCTCAACCCGTGCAGCAG
AGCTCCAGGCCCAGTGGGAGCGACTAGAAGCCCTGGCCGAGGAGCGAGCCCAGCGGCTAGCA
CAGGCTGCCAGCCTCTACCAGTTCCAGGCAGATGCCAATGACATGGAGGCTTGGTTGGTGGA
CGCACTACGCCTGGTATCTAGCCCTGAGGTAGGGCACGATGAGTTCTCCACGCAGGCCCTGG
CCAGGCAGCACAGGGCCCTTGAGGAGGAGATCCGAGCCCACCGGCCTACACTGGATGCCTTG
AGGGAGCAGGCTGCAGCCCTGCCACCTGCACTGAGCCACACACCTGAGGTACAGGGCAGGGT
GCCCACTCTGGAGCAGCACTATGAGGAGCTGCAGGCCCGGGCAGGTGAGCGTGCACGAGCCC
TGGAAGCAGCCCTGGCGTTCTATACCATGCTCAGCGAGGCCGGGGCTTGTGGGCTCTGGGTA
GAGGAGAAGGAGCAGTGGCTCAACGGGCTGGCCCTACCTGAGCGCCTGGAGGACCCGGAGGT
GGTCCAACAGAGGTTTGAGACCTTAGAGCCCGAAATGAACGCCCTGGCTGCACGGATTACTG
CTGTCAGTGACATAGCTGAGCAGTTGCTGAAGGCCAGTCCACCAGGCAAGGACCGCATCATT
GGCACCCAGGAGCAGCTCAACCAAAGGTGGCAGCAGTTCAGGTCCCTGGCAGGTGGCAAAAA
GGCAGCTCTGACATCAGCCCTGAGCATCCAGAATTACCACCTAGAGTGCACAGAGACCCAGG
CCTGGATGAGAGAAAAGACCAAGGTCATTGAGTCTACCCAGGACCTAGGCAATGATCTAGCT

FIGURE 14B

```
GGTGTGCTGGCCCTGCAGCGGAAGCTGGCAGGCACTGAGAGAGATCTGGAAGCCATCTCTGC
CCGGGTGGGTGAGCTGACCCAAGAGGCAAATGCTTTGGCTGCTGGGCACCCAGCCCAAGCCC
CTGCCATCAACACACGGCTTGGAGAGGTTCAAACTGGATGGGAGGATCTTCGGGCAACCATG
AGGCGGAGAGAAGAGTCCCTGGGTGAGGCTCGACGGCTGCAAGATTTCCTGCGCAGCTTAGA
TGACTTCCAGGCCTGGCTAGGCCGCACACAGACTGCTGTAGCCTCTGAGGAAGGACCAGCCA
CCCTTCCAGAGGCAGAAGCCCTCTTAGCCCAGCATGCAGCTCTGCGGGGAGAGGTGGAGAGA
GCCCAGAGCGAGTACAGCCGCCTCAGGACCTTGGGCGAGGAGGTGACCAGAGACCAGGCTGA
TCCCCAATGCCTCTTCCTCAGACAGAGGCTGGAAGCCCTTGGAACCGGCTGGGAGGAGCTGG
GTCGCATGTGGGAGAGCCGGCAAGGCCGCTTGGCCCAAGCCCATGGCTTCCAGGGGTTTTTG
AGAGATGCTCGCCAGGCTGAGGGAGTTCTCAGCAGCCAGGAATATGTTCTGTCTCACACGGA
GATGCCAGGGACACTGCAGGCGGCGGATGCAGCCATTAAAAGCTGGAAGACTTCATGAGCA
CCATGGACGCCAATGGAGAGCGCATCCGTGGACTCCTGGAGGCTGGCCGTCAGCTGGTGTCC
AAGGGCAATATCCATGCTGAGAAGATCCAAGAGAAGGCAGACTCCATCGAGAAGAGGCACAG
AAAGAACCAGGAGGCCGTGCAGCAGCTTCTAGGCCGCCTTCGGGACAACCGAGAGCAGCAGC
ACTTCTTGCAAGACTGTCAGGAGCTGAAACTCTGGATTGACGAGAAGATGCTGACAGCTCAG
GATGTGTCCTATGATGAGGCACGCAACCTGCACACCAAGTGGCAAAAACACCAGGCATTCAT
GGCCGAGCTGGCAGCCAACAAGGACTGGCTGGACAAAGTGGACAAGGAAGGGCGGGAGCTGA
CTCTTGAAAAGCCAGAACTCAAAGTCCTAGTGTCAGAGAAGCTGGAGGACCTGCACAGGCGC
TGGGATGAACTGGAGACTACCACCCAAGCCAAGGCCCGCAGTCTTTTTGATGCTAACCGGGC
AGAGCTATTTGCCCAAAGCTGTTCTGCCCTGGAGAGCTGGCTGGAGAGCCTGCAGGCCCAGC
TGCACTCAGATGACTATGGCAAGGACCTCACCAGTGTCAACATTCTGCTAAAGAAGCAACAG
ATGCTGGAACGAGAGATGGCTGTGAGAGAGAAGGAGGTAGAGGCTATCCAGGCCCAGGCAAA
AGCCCTGGCCCAGGAAGACCAAAGTGCAGGAGAGGTGGAAAGGACCTCCAGAGCTGTGGAGG
AGAAGTTCAGGGCCTTGTGTCAGCCCATGAAGGACCGCTGCCGGCGCCTGCAAGCCTCCCGA
GAGCAGCACCAGTTCCACCGGGATGTGGAGGATGAGATACTGTGGGTGACCGAGCGGCTTCC
CATGGCCAGCTCTCTGGAGCATGGCAAGGACTTGCCCAGCGTCCAGCTTCTCATGAAGAAAA
ACCAGACTCTGCAGAAGGAGATCCAGGGCCATGAGCCCCGGATTGCAGACCTCAAAGAGAGG
CAGCGCACTCTGAGAACAGCAGCAGCGGGTCCAGAGCTGGCTGAGCTCCAGGAAATGTGGAA
ACGCCTGAGCCATGAGCTGGAGCTTCGGGGTAAACGACTGGAGGAGGCCCTTCGAGCCCAGC
AATTCTATCGTGACGCTGCAGAGGCCGAGGCTTGGATGGGGGAGCAGGAGTTACATATGATG
GGCCAGGAAAAGGCCAAGGATGAGCTGAGCGCCCAGGCAGAAGTGAAGAAGCATCAGGTACT
AGAACAAGCCCTTGCTGACTATGCCCAGACCATCAAACAACTAGCAGCCAGCAGTCAAGATA
TGATTGACCATGAACATCCAGAGAGCACAAGGTTAACAATACGCCAAGCCCAGGTGGACAAG
CTGTACGCCGGCCTAAAGGAGCTGGCAGGAGAGCGGCGTGAGCGTCTGCAGGAGCACCTCAG
GCTGTGCCAGCTCCGCAGAGAGCTGGATGACCTGGAGCAGTGGATACAGGAGCGAGAAGTCG
TGGCAGCCTCCCATGAACTGGGCCAGGACTATGAGCATGTGACTATGCTTCGGGACAAATTC
CGAGAGTTCTCCAGGGACACCAGCACCATTGGCCAAGAGCGTGTAGACAGTGCCAATGCCCT
GGCCAATGGGCTCATTGCTGGGGGCCATGCTGCATGGGCCACCGTGGCCGAGTGGAAGGACA
GTCTCAATGAGGCCTGGGCTGACCTGCTGGAGCTGCTGGACACAAGAGGTCAGGTGCTGGCT
GCTGCTTATGAGCTGCAGCGCTTCCTGCATGGGGCCCGCCAAGCCCTGGCACGGGTGCAGCA
CAAGCAGCAGCAGCTTCCAGATGGGACGGGCCGCGACCTCAATGCTGCTGAGGCCCTGCAGC
GCCGGCACTGCGCCTATGAGCACGACATCCAAGCCCTCAGCACTCAGGTCCAGCAGGTTCAG
GACGATGGCCTCAGGCTACAAAAGGCCTATGCTGGAGACAAGGCTGAGGAAATTGGCCGTCA
CATGCAGGCAGTGGCTGAGGCGTGGGCCCAGCTCCAGGGAAGTTCTGCTGCCCGTCGCCAGC
TGTTACTGGATACCACAGACAAATTCCGATTCTTCAAGGCTGTCCGGGAGTTGATGCTGTGG
ATGGATGGGATTAACCTGCAGATGGATGCCCAGGAGAGGCCCCGGGATGTGTCCTCTGCAGA
TTTAGTCATCAAAAACCAACAAGGCATCAAAGCAGAGATAGAGGCAAGAGCTGACAGGTTCT
CCGCCTGCATTGACATGGGGCAAGAGCTGCTGGCCCGGAACCACTATGCCGCTGAGGAGATC
```

FIGURE 14C

```
TCAGAGAAGCTGTCTCAGCTACAGTCCCGGCGCCAGGAGACAGCTGAAAAGTGGCAGGAGAA
GATGGACTGGCTACAGCTTGTTTTGGAGGTGCTTGTGTTTGGGAGAGATGCAGGCATGGCAG
AGGCCTGGCTATGCAGTCAGGAGCCATTGGTGCGAAGTGCAGAACTGGGTTGCACTGTGGAT
GAAGTAGAGAGCCTCATCAAGCGGCATGAAGCCTTCCAGAAGTCAGCAGTGGCCTGGGAGGA
GCGTTTCAGTGCCCTGGAGAAGCTCACTGCGCTGGAAGAGCGGGAGAATGAGCAGAAAAGGA
AGAGGGAGGAGGAGGAACGAAGGAAACAGCCCCCTACTTCAGAGCCCATGGCTAGTCAACCG
GAAGGGAGTCTGGTAGATGGCCAGAGAGTTCTTGACACTGCCTGGGATGGGACCCAGTCAAA
ATTGCCACCATCCACACAAGCACCCAGCATTAATGGGGTCTGCACGGACACGGAGTCCTCAC
AGCCTCTGTTGGAACAGCAAAGACTTGAACAGAGCAATGTCCCAGAAGGGCCTGGATCTGGC
ACAGGAGACGAGTCCAGCGGGCCCCGGGGAGAGAGGCAGACCCTGCCCCGGGGCCCTGCTCC
GTCTCCAATGCCCCAGAGCAGATCGTCTGAGTCAGCTCATGTTGCCACCCTGCCCGCACGAG
GTGCTGAGCTCTCTGCTCAGGAACAGATGGAAGGGACGCTGTGCCGCAAACAGGAGATGGAA
GCCTTCAATAAGAAAGCTGCCAACAGGTCCTGGCAGAATGTGTACTGTGTACTTCGGCGTGG
AAGCCTCGGCTTTTACAAGGATGCCAGGGCAGCTAGTGCAGGAGTGCCATACCATGGAGAAG
TGCCTGTCAGTCTGGCCAGGGCCCAGGGCAGTGTGGCCTTTGATTATCGGAAACGCAAACAT
GTCTTCAAGCTGGGCTTGCAGGATGGGAAAGAGTATCTATTCCAGGCCAAGGATGAGGCAGA
GATGAGCTCATGGCTGAGAGTGGTGAATGCAGCCATTGCCACTGCGTCCTCGGCCTCTGGAG
AGCCAGAAGAGCCAGTGGTGCCCAGTGCCAGCCGGGGTCTGACCAGGGCCATGACCATGCCC
CCAGTGTCACAGCCTGAGGGCTCCATCGTGCTTCGCAGCAAGGATGGCAGAGAAAGAGAGCG
AGAAAAACGATTCAGCTTCTTTAAGAAGAACAAGTAGTTGGGGCAAGACTCCCAGGCCAGCT
CCCTCCCTCTGTTCAGGAAACTGCCAGGGACTGTCGACAGAGACCACC
```

FIGURE 15

MSSTLSPTDFDSLEIQGQYSDINNRWDLPDSDWDNDSSSARLFERSRIKALADEREA
VQKKTFTKWVNSHLARVTCRVGDLYSDLRDGRNLLRLLEVLSGETLPKPTKGRMRIHCLENV
DKALQFLKEQKVHLENMGSHDIVDGNHRLTLGLVWTIILRFQIQDISVETEDNKEKKSAKDA
LLLWCQMKTAGYPNVNVHNFTTSWRDGLAFNAIVHKHRPDLLDFESLKKCNAHYNLQNAFNL
AEKELGLTKLLDPEDVNVDQPDEKSIITYVATYYHYFSKMKALAVEGKRIGKVLDHAMEAEH
LVEKYESLASELLQWIEQTIGTFNDRQLANSLSGVQNQLQSFNSYRTVEKPPKFTEKGNLEV
LLFTIQSKLRANNQKVYTPREGRLISDINKAWERLEKAEHERELALRTELIRQEKLEQLAAR
FDRKAAMRETWLSENQRLVSQDNFGLELAAVEAAVRKHEAIETDIVAYSGRVQAVDAVAAEL
AAEHYHDIKRIAARQNNVARLWDFLREMVAARRERLLLNLELQKVFQDLLYLMDWMAEMKGR
LQSQDLGKHLAGVEDLLQLHELVEADIAVQAERVRAVSASALRFCDPGKEYRPCGPQLVSER
VATLEQSYEALCELAATRRARLEESRRLWRFLWEVGEAEAWVREQQHLLASAETGRDLTGVL
RLLNKHTALRGEMSGRLGPLKLTLEQGQQLVAEGHPGANQASTRAAELQAQWERLEALAEER
AQRLAQAASLYQFQADANDMEAWLVDALRLVSSPEVGHDEFSTQALARQHRALEEEIRAHRP
TLDALREQAAALPPALSHTPEVQGRVPTLEQHYEELQARAGERARALEAALAFYTMLSEAGA
CGLWVEEKEQWLNGLALPERLEDPEVVQQRFETLEPEMNALAARITAVSDIAEQLLKASPPG
KDRIIGTQEQLNQRWQQFRSLAGGKKAALTSALSIQNYHLECTETQAWMREKTKVIESTQDL
GNDLAGVLALQRKLAGTERDLEAISARVGELTQEANALAAGHPAQAPAINTRLGEVQTGWED
LRATMRRREESLGEARRLQDFLRSLDDFQAWLGRTQTAVASEEGPATLPEAEALLAQHAALR
GEVERAQSEYSRLRTLGEEVTRDQADPQCLFLRQRLEALGTGWEELGRMWESRQGRLAQAHG
FQGFLRDARQAEGVLSSQEYVLSHTEMPGTLQAADAAIKKLEDFMSTMDANGERIRGLLEAG
RQLVSKGNIHAEKIQEKADSIEKRHRKNQEAVQQLLGRLRDNREQQHFLQDCQELKLWIDEK
MLTAQDVSYDEARNLHTKWQKHQAFMAELAANKDWLDKVDKEGRELTLEKPELKVLVSEKLE
DLHRRWDELETTTQAKARSLFDANRAELFAQSCSALESWLESLQAQLHSDDYGKDLTSVNIL
LKKQQMLEREMAVREKEVEAIQAQAKALAQEDQSAGEVERTSRAVEEKFRALCQPMKDRCRR
LQASREQHQFHRDVEDEILWVTERLPMASSLEHGKDLPSVQLLMKKNQTLQKEIQGHEPRIA
DLKERQRTLRTAAAGPELAELQEMWKRLSHELELRGKRLEEALRAQQFYRDAAEAEAWMGEQ
ELHMMGQEKAKDELSAQAEVKKHQVLEQALADYAQTIKQLAASSQDMIDHEHPESTRLTIRQ
AQVDKLYAGLKELAGERRERLQEHLRLCQLRRELDDLEQWIQEREVVAASHELGQDYEHVTM
LRDKFREFSRDTSTIGQERVDSANALANGLIAGGHAAWATVAEWKDSLNEAWADLLELLDTR
GQVLAAAYELQRFLHGARQALARVQHKQQQLPDGTGRDLNAAEALQRRHCAYEHDIQALSTQ
VQQVQDDGLRLQKAYAGDKAEEIGRHMQAVAEAWAQLQGSSAARRQLLLDTTDKFRFFKAVR
ELMLWMDGINLQMDAQERPRDVSSADLVIKNQQGIKAEIEARADRFSACIDMGQELLARNHY
AAEEISEKLSQLQSRRQETAEKWQEKMDWLQLVLEVLVFGRDAGMAEAWLCSQEPLVRSAEL
GCTVDEVSLIKRHEAFQKSAVAWEERFSALEKLTALEERENEQKRKREEEERRKQPPTSEPM
ASQPEGSLVDGQRVLDTAWDGTQSKLPPSTQAPSINGVCTDTESSQPLLEQQRLEQSNVPEG
PGSGTGDESSGPRGERQTLPRGPAPSPMPQSRSSESAHVATLPARGAELSAQEQMEGTLCRK
QEMEAFNKKAANRSWQNVYCVLRRGSLGFYKDARAASAGVPYHGEVPVSLARAQGSVAFDYR
KRKHVFKLGLQDGKEYLFQAKDEAEMSSWLRVVNAAIATASSASGEPEEPVVPSASRGLTRA
MTMPPVSQPEGSIVLRSKDGREREREKRFSFFKKNK.

FIGURE 16A

```
ATGAGCATACGATTGCCCCATAGTATAGACAGATCAGCCAGTAAAAAGCAGTCTCAC
CTGTCCAGTCCCATTGCATCCTGGTTAAGTAGCCTGTCTTCTCTGGGAGATTCTACA
CCTGAACGCACATCCCCTTCTCACCACCGCCAGCCCTCTGACACTTCTGAGACAACA
GCAGGTCTTGTTCAGCGCTGTGTCATCATCCAAAAGGACCAGCATGGCTTTGGCTTC
ACAGTTAGTGGAGATCGCATTGTACTGGTGCAGTCCGTGCGCCCTGGAGGCGCAGCC
ATGAAAGCTGGTGTGAAAGAGGGTGACCGGATCATCAAAGTAAACGGCACCATGGTG
ACCAATAGCTCACACCTGGAGGTGGTAAAGCTTATCAAATCGGCGCCTATGCTGCG
CTTACCCTCCTAGGCTCTTCTCCTCCCTCCGTCGGCGTCTCTGGGCTCCAGCAGAAT
CCATCTGTGGCAGGAGTGCTCAGAGTTAACCCCATCATTCCTCCACCACCTCCCCCG
CCACCCTTGCCACCTCCACAGCACATTACTGGACCCAAACCTCTTCAGGATCCTGAA
GTCCAAAAGCACGCCACTCAAATCCTCTGGAATATGCTAAGACAGGAGGAGGAAGAG
TTACAGGACATACTTCCACCCTGTGGTGAGACCAGTCAGAGAACATGTGAGGCCGC
CTCTCTGTGGACTCCCAGGAGGCAGACAGTGGCTTGGATTCTGGGACAGAACGCTTT
CCCTCCATCAGTGAGTCATTGATGAATCGGAACTCAGTATTGTCAGATCCTGGACTA
GACAGCCCTCAAACCTCCCCTGTAATCCTGGCCAGGGTGGCCCAGCACCACAGGCGA
CAGGGCTCAGATGCAGCGTTGCTCCCGCTCAACCACCAGGGTATAGATCAAAGCCCA
AAGCCTCTGATTATTGGCCCAGAGGAAGATTATGACCCAGGTTATTTCAACAATGAG
AGTGACATCATCTTCCAAGATCTTGAAAAACTGAAGTCACATCCAGCTTACTTGGTA
GTTTTTCTACGTTACATCCTCTCTCAGGCAGACCCTGGCCCCCTGCTTTTTTATTTG
TGTTCAGAAGTTTATCAACAGACAAATCCCAAAGATTCCCGAAGTCTGGGGAAAGAC
ATCTGGAACATTTTCCTGGAGAAAAATGCGCCTCTCAGAGTGAAGATCCCTGAGATG
TTGCAGGCTGAAATTGACCTACGCCTGCGGAACAATGAGGACCCTCGCAATGTGCTC
TGTGAAGCTCAGGAGGCAGTCATGCTGGAAATCCAGGAGCAGATCAACGACTACAGA
TCCAAGCGTACTCTGGGCCTGGGCAGCCTCTATGGTGAAAATGACCTGCTAGGCCTG
GATGGGGACCCTCTTCGAGAACGCCAAATGGCTGAGAAGCAGCTGGCTGCCCTTGGA
GATATCTTGTCCAAATATGAGGAAGATCGGAGTGCCCCATGGACTTTGCTGTTAAT
ACCTTTATGAGCCACGCTGGGATCCGTCTTCGGGAGTCTCGATCCTCCTGCACGGCA
GAAAAGACCCAGTCTGCCCCTGACAAGGACAAGTGGCTGCCCTTCTTCCCTAAGACC
AAGAAGCAGAGCAGCAATTCCAAGAAAGAAAAGGATGCCTTGGAGGACAAGAAGCGA
AACCCCATCCTCAGATATATTGGGAAGCCCAAGAGCTCCTCTCAGAGCATTAAGCCA
GGCAATGTGAGGAACATCATTCAGCACTTTGAGAACAGCCATCAGTATGATGTCCCA
GAGCCGGGGACACAACGACTCTCAACAGGAAGCTTTCCTGAGGACCTGCTGGAGAGT
GACAGTTCGCGCTCAGAGATTCGACTGGGCCGCTCTGGGAGCCTCAAGGGCCGGGAA
GAGATGAAGCGATCCCGGAAAGCAGAGAACGTGCCCCGGCCTCGAAGTGACGTTGAC
ATGGATGCTGCTGCAGAGGCTGCCCGCCTTCACCAGTCAGCCTCGTCCTCTGCCTCC
AGCCTCTCCACCAGGTCTCTTGAGAACCCAACCCCTCCCTTCACCCCCAAAATGGGC
CGCAGGAGCATTGAGTCCCCAATCTGGGGTTCTGTACAGACGTCATCCTTCCCCAC
CTCCTGGAGGATGATCTGGGCCAATTGTCTGACCTGGAGCCAGAGCCAGAGGTCCAA
AACTGGCAGCATACAGTAGGCAAGGATGTGGTGGCCAACCTGACCCAGAGGGAAATT
GACCGGCAAGAGGTCATCAATGAGCTTTTGTGACAGAAGCATCTCACCTGCGCACA
CTCCGAGTCCTGGACCTCATCTTCTACCAGCGCATGAGAAAGGAGAACCTAATGCCT
CGGGAAGAGCTAGCGCGGCTCTTCCCTAACCTGCCTGAGCTCATAGAGATTCACAAT
TCCTGGTGTGAGGCCATGAAGAAGCTCCGGGAGGAGGGCCCCATTATCAGAGACATC
AGTGACCCCATGCTGGCTCGGTTTGATGGTCCTGCCCGAGAAGAACTCCAGCAAGTA
GCTGCACAATTCTGTTCCTATCAGTCAGTAGCCCTAGAGCTAATCAGGACTAAGCAA
CGTAAGGAGAGTCGGTTCCAGCTCTTCATGCAGGAGGCTGAGAGCCACCCTCAGTGC
CGGCGTCTGCAGCTCCGAGACCTCATCGTCTCTGAAATGCAACGGCTCACCAAGTAC
CCACTGCTGCTAGAGAACATCATCAAGCACACAGAGGGTGGCACCTCTGAGCATGAG
```

FIGURE 16B

```
AAGCTCTGCCGTGCCCGGGACCAGTGCCGGGAGATTCTCAAGTTTGTGAATGAAGCA
GTAAAGCAGACAGAGAACCGCCACCGGCTAGAGGGGTACCAGAAACGCCTGGATGCC
ACTGCCCTAGAGCGGGCCAGCAACCCCTTGGCAGCAGAGTTCAAGAGCCTGGATCTT
ACAACAAGGAAGATGATCCACGAGGGGCCTCTGACCTGGAGGATCAGCAAAGACAAG
ACCCTGGACCTCCAGGTGCTTCTGCTTGAGGACCTGGTGGTACTGCTGCAGAGACAA
GAGGAGCGGCTGCTGCTAAAGTGCCACAGCAAGACAGCCGTGGGCTCCTCCGACAGC
AAGCAGACGTTCAGCCCTGTGCTGAAGCTCAATGCTGTGCTCATCCGCTCCGTGGCT
ACAGACAAGCGAGCCTTCTTCATCATCTGCACCTCCGAGCTGGGCCCTCCCCAGATC
TATGAGCTGGTTGCATTGACGTCATCAGACAAGAATATATGGATGGAGCTCTTAGAA
GAGGCCGTGCAGAATGCCACCAAGCACCCTGGAGCTGCCCCAATCCCCATCCATCCC
TCACCACCAGGATCCAGGAGCCGGCCTACCAGGGCTCCACCTCCAGCAGGGTAGAA
ATAAATGACTCAGAAGTATATCACACTGAAAAGAACCCAAGAAGCTACCTGAAGGC
CCCGGGCCTGAGCAGAGAGTTCAAGACAAGCAGCTGATAGCACAAGGGGAGCCTGTG
CAGGAAGAGGATGAAGAGGAATTGAGGACCTTGCCTCGAGCTCCCCCCTCCCTGGAT
GGAGAAAACAGAGGCATCAGGACAAGGGACCCTGTCCTTCTGGCCCTCACAGGCCCT
CTGCTCATGGAGGGACTTGCTGATGCTGCCCTGGAAGATGTGGAGAACTTGCGTCAC
CTGATCCTGTGGAGCCTGCTGCCTGGTCACACTGTGAAGACTCAGGCTGCTGGCGAG
CCTGAGGATGACCTCACACCCACCCCTTCTGTCGTGAGCATCACCTCTCACCCCTGG
GACCCAGGGTCCCCAGGGCAAGCTCCCACCATAAGTGACAGCACCCGACTTGCGAGG
CCAGAGGGCAGCCAGCCAGAGGGCGAGGATGTTGCTGTCAGTTCTCTGGCACACCTG
CCGCCAAGGACCAGAAGTTCTGGCGTCTGGGACTCTCCTGAGCTGGATAGGAATCCG
GCTGCAGAGGCTGCAAGCACAGAACCAGCAGCAAGTTACAAGGTTGTGAGAAAAGTC
TCTCTACTCCCTGGTGGTGGTGTCGGTGCAGCCAAGGTGGCGGGCAGCAATGCTATC
CCTGACAGTGGCCAGTCAGAATCTGAGCTATCTGAAGTGGAAGGCGGAGCACAGGCT
ACGGGGAACTGTTTCTATGTCAGCATGCCAGCAGGACCTCTGGACTCCAGCACTGAG
CCTACTGGGACACCCCAAGCCCCTCACAGTGTCACAGCCTCCCTGCATGGCCAACA
GAGCCTCAGCCCTACAGGGGAGTCCGTGGGGGTCAGTGTTCCAGCCTGGTCCGCAGG
GATGTGGATGTGATCTTCCATACCATCGAGCAGCTCACCATCAAGCTTCACAGACTG
AAGGACATGGAGCTGGCCCACAGAGAGCTGCTCAAGTCCCTTGGAGGAGAGTCATCG
GGTGGAACCACACCTGTGGGGAGTTTTCACACAGAGGCAGCCAGATGGACAGACTAC
TCCCTCTCCTCCAGCCAAGGAAGCCCTGGCCTCTGATTCCAAAATGGTCAGGAG
CAGGGGTCCTGCCCTGAAGAAGGCTCCGACATCGCCCTGGAAGACAGTGCCACTGAC
ACAGCTGTGTCACCAGGACCATAG
```

FIGURE 17

MSIRLPHSIDRSASKKQSHLSSPIASWLSSLSSLGDSTPERTSPSHHRQPSDTSETTAG
LVQRCVIIQKDQHGFGFTVSGDRIVLQSVRPGGAAMKAGVKEGDRIIKVNGTMVTNSS
HLEVVKLIKSGAYAALTLLGSSPPSVGVSGLQQNPSVAGVLRVNPIIPPPPPPPPLPPP
QHITGPKPLQDPEVQKHATQILWNMLRQEEEELQDILPPCGETSQRTCEGRLSVDSQEA
DSGLDSGTERFPSISESLMNRNSVLSDPGLDSPQTSPVILARVAQHHRRQGSDAALLPL
NHQGIDQSPKPLIIGPEEDYDPGYFNNESDIIFQDLEKLKSHPAYLVVFLRYILSQADP
GPLLFYLCSEVYQQTNPKDSRSLGKDIWNIFLEKNAPLRVKIPEMLQAEIDLRLRNNED
PRNVLCEAQEAVMLEIQEQINDYRSKRTLGLGSLYGENDLLGLDGDPLRERQMAEKQLA
ALGDILSKYEEDRSAPMDFAVNTFMSHAGIRLRESRSSCTAEKTQSAPDKDKWLPFFPK
TKKQSSNSKKEKDALEDKKRNPILRYIGKPKSSSQSIKPGNVRNIIQHFENSHQYDVPE
PGTQRLSTGSFPEDLLESDSSRSEIRLGRSGSLKGREEMKRSRKAENVPRPRSDVDMDA
AAEAARLHQSASSSASSLSTRSLENPTPPFTPKMGRRSIESPNLGFCTDVILPHLLEDD
LGQLSDLEPEPEVQNWQHTVGKDVVANLTQREIDRQEVINELFVTEASHLRTLRVLDLI
FYQRMRKENLMPREELARLFPNLPELIEIHNSWCEAMKKLREEGPIIRDISDPMLARFD
GPAREELQQVAAQFCSYQSVALELIRTKQRKESRFQLFMQEAESHPQCRRLQLRDLIVS
EMQRLTKYPLLLENIIKHTEGGTSEHEKLCRARDQCREILKFVNEAVKQTENRHRLEGY
QKRLDATALERASNPLAAEFKSLDLTTRKMIHEGPLTWRISKDKTLDLQVLLLEDLVVL
LQRQEERLLLKCHSKTAVGSSDSKQTFSPVLKLNAVLIRSVATDKRAFFIICTSELGPP
QIYELVALTSSDKNIWMELLEEAVQNATKHPGAAPIPIHPSPPGSQEPAYQGSTSSRVE
INDSEVYHTEKEPKKLPEGPGPEQRVQDKQLIAQGEPVQEEDEEELRTLPRAPPSLDGE
NRGIRTRDPVLLALTGPLLMEGLADAALEDVENLRHLILWSLLPGHTVKTQAAGEPEDD
LTPTPSVVSITSHPWDPGSPGQAPTISDSTRLARPEGSQPEGEDVAVSSLAHLPPRTRS
SGVWDSPELDRNPAAEAASTEPAASYKVVRKVSLLPGGGVGAAKVAGSNAIPDSGQSES
ELSEVEGGAQATGNCFYVSMPAGPLDSSTEPTGTPPSPSQCHSLPAWPTEPQPYRGVRG
GQCSSLVRRDVDVIFHTIEQLTIKLHRLKDMELAHRELLKSLGGESSGGTTPVGSFHTE
AARWTDYSLSPPAKEALASDSQNGQEQGSCPEEGSDIALEDSATDTAVSPGP.

FIGURE 18

ATGGACGTGAACCTTGCCCCGCTCCGTGCCTGGGATGATTTCTTCCCGGGCTCTGATCG
TTTCGCACGGCCGGACTTCAGGGATATATCCAAATGGAACAACCGTGTAGTGAGCAATC
TGCTCTATTACCAGACCAACTACCTGGTGGTGGCTGCCATGATGATTTCAGTCGTTGGG
TTTCTGAGCCCCTTCAACATGATCCTTGGAGGAATCATTGTGGTGCTGGTGTTCACGGG
GTTTGTGTGGGCAGCACACAATAAAGACATCCTCCGCCGGATGAAGAAGCAGTACCCAA
CGGCCTTTGTCATGGTGGTCATGCTAGCCAGCTACTTCCTCATATCCATGTTTGGGGGT
GTCATGGTCTTTGTGTTTGGCATCACGTTTCCCTTATTGTTGATGTTCATCCATGCATC
CCTGAGACTTCGAAACCTCAAGAACAAACTGGAAAATAAAATGGAGGGAATAGGCTTGA
AGAAAACGCCGATGGGCATCATCCTGGATGCCTTGGAACAGCAGGAAGACAGCATCAAT
AAATTTGCTGACTACATCAGCAAAGCCAGGGAGTAA

FIGURE 19

MDVNLAPLRAWDDFFPGSDRFARPDFRDISKWNNRVVSNLLYYQTNYLVVAAMMISVVG
FLSPFNMILGGIIVVLVFTGFVWAAHNKDILRRMKKQYPTAFVMVVMLASYFLISMFGG
VMVFVFGITFPLLLMFIHASLRLRNLKNKLENKMEGIGLKKTPMGIILDALEQQEDSIN
KFADYISKARE

FIGURE 20A

```
   1 gttggccacc atggggatgt accaagtgag actgtaggga aagaaggtgg tgactcgcgt
  61 gcctggctac tggctgctgc tcacctcgat gctacaagat tcctagcaag atcaaaactg
 121 accattaacc tacctctaca tccccctggc gccgttccag ggccaacgcc acattccctg
 181 ctgggcacgc aatggccgca cccccctcccg ctacagaagg ctcttttggt acacgcagtc
 241 cgaggtcgcc atggatcgga tgaagaagat caaacggcag ctgtcaatga cactccgagg
 301 gggccgaggc atagacaaga ccaatggtgt ccctgagcag ataggcctag atgagagtgg
 361 tggtggtggt ggcatgaccc ttggagaagc tcccacccgt gttgccctg gggaacttcg
 421 ctctattcgg ggcccactca gctctgcacc aggtctacct gggtttccca gtctgctcta
 481 ggggccatgt acacaaatgg atacgatgaa gaaatatatt atattggggg aaagagagtg
 541 ttcttgactc caaaggcctg gccttttccct cactctgcac cagagattgt gcatgaagac
 601 atgaagatgg gatctgatgg ggagagtgac caggcttcag ccacatcctc agatgaggtg
 661 cagtctccag tgagagtgcg catgcgcaac caccccccac gcaagatctc cactgaggat
 721 atcaacaaat gcctgtcact accagctgac atacggctgc ctgagggcta ccttgagaag
 781 ctgacccctca atagccccat cggtgataag cctcttagcc ggcgcctccg gccagtcagc
 841 ttgtctgaga ttggctttgg aaaactggag acctacatca aactagacaa gctgggtgag
 901 ggtacctatg ccactgtcta caaaggcaaa agcaagctca cagacaacct tgtagcactt
 961 aaggagatca gactggaaca cgaagaaggg gcaccctgca ctgctatccg ggaagtatcc
1021 ctgcttaagg acctcaagca tgccaacatc gtcacactac atgacattat ccacacagag
1081 aagtccctca cccttgtctt tgaatacttg gacaaggacc tgaagcagta cctggatgac
1141 tgtggaaatg tcatcaacat gcacaatgtg aaactgttcc tgttccagtt gctccgtggc
1201 ctggcctact gccacaggca gaaggtgcta caccgagacc tcaagcccca gaacctactc
1261 atcaacgaga ggggagagct caaactggca gactttggcc tggcttacgc caagtcaatt
1321 cctactaaaa catactccaa cgaagtggtg acactgtggt accggccccc tgacatctta
1381 cttgggtcca cagactactc cggccaaatt gacatgtggg gtgttggctg catcttttat
1441 gagatggcca caggccggcc cctcttccca ggctccacag tggaagaaca gctgcacttc
1501 atcttccgca ttttgggaac cccaactgag gacacatggc caggtatcct gtccaatgaa
1561 gagtttagaa catacaacta ccccaagtac cgagccgagg cccttctgag gcatgcaccc
1621 cgacttgaat gcgatggagc tgacctcctc accaagctgc tgcagtttga gggtcgcaat
1681 cggatctctg ctgaggatgc catgaaacat ccattctttc tcagcttggg ggagcggatc
1741 cacaaaactc ctgacactac ttccatattt gcactaaagg aggtacagct acaaaaggag
1801 gccaacattc ggtccacttc tatgcctgac tcaggcaggc cagctttccg tgtggtggat
1861 accgagttct aagccaagtt ttaagccaca gacagaccaa ggccccagca ggcagcggct
1921 ggagggatgc cacacccctc acaggacagc ccccatctgc aatcctccct gcttgttgcc
1981 tgcttacctg cctgagccac actccctgc caacttgtcc cctgccacct gtccaaacac
2041 cgaactactg gcctggcctg tcaacccaac cactggcctg tctgctgggt gctaacaaag
2101 ctctcaccac tactttgctt gatgtgtctg tctctgtctt ggtagatgct ggtggaccga
2161 atggccgtgc cagcttttcca cactaaggct aggccttccc ctcttcatca cactctctcc
2221 caggaccact accccatggc cagccagggg tttggagcta gcccaggcca ggctcttaat
2281 cgactttgac tagaaggtag tgagtgatgc cttgggtctg agcatcattt gcctgcttcc
2341 cacctgtccc acttgcctct gttgtatggg cttttttta gtttctttta ttgttttttt
2401 attattttaa atgaggttct cacttttaa tgcaatatct ctgtatacag actggttggg
```

FIGURE 20B

```
2461 cactactccc tgagtgtggc actcccacag tattttgtgc aatgaagtcc cactcccacc
2521 ctttgagagg tagggaccca gaccctattc agatcctcac catcactaga ccctggaatt
2581 ggctatggga aagcatgcct cagccactca ccttcctccc ctacctagcg ttcccagcta
2641 tagggggacc tgagaactac cagagagtgg gagatggaca tggtggggcc tacttttcc
2701 ctccttcagt cccgtagcca gggcctcctt ccttctcagg gtcttcccca gcccagctct
2761 gcctagccct cctgccctgt cctactcggt gctgttgagt aggggctctg cctggaatcg
2821 agcagcttag tgaggagcca tatataatat gtgcacaagc aggaggacat gtgggagctt
2881 gtgcccaatt gttacacccc aatccctagg agggtcaggc aggccaagga cagtctcctg
2941 gatggatggt ttgctcccct tactccacct taagccttgg gacccttaag cagggtggga
3001 gggcaaggga gggtgccctc ctagtggggt ttgggggggat tgggttcctg aatgcaccat
        3061 aatcgctgta tgaaatatta aaaaaaagtc taaagtgaaa aaaaaaaaa a
```

FIGURE 21

MDRMKKIKRQLSMTLRGGRGIDKTNGVPEQIGLDESGGGGGMTLGEAPTRVAPGELRSI
RGPLSSAPEIVHEDMKMGSDGESDQASATSSDEVQSPVRVRMRNHPPRKISTEDINKCL
SLPADIRLPEGYLEKLTLNSPIGDKPLSRRLRPVSLSEIGFGKLETYIKLDKLGEGTYA
TVYKGKSKLTDNLVALKEIRLEHEEGAPCTAIREVSLLKDLKHANIVTLHDIIHTEKSL
TLVFEYLDKDLKQYLDDCGNVINMHNVKLFLFQLLRGLAYCHRQKVLHRDLKPQNLLIN
ERGELKLADFGLAYAKSIPTKTYSNEVVTLWYRPPDILLGSTDYSGQIDMWGVGCIFYE
MATGRPLFPGSTVEEQLHFIFRILGTPTEDTWPGILSNEEFRTYNYPKYRAEALLRHAP
RLECDGADLLTKLLQFEGRNRISAEDAMKHPFFLSLGERIHKLPDTTSIFALKEVQLQK
EANIRSTSMPDSGRPAFRVVDTEF

FIGURE 22

MYTNGYDEEIYYIGGKRVFLTPKAWPFPHSAPEIVHEDMKMGSDGESDQASATSSDEVQ
SPVRVRMRNHPPRKISTEDINKCLSLPADIRLPEGYLEKLTLNSPIGDKPLSRRLRPVS
LSEIGFGKLETYIKLDKLGEGTYATVYKGKSKLTDNLVALKEIRLEHEEGAPCTAIREV
SLLKDLKHANIVTLHDIIHTEKSLTLVFEYLDKDLKQYLDDCGNVINMHNVKLFLFQLL
RGLAYCHRQKVLHRDLKPQNLLINERGELKLADFGLAYAKSIPTKTYSNEVVTLWYRPP
DILLGSTDYSGQIDMWGVGCIFYEMATGRPLFPGSTVEEQLHFIFRILGTPTEDTWPGI
LSNEEFRTYNYPKYRAEALLRHAPRLECDGADLLTKLLQFEGRNRISAEDAMKHPFFLS
LGERIHKLPDTTSIFALKEVQLQKEANIRSTSMPDSGRPAFRVVDTEF

GLUTAMATE TRANSPORTER ASSOCIATED PROTEINS AND METHODS OF USE THEREOF

RELATED APPLICATIONS

This application claims priority under 35 U.S.C. § 119 (e)(1) to U.S. Provisional Application Ser. No. 60/161,007, filed Oct. 23, 1999, and to U.S. Provisional Application Ser. No. 60/206,157, filed on May 22, 2000, each herein incorporated by reference in their entirety.

STATEMENT AS TO FEDERALLY SPONSORED RESEARCH

This invention was made with Government support under NS33958 and NS70151, awarded, by the National Institutes of Health (NINDS). The Government may have certain rights in the invention.

FIELD OF THE INVENTION

The present invention relates generally to protein-protein interactions and more specifically to Glutamate Transporter Associated Proteins involved in mediating glutamate transport, chloride transport and cytoskeletal stability and their association with glutamate transporter proteins.

BACKGROUND OF THE INVENTION

Glutamate is the major excitatory neurotransmitter in the mammalian central nervous system, acting on postsynaptic ionotropic glutamate receptors (particularly NMDA and AMPA receptors). In addition, glutamate stimulates a subset of metabotropic glutamate receptors (particularly the group I metabotropic glutamate receptors mGluR1a and mGluR5) concentrated in the postsynaptic membrane. The timely removal of glutamate from the synaptic cleft is critical to preventing desensitization resulting from continued exposure of the postsynaptic receptors to glutamate. Removal of glutamate from the synaptic cleft is mediated by a class of molecules known as glutamate transporter proteins located on surrounding astroglia and neurons. Five distinct, high-affinity, sodium-dependent glutamate transporters have been identified in animal and human central nervous system. Rat GLAST, GLT-1, EAAC1 (EAAT1, EAAT2 and EATT3, respectively, in human), EAAT4 and EAAT5 differ in structure, pharmacological properties and tissue distribution.

Glutamate transport is a sodium- and potassium-coupled process capable of concentrating intracellular glutamate up to 10,000-fold compared with the extracellular environment. The stoichiometry of the process has been studied and at several models exist proposing various ionic exchanges. In one model derived from salamander retinal glial cells, the transport process is coupled to the co-transport of two sodium ions and the counter-transport of one potassium ion and one hydroxyl ion. (Bouvier et al. (1992), Nature 360:471–474). Another model proposes that with EAAC1, one glutamate is co-transported with three sodium ions and one hydrogen ion, with the counter-transport of one potassium ion (Zerangue et al., Nature (1996) 383:634–637). Yet another study suggests that two sodium ions are co-transported with one glutamate molecule (Hart et al., Science (1998) 280:2112–2114).

The cloning of glutamate transporter subtypes and detailed electrophysiological studies of these proteins reveals that glutamate transporters also possess channel-like properties. The conduct chloride flux is not thermodynamically coupled to substrate transport, although at transportable substrate is required for the chloride conductance. The binding of glutamate to the transporter may change its conformational state to form the chloride channel.

In addition to their possible role in development and learning (due to their potential for modulating normal synaptic transmission), the regulation of synaptic glutamate transporters is likely to play an important role in acute and chronic neurological processes. They can be involved through the disruption of synaptic transmission as well as through glutamate mediated excitotoxicity. Several diseases are associated with disruptions in glutamate transport.

Loss of cerebellar Purkinje cell is the hall mark of several inherited neurodegenerative diseases, including the trinucleotide repeat diseases such as spinocerebellar ataxia type 1 (SCA1), and is commonly associated with neurotoxicity of chronic ethanol ingestion, and with certain paraneoplastic neurological disorders. Although the molecular event that initiates the disease is known—a trinucleotide repeat—the cellular mechanisms responsible for Purkinje cell degeneration is not known. The selective loss of glutamate transporters such as EAAT4 could make the protein an attractive candidate for a downstream event.

Similarly, dysregulation of glutamate transporter EAAC1 could also have pathological consequences. EAAC1 has the unusual localization to GABA pre-synaptic terminals. This transport could serve as a precursor transporter, supplying extracellular glutamate for GABA re-synthesis. GABA normally is synthesized, via glutamate amino decarboxylase, from glutamate. The source of this glutamate has been traditionally thought to be cellular glutamate. However, the unique localization of the glutamate transporter to GABA terminals suggests that these transporters supply precurser glutamate for GABA re-synthesis. Thus, EAAC1 could serve as an important step in GABAergic neurotransmission. Modulation of GABAergic metabolism is associated with a number of neurological disorders, including epilepsy, tremors, and spasticity. In addition, some theories of schizophrenia include disturbances of glutamate and GABA metabolism.

Accordingly, there is a need in the art for compounds that regulate glutamate transport and in particular, compounds and molecules that interact with glutamate transporter proteins.

SUMMARY OF THE INVENTION

The present invention provides a family of proteins that interact with glutamate transporter proteins. Through their interaction with glutamate transporter proteins, Glutamate Transporter Associated Proteins modulate glutamate transport, and also effect cytoskeletal organization and stability as well as chloride flux.

In one embodiment of the invention, there is provided a substantially pure polypeptide characterized as modulating intracellular glutamate transport, interacting with a glutamate transporter protein, and having an expression pattern in the brain. In addition, the polypeptide can have at least one PDZ domain, at least one regulatory G-protein domain, at lest one pleckstrin homology domain, at least one proline-rich domain and at least one guanine exchange factor domain. The polypeptide can have at least one pleckstrin homology domain, at least one spectrin repeat and at least one α-actinin domain.

In an additional embodiment of the invention, there is provided a substantially pure polypeptide characterized as modulating intracellular glutamate transport; interacting with a glutamate transporter protein; having an expression pattern in neural non-neuronal tissues; having at least one kinase C domains; having four transmembrane domains; and being hydrophobic.

In another embodiment of the invention, there is provided a substantially pure polypeptide having an amino acid sequence as set forth in SEQ ID NO:2, SEQ ID NO:4, SEQ ID NO:6 or conservative variants thereof.

In still another embodiment of the invention, there is provided an isolated polynucleotide selected from the group consisting of: (a) a polynucleotide encoding a polypeptide having an amino acid sequence as set forth in SEQ ID NO:2; (b) a polynucleotide of (a), wherein T can be U; (c) a polynucleotide complementary to (a) or (b); (d) a polynucleotide having a nucleotide sequence as set forth in SEQ ID NO:1; (e) degenerate variants of (a), (b), (c) or (d); and (f) a fragment of (a), (b), (c), (d) or (e) having at least 15 base pairs and hybridizes to a polynucleotide encoding a polypeptide as set forth in SEQ ID NO:2.

In yet another embodiment of the invention, there is provided an isolated polynucleotide selected from the group consisting of: (a) a polynucleotide encoding a polypeptide having an amino acid sequence as set forth in SEQ ID NO:4; (b) a polynucleotide of (a), wherein T can be U; (c) a polynucleotide complementary to (a) or (b); (d) a polynucleotide having a nucleotide sequence as set forth in SEQ ID NO:3; (e) degenerate variants of (a), (b), (c) or (d); and (e) a fragment of (a), (b), (c), (d) or (e) having at least 15 base pairs and hybridizes to a polynucleotide encoding a polypeptide as set forth in SEQ ID NO:4.

In still another embodiment of the invention, there is provided an isolated polynucleotide selected from the group consisting of: (a) a polynucleotide encoding a polypeptide having an amino acid sequence as set forth in SEQ ID NO:6; (b) a polynucleotide of (a), wherein T can be U; (c) a polynucleotide complementary to (a) or (b); (d) a polynucleotide having a nucleotide sequence as set forth in SEQ ID NO:5; (e) degenerate variants of (a), (b), (c) or (d); and (f) a fragment of (a), (b), (c), (d) or (e) having at least 15 base pairs and hybridizes to a polynucleotide encoding a polypeptide as set forth in SEQ ID NO:6.

In still a further embodiment of the invention, there is provided an antibody that binds to a Glutamate Transporter Associated Protein or binds to immunoreactive fragments thereof. The antibody can be polyclonal or monoclonal.

In yet another embodiment of the invention, there is provided an expression vector comprising a polynucleotide encoding Glutamate Transporter Associated Protein, e.g., SEQ ID NO:1, SEQ ID NO:3, SEQ ID NO:5, or complementary nucleotides thereof and fragments thereof. The vectors can be virus derived or plasmid derived.

In another embodiment of the invention, there is provided a method for producing a Glutamate Transporter Associated Protein polypeptide by culturing a host cell containing a nucleotide encoding a Glutamate Transporter Associated Protein under conditions suitable for the expression of the polypeptide and recovering the polypeptide from the host cell culture.

In another embodiment of the invention, there is provided a substantially pure polypeptide that interacts with the amino acid sequence QEAELTLP (SEQ ID NO:9) or amino acid sequence GRGGNESVM (SEQ ID NO:10).

In still another embodiment of the invention, there is provided a substantially pure polypeptide that interacts with the amino acid sequence set forth in SEQ ID NO:12.

In still another embodiment of the invention, there is provided a substantially pure polypeptide that interacts with the amino acid sequence set forth in SEQ ID NO:13.

In an addition embodiment of the invention, there is provided a method for identifying a compound that modulates a cellular response mediated by a Glutamate Transporter Associated Protein. The method includes incubating the compound with a cell expressing a Glutamate Transporter Associated Protein and a glutamate transporter protein under conditions sufficient to permit the components to interact and comparing a cellular response in the cell incubated with the compound with the cellular response of a cell not incubated with the compound.

In yet another embodiment of the invention, there is provided a method for identifying a compound that inhibits an interaction between a Glutamate Transporter Associated Protein and a glutamate transporter protein. The method includes contacting a Glutamate Transporter Associated Protein with a glutamate transporter protein in the presence of the compound and comparing the formation of a Glutamate Transporter Associated Protein-glutamate transporter protein complex in the presence of the compound with a formation of the complex in the absence of the compound.

In still another embodiment of the invention, there is provided a transgenic non-human animal having a transgene that expresses a Glutamate Transporter Associated Protein chromosomally integrated into the germ cells of the animal. An embodiment of the invention provides a method for producing such transgenic animals.

In another embodiment of the invention, there is provided a computer readable medium having stored thereon a nucleic acid sequence selected from the group consisting of SEQ ID NO:1, SEQ ID NO:3, SEQ ID NO:5 and sequences substantially identical thereto, or a polypeptide sequence selected from the group consisting of SEQ ID NO:2, SEQ ID NO:4, SEQ ID NO:6 and sequences substantially identical thereto.

In another embodiment of the invention, there is provided a computer system comprising a processor and a data storage device wherein said data storage device has stored thereon a nucleic acid sequence selected from the group consisting of SEQ ID NO:1, SEQ ID NO:3, SEQ ID NO:5 and sequences substantially identical thereto, or a polypeptide sequence selected from the group consisting SEQ ID NO:2, SEQ ID NO:4, SEQ ID NO:6 and sequences substantially identical thereto.

In yet another embodiment of the invention, there is provided a method for comparing a first sequence to a reference sequence wherein said first sequence is a nucleic acid sequence selected from the group consisting SEQ ID NO:1, SEQ ID NO:3, SEQ ID NO:5 and sequences substantially identical thereto, or a polypeptide sequence selected from the group consisting of SEQ ID NO:2, SEQ ID NO:4, SEQ ID NO:6 and sequences substantially identical thereto. The method comprises reading the first sequence and the reference sequence through use of a computer program which compares sequences, and determining differences between the first sequence and the reference sequence with the computer program.

In yet another embodiment of the invention there is provided a method for identifying a feature in a sequence wherein the sequence is selected from the group consisting of a nucleic acid sequence SEQ ID NO:1, SEQ ID NO:3, SEQ ID NO:5 sequences substantially identical thereto, or a polypeptide sequence SEQ ID NO:2, SEQ ID NO:4, SEQ ID NO:6 and sequences substantially identical thereto. The method includes reading the sequence through the use of a computer program which identifies features in sequences and identifying features in the sequences with the computer program.

BRIEF DESCRIPTION OF THE DRAWINGS

FIGS. 1A and 1B show schematic representations of GTRAP4-41 and GTRAP4-48, respectively.

FIG. 14 (A–C) shows a nucleic acid sequence of a polynucleotide encoding GTRAP4-41 (SEQ ID NO:1).

FIG. 15 shows an amino acid sequence of GTRAP4-41 (SEQ ID NO:2).

FIG. 16 (A and B) shows a nucleic acid sequence of a polynucleotide encoding GTRAP4-48 (SEQ ID NO:3).

FIG. 17 shows an amino acid sequence of GTRAP4-48 (SEQ ID NO:4).

FIG. 18 shows a nucleic acid sequence of a polynucleotide encoding GTRAP3-18 (SEQ ID NO:5).

FIG. 19 shows an amino acid sequence of GTRAP3-18 (SEQ ID NO:6).

FIG. 20 (A and B) shows a nucleic acid sequence of a polynucleotide encoding PCTAIRE-1 (SEQ ID NO:7).

FIG. 21 shows an amino acid sequence of PCTAIRE-1a (SEQ ID NO:8).

FIG. 22 shows an amino acid sequence of PCTAIRE1b (SEQ ID NO:22).

DETAILED DESCRIPTION OF THE INVENTION

Figure 2:
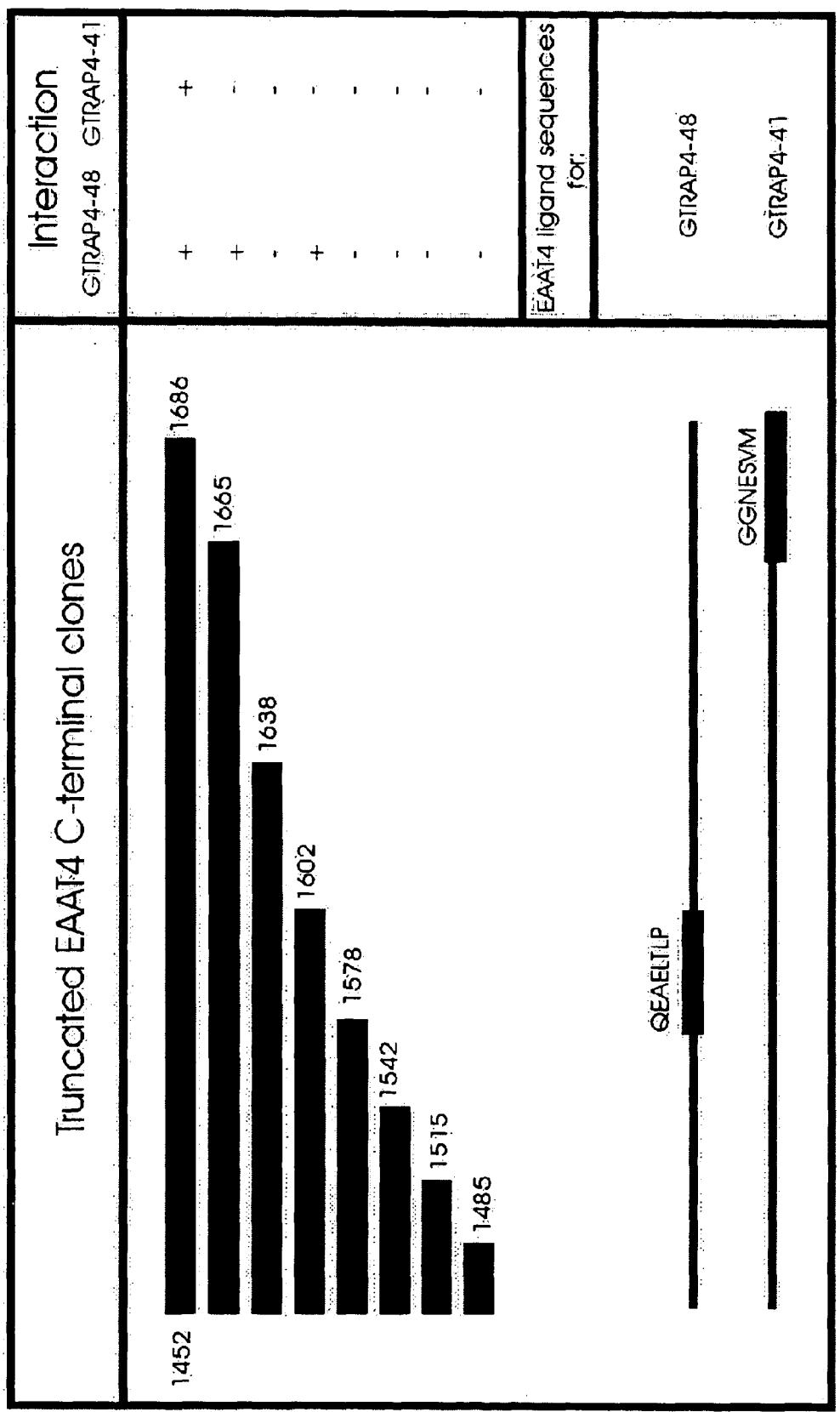
FIG. 2 shows overlapping deletion mutants of the carboxy terminus of EAAT4 used to identify domains interacting with GTRAP4-41 and GTRAP4-48.

The identification of molecules regulating the transport of neurotransmitters is central to understanding the mechanisms of neural activity, synaptic plasticity and learning. Efficient and rapid removal of neurotransmitters from the synaptic cleft by neurotransmitter transporters is critical to synaptic transmission. Re-uptake of glutamate by glutamate transporters both terminates the synaptic action of glutamate, thereby preventing glutamate-mediated exotoxicity and recaptures glutamate molecules for possible reuse.

Accordingly, one embodiment of the invention provides a substantially pure polypeptide characterized as modulating intracellular glutamate transport, interacting with a glutamate transporter protein and having an expression pattern in the brain. A polypeptide molecule having such characteristics is known as a Glutamate Transporter Associated Protein (GTRAP). Glutamate Transporter Associated Proteins can be further characterized as having at least one PDZ domain, having at least one regulatory G-protein domain, having at least one pleckstrin homology domain, having at least one proline-rich domain, and having at least one guanine exchange factor domain. Glutamate Transporter Associated Protein can also be characterized as having at least one pleckstrin homology domain, having at least one spectrin repeat, and having at least one α-actinin domain.

Glutamate Transporter Associated Proteins modulate glutamate transport. Glutamate transport refers to the active movement of glutamate across a cellular membrane. Glutamate transport is an essential component of central nervous system glutamatergic neurotransmission. For example, glutamate transport is essential in the inactivation of synaptically released glutamate and the prevention of excitotoxicity. The concentration of glutamate is higher in the terminal than in the synaptic cleft, even following neurotransmitter release. Nonetheless, the transporters take up glutamate from the synaptic cleft and transport it into the cell. Glutamate transporters also serve to bring glutamate into the cell for use in cellular metabolism, e.g. provide glutamate for new synthesis of neurotransmitter GABA. GTRAPs associated with some types of glutamate transporter protein, for example, glutamate transporter protein EAAT4, stimulate glutamate transport. GTRAPs associated with other types of glutamate transporter proteins, for example, EAAC1, inhibit glutamate transport. While not wishing to be bound to any one mechanism, the modulation in transport appears to be effected through a change in Vmax or a change in Km (see Examples section). Glutamate transporter proteins can signal messages to the cell about transport activities e.g. GTRAP48 activate G-protein signaling].

Glutamate Transporter Associated Proteins share several common features. All GTRAPs are able to interact with at least one glutamate transporter protein. Glutamate transporter proteins include GLAST, GLT-1, EAAC1, EAAT1, EAAT2, EAAT3, EAAT4 and EAAT5. Glutamate transporters share over 50% amino acid sequence identity with each other, and display almost identical hydrophobic profiles including six prominent hydrophobic peaks, followed by a small hydrophobic peak and long hydrophobic stretch. The proteins are generally 500 to 600 amino acids in length, with high conservation of sequence in the transmembrane domain. The carboxyl and amino terminal domains are intracellular and have the least sequence conservation among all transporters. Less is known about the genomic structure of the transporter proteins. The glutamate transporter family is quite distinct in structure from the 12 transmembrane α-helix arrangement of another sodium- and chloride-dependent transporter family related to dopamine and serotonin transport. The glutamate transporter family transports L-glutamate, D-aspartate and L-aspartate and some other acidic amino acids such as threo-β-hydroxyaspartate (THA) and cysteate. However, the transporters display distinct properties in substrate or inhibitor selectivity, e.g. dihydrokainate is a specific inhibitor of GLT-1 and EAAC1 transports cysteine with much higher affinity than the other transporters. Various studies have suggested that transporters may form homomultimers, perhaps dimers, but physiological transport may only require monomers of the protein.

Immunohistochemical studies show that GLAST and GLT-1 (EAAT1 and EAAT2) are localized primarily in astrocytes. In the adult CNS, GLT-1 is widely distributed throughout the brain and spinal cord in astroglial cell bodies and processes, while GLAST protein is localized in glial cells of cerebellar molecular and granule cell layers, and in some astroglia throughout the brain Double labeling post-embedding electron microscopic immunocytochemistry shows the two glial transporters, GLT-1 and GLAST, expressed in the same cell membrane. Each protein forms oligomeric complexes but GLT-1 and GLAST may not complex with each other. Antisense knock-down studies show that these two glial transporters are responsible for over 80% of glutamate uptake in the brain, an observation later confirmed in GLT-1 null mice. Quantitative immuno-blotting and electron microscopy indicate that the glial transporters are quite abundant; GLAST and GLT-1 respectively, are 2300 and 8500 molecules per $\mu m^2$ in CA1 hippocampus membrane, and 4700 and 740 molecules per $\mu m^2$ in the cerebellar molecular layer.

Developmental studies reveal differential expression of GLT-1 and GLAST mRNA and protein. Initially expression of GLAST predominates throughout the CNS, followed by a shift in expression to the cerebellum, whereas GLT-1 expression remains throughout most of the CNS. A dramatic up-regulation of GLT-1 gene expression at post-natal day 14 coincides with the post-natal development of glutamatergic transmission in the cortex.

GLT-1 mRNA and protein can, under certain conditions be found in neurons, e.g. cultured hippocampal neurons. Transiently localized GLT-1 on growing axons and axon pathways can also be detected. Additional studies in models of ischemic brain injury and in fetal ovine brain suggest rare neuronal expression of GLT-1 as well.

EAAC1 and EAAT4 are neuronal transporters. EAAC1 immunoreactivity is particularly high in regions such as the hippocampus, cerebellum and basal ganglia. It is widely distributed in neurons such as large cortical pyramidal neurons, and is also present in non-glutamatergic neurons including GABAergic cerebellar Purkinje cells. Ultrastructural studies suggest that EAAC1 is not a presynaptic transporter of glutamatergic neurons. In fact, EAAC1 appears to be primarily localized in the somatodendritic compartment, and is already expressed at stages preceding synaptic contact formation. Rarely, EAAC1 is found in pre-synaptic terminals, which are always inhibitory (e.g GABAergic). Ultra structurally, EAAC1 is present in dendrites and somas. Detailed EM-gold studies of synapses indicate that the protein is most often peri-synaptic in location, like EAAT4. EAAC1 is also widely expressed outside the central nervous system, so it may serve metabolic functions in neurons. For example, it may provide glutamate for resynthesis of GABA in GABAergic terminals, where the protein has been localized (Rothstein, et al. (1994) Neuron 13:713–725, herein incorporated by reference in its entirety). In fact, studies using antisense oligonucleotides to inhibit EAAC1 suggest that this transporter may, in part, regulate GABA synthesis.

EAAT4 is largely expressed in the cerebellum with very faint levels of expression in hippocampus, neocortex, striatum, brain stem and thalamus, in both the adult human and rat CNS. EAAT4 is present at low concentrations in the synaptic membrane, but is highly enriched in the parts of the dendritic and spine membranes facing astrocytes. A functional relationship may exist between EAAT4 and the glial transporters, and that EAAT4, having a prominent $Cl^-$-channel property, may function as a combined transporter and inhibitory glutamate receptor. The average density of EAAT4 protein in the Purkinje cell membrane has been calculated to be 1800 molecules per $\mu^2$. Immunohistochemical as well as immunoblot analysis demonstrates that during development EAAT4 protein is expressed in the human cerebellum both pre- and post-natally, while its expression in the frontal cortex is restricted to fetal stages. In the cerebellum, Purkinje cells show faint EAAT4 immunoreactivity at gestation week 17. However, EAAT4 expression becomes increasingly intense from gestation week 23 to the infantile period. After the late infantile period, EAAT4 immunoreactivity shows the same pattern as in adults. The intracellular localization of EAAT4 also changes with development. In the early embryonic period, EAAT immunoreactivity is found in the short processes of the Purkinje cells, while in the late fetal to early infantile periods, EAAT4 immunoreactivity is found in the cell bodies and dendrites, and in the late infantile period, it is found in the spines.

Glutamate transporters and glutamate receptors are compartmentalized in and around the synaptic cleft and proteins capable of glutamate receptor membrane targeting and the epitopes responsible for these events are known. For example, three cytoplasmic molecules have been recently identified which bind to the final eight amino acids in the C-terminus of GluR2 and GluR3, but not to GluR1 or NR1. These molecules, named GRIP and ABP are all synaptically localized in the hippocampus and contain one or more PDZ domains, protein binding motifs of between 70 and 90 amino acids which have recently been implicated in the localization of other highly regulated proteins. None of these molecules interacts or regulates glutamate transporters.

Several studies document a role for neurons in modulating the expression and activity of glutamate transporters. Pathway lesion studies suggest that neurons can influence the astroglial (but not neuronal) expression of glutamate transporter subtypes. This has been validated in vitro, where astroglial (EAAT2) expression in cultured astrocytes appears to depend on neurons most likely secreted factors, including glutamate itself. In fact, a number of trophic factors that modulate EAAT2 expression in various in vitro preparations have been identified. Protein kinase C phosphorylation of EAAT2 (GLT-1) has also been found to stimulate transport. Transporters can also be directly regulated through other signaling pathways. Activity of EAAC1 (and GABA and serotonin transporters) can be regulated through expression at the cell surface, via regulated cellular trafficking, occurring in part through protein kinase C and phosphatidylinositol 3-kinase pathways.

Glutamate Transporter Associated Proteins have an expression pattern in brain tissue. Immunofluorescence staining of brain tissue reveals a pattern of GTRAP immunoreactivity in brain tissue. Prominent immunolocalization is observed in the cerebellar cortex, especially in Purkinje cell somas and dendrites with no axonal localization. Expression is also observed in other brain regions including striatum, hippocampus and thalamus.

Expression of certain Glutamate Transporter Associated Proteins is observed outside the brain. For example, GTRAP3-18 is expressed in the liver, kidney, heart, muscle as well as in the central nervous system.

Glutamate Transporter Associated Proteins can include at least one PDZ domain, at least one regulatory G-protein domain, at least one pleckstrin homology domain (PH), at least one proline-rich domain, at least one guanine exchange factor domain (Db1), at least one spectrin repeat and at least one α-actinin domain. Methods to identify such domains are known to those of skill in the art. For example, computer programs that compare invention nucleic acid and amino acid sequences to nucleic acid and amino acid sequences, and identify regions of homology can be used to identify such domains.

Exemplary Glutamate Transporter Associated Proteins of the invention include sequences as set forth in SEQ ID NO:2, SEQ ID NO:4, SEQ ID NO:6 and conservative variants thereof. The terms "conservative variation" and "substantially similar" as used herein denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine, glutamic acid for aspartic acid, or glutamine for asparagine, and the like. The terms "conservative variation" and "substantially similar" also include the use of a substituted amino acid in place of an unsubstituted parent amino acid provided that antibodies raised to the substituted polypeptide also immunoreact with the unsubstituted polypeptide.

Also contemplated by the invention are polypeptides that share at least 90% sequence homology to the polypeptide sequences set forth as SEQ ID NO:2, SEQ ID NO:4 and SEQ ID NO:6. Sequence homology can be determined by those of skill in the art, for example, by computer programs that compare sequences such as Blast.

Exemplary polynucleotides encoding a Glutamate Transporter Associated Proteins are set forth as SEQ ID NO:1, SEQ ID NO:3, SEQ ID NO:5 and SEQ ID NO:7. The term "polynucleotide", "nucleic acid", "nucleic acid sequence", or "nucleic acid molecule" refers to a polymeric form of nucleotides at least 10 bases in length. By "isolated polynucleotide" is meant a polynucleotide that is not immediately contiguous with both of the coding sequences with which it is immediately contiguous (one on the 5' end and one on the 3' end) in the naturally occurring genome of the organism from which it is derived. The term therefore includes, for example, a recombinant DNA which is incorporated into a vector; into an autonomously replicating plasmid or virus; or into the genomic DNA of a prokaryote or eukaryote, or which exists as a separate molecule (e.g. a cDNA) independent of other sequences. The nucleotides of the invention can be deoxyribonucleotides, ribonucleotides in which uracil (U) is present in place of thymine (T), or modified forms of either nucleotide. The nucleotides of the invention can be complementary to the deoxynucleotides or to the ribonucleotides. A polynucleotide encoding a Glutamate Transporter Associated Protein includes "degenerate variants", sequences that are degenerate as a result of the genetic code. There are 20 natural amino acids, most of which are specified by more than one codon. Therefore, all degenerate nucleotide sequences are included in the invention as long as the amino acid sequence of a polypeptide encoded by the nucleotide sequence of SEQ ID NO:1, SEQ ID NO;3, SEQ ID NO:5 or SEQ ID NO:7 is functionally unchanged.

A nucleic acid molecule encoding a Glutamate Transporter Associated Protein includes sequences encoding functional Glutamate Transporter Associated Protein polypeptides as well as functional fragments thereof. As used herein, the term "functional polypeptide" refers to a polypeptide which possesses biological function or activity which is identified through a defined functional assay, and which is associated with a particular biologic, morphologic, or phenotypic alteration in the cell. The term "functional fragments of Glutamate Transporter Associated Protein," refers to fragments of a Glutamate Transporter Associated Protein that retain a Glutamate Transporter Associated Protein activity, e.g., the ability to interact with a glutamate transporter protein, modulate intracellular glutamate transport, and the like. Additionally, functional Glutamate Transporter Associated Protein fragments may act as competitive inhibitors of Glutamate Transporter Associated Protein binding to a glutamate transporter protein, for example. Biologically functional fragments can vary in size from a polypeptide fragment as small as an epitope capable of binding an antibody molecule to a large polypeptide capable of participating in the characteristic induction or programming of phenotypic changes within a cell. Nucleotide fragments of the invention have at least 15 base pairs and hybridize to a polynucleotide encoding a polypeptide as set forth in SEQ ID NO:2, SEQ ID NO:4, SEQ ID NO:6, SEQ ID NO:8 or SEQ ID NO:22.

Further embodiments of the invention provide isolated polynucleotides, wherein the nucleotide is at least 15 base pairs in length which hybridizes under moderately to highly stringent conditions to DNA encoding a polypeptide as set forth in SEQ ID NO:2 or to DNA encoding a polypeptide as set forth in SEQ ID NO:4, or SEQ ID NO:6. In nucleic acid hybridization reactions, the conditions used to achieve a particular level of stringency will vary, depending on the nature of the nucleic acids being hybridized. For example, the length, degree of complementarity, nucleotide sequence composition (e.g., GC v. AT content), and nucleic acid type (e.g., RNA v. DNA) of the hybridizing regions of the nucleic acids can be considered in selecting hybridization conditions. An additional consideration is whether one of the nucleic acids is immobilized, for example, on a filter.

An example of progressively higher stringency conditions is as follows: 2×SSC/0.1% SDS at about room temperature (hybridization conditions); 0.2×SSC/0.1% SDS at about room temperature (low stringency conditions); 0.2×SSC/0.1% SDS at about 42° C. (moderately stringent conditions); and 0.1×SSC at about 68° C. (highly stringent conditions). Washing can be carried out using only one of these conditions, e.g., high stringency conditions, or each of the conditions can be used, e.g., for 10–15 minutes each, in the order listed above, repeating any or all of the steps listed. However, as mentioned above, optimal conditions will vary, depending on the particular hybridization reaction involved, and can be determined empirically.

Antibodies of the invention may bind to Glutamate Transporter Associated Proteins provided by the invention to prevent normal interactions of Glutamate Transporter Associated Proteins. Binding of antibodies to Glutamate Transporter Associated Protein can interfere with for example, glutamate transport, with cytoskeletal stability by interfering with intracellular protein binding, with expression patterns of Glutamate Transporter Associated Proteins or with interactions with glutamate transporter proteins. Furthermore, binding of antibodies to Glutamate Transporter Associated Proteins can interfere with the localization of glutamate transporter proteins on cellular membranes.

The antibodies of the invention can be used in any subject in which it is desirable to administer in vitro or in vivo immunodiagnosis or immunotherapy. The antibodies of the invention are suited for use, for example, in immunoassays in which they can be utilized in liquid phase or bound to a solid phase carrier. In addition, the antibodies in these immunoassays can be detectably labeled in various ways. Examples of types of immunoassays which can utilize antibodies of the invention are competitive and non-competitive immunoassays in either a direct or indirect format. Examples of such immunoassays are the radioimmunoassay (RIA), the enzyme-linked immunosorbant assay (ELISA) and the sandwich (immunometric) assay. Detection of the antigens using the antibodies of the invention can be done utilizing immunoassays which are run in either the forward, reverse, or simultaneous modes, including immunohistochemical assays on physiological samples. Those of skill in the art will know, or can readily discern, other immunoassay formats without undue experimentation.

The term "antibody" as used in this invention includes intact molecules as well as fragments thereof, such as Fab, F(ab')2, and Fv which are capable of binding to an epitopic determinant present in an invention polypeptide. Such antibody fragments retain some ability to selectively bind with its antigen or receptor.

Methods of making these fragments are known in the art. (See for example, Harlow and Lane, Antibodies: A Laboratory Manual, Cold Spring Harbor Laboratory, New York (1988), incorporated herein by reference). Monoclonal antibodies are made from antigen containing fragments of the protein by methods well known to those skilled in the art (Kohler & Milstein, *Nature* 256:495 (1975); Coligan et al., sections 2.5.1–2.6.7; and Harlow et al., *Antibodies: A Laboratory Manual*, page 726 (Cold Spring Harbor Pub. 1988), which are hereby incorporated by reference. Briefly, monoclonal antibodies can be obtained by injecting mice with a composition comprising an antigen/ligand, verifying the presence of antibody production by analyzing a serum sample, removing the spleen to obtain B lymphocytes, fusing the B lymphocytes with myeloma cells to produce hybridomas, cloning the hybridomas, selecting positive clones that produce antibodies to the antigen, and isolating the antibodies from the hybridoma cultures. Monoclonal antibodies can be isolated and purified from hybridoma cultures by a variety of well-established techniques. Such isolation techniques include affinity chromatography with Protein-A Sepharose, size-exclusion chromatography, and ion-exchange chromatography. See, e.g., Coligan et al., sections 2.7.1–2.7.12 and sections 2.9.1–2.9.3; Barnes et al., "Purification of Immunoglobulin G (IgG)" in *Methods In Molecular Biology*, VOL. 10, pages 79–104 (Humana Press 1992).

Antibodies which bind to an invention Glutamate Transporter Associated Protein polypeptide can be prepared using an intact polypeptide or fragments containing small peptides of interest as the immunizing antigen. For example, it may be desirable to produce antibodies that specifically bind to the amino- or carboxyl-terminal domains of an invention polypeptide. For the preparation of polyclonal antibodies, the polypeptide or peptide used to immunize an animal is derived from translated cDNA or chemically synthesized and can be conjugated to a carrier protein, if desired. Commonly used carrier proteins which may be chemically coupled to the immunizing peptide include keyhole limpet hemocyanin (KLH), thyroglobulin, bovine serum albumin (BSA), tetanus toxoid, and the like.

Invention polyclonal or monoclonal antibodies can be further purified, for example, by binding to and elution from a matrix to which the polypeptide or a peptide to which the antibodies were raised is bound. Those of skill in the art will know of various techniques common in the immunology arts for purification and/or concentration of polyclonal antibodies, as well as monoclonal antibodies (See, for example, Coligan, et al., Unit 9, Current Protocols in Immunology, Wiley Interscience, 1994, incorporated herein by reference).

The antibodies of the invention can be bound to many different carriers and used to detect the presence of an antigen comprising the polypeptides of the invention. Examples of well-known carriers include glass, polystyrene, polypropylene, polyethylene, dextran, nylon, amylases, natural and modified celluloses, polyacrylamides, agaroses and magnetite. The nature of the carrier can be either soluble or insoluble for purposes of the invention. Those skilled in the art will know of other suitable carriers for binding antibodies, or will be able to ascertain such, using routine experimentation.

There are many different labels and methods of labeling known to those of ordinary skill in the art. Examples of the types of labels which can be used in the present invention include enzymes, radioisotopes, fluorescent compounds, colloidal metals, chemiluminescent compounds, phosphorescent compounds, and bioluminescent compounds. Those of ordinary skill in the art will know of other suitable labels for binding to the antibody, or will be able to ascertain such, using routine experimentation.

Another technique which may also result in greater sensitivity consists of coupling the antibodies to low molecular weight haptens. These haptens can then be specifically detected by means of a second reaction. For example, it is common to use such haptens as biotin, which reacts with avidin, or dinitrophenyl, puridoxal, and fluorescein, which can react with specific antihapten antibodies.

In using the monoclonal and polyclonal antibodies of the invention for the in vivo detection of antigen, e.g., a Glutamate Transporter Associated Protein, the detectably labeled antibody is given a dose which is diagnostically effective. The term "diagnostically effective" means that the amount of detectably labeled antibody is administered in sufficient quantity to enable detection of the site having the antigen comprising a polypeptide of the invention for which the antibodies are specific.

The concentration of delectably labeled antibody which is administered should be sufficient such that the binding to those cells having the polypeptide is detectable compared to the background. Further, it is desirable that the detectably labeled antibody be rapidly cleared from the circulatory system in order to give the best target-to-background signal ratio.

As a rule, the dosage of detectably labeled antibody for in vivo treatment or diagnosis will vary depending on such factors as age, sex, and extent of disease of the individual. Such dosages may vary, for example, depending on whether multiple injections are given, antigenic burden, and other factors known to those of skill in the art.

A polynucleotide agent can be contained in a vector, which can facilitate manipulation of the polynucleotide, including introduction of the polynucleotide into a target cell. The vector can be a cloning vector, which is useful for maintaining the polynucleotide, or can be an expression vector, which contains, in addition to the polynucleotide, regulatory elements useful for expressing the polynucleotide and, where the polynucleotide encodes a peptide, for expressing the encoded peptide in a particular cell. An expression vector can contain the expression elements necessary to achieve, for example, sustained transcription of the encoding polynucleotide, or the regulatory elements can be operatively linked to the polynucleotide prior to its being cloned into the vector.

An expression vector (or the polynucleotide) generally contains or encodes a promoter sequence, which can provide constitutive or, if desired, inducible or tissue specific or developmental stage specific expression of the encoding polynucleotide, a poly-A recognition sequence, and a ribosome recognition site or internal ribosome entry site, or other regulatory elements such as an enhancer, which can be tissue specific. The vector also can contain elements required for replication in a prokaryotic or eukaryotic host system or both, as desired. Such vectors, which include plasmid vectors and viral vectors such as bacteriophage, baculovirus, retrovirus, lentivirus, adenovirus, vaccinia virus, semliki forest virus and adeno-associated virus vectors, are well known and can be purchased from a commercial source (Promega, Madison Wis.; Stratagene, La Jolla Calif.; GIBCO/BRL, Gaithersburg Md.) or can be constructed by one skilled in the art (see, for example, *Meth. Enzymol.*, Vol. 185, Goeddel, ed. (Academic Press, Inc., 1990); Jolly, *Canc. Gene Ther.* 1:51–64, 1994; Flotte, *J. Bioenerg. Biomemb.* 25:37–42, 1993; Kirshenbaum et al., *J. Clin. Invest.* 92:381–387, 1993; each of which is incorporated herein by reference).

A polynucleotide useful in a method of the invention also can be operatively linked to tissue specific regulatory element, for example, a neuron specific regulatory element, such that expression of an encoded peptide agent is restricted to neurons in an individual, or to neurons in a mixed population of cells in culture, for example, an organ culture. For example, neuronal or glial promoters such as the myelin basic protein promoter, other neuronal-specific promoters, and astroglial promoters (e.g. GFAP-glial fibrillary acidic protein), known to those of skill in the art may be used. Muscle-regulatory elements including, for example, the muscle creatine kinase promoter (Sternberg et al., *Mol. Cell. Biol.* 8:2896–2909, 1988, which is incorporated herein by reference) and the myosin light chain enhancer/promoter (Donoghue et al., *Proc. Natl. Acad. Sci., USA* 88:5847–5851, 1991, which is incorporated herein by reference) are well known in the art. A variety of other promoters have been identified which are suitable for up regulating expression in cardiac tissue. Included, for example, are the cardiac I-myosin heavy chain (AMHC) promoter and the cardiac I-actin promoter. Other examples of tissue-specific regulatory elements include, tissue-specific promoters, pancreatic (insulin or elastase), and actin promoter in smooth muscle cells. Through the use of promoters, such as milk-specific promoters, recombinant retroviruses may be isolated directly from the biological fluid of the progeny.

A Glutamate Transporter Associated Protein polynucleotide of the invention can be inserted into a vector, which can be a cloning vector or a recombinant expression vector. The term "expression vector" refers to a plasmid, virus or other vehicle known in the art that has been manipulated by insertion or incorporation of a polynucleotide, particularly, with respect to the present invention, a polynucleotide encoding all or a peptide portion of a Glutamate Transporter Associated Protein. Such expression vectors contain a promoter sequence, which facilitates the efficient transcription of the inserted genetic sequence of the host. The expression vector generally contains an origin of replication, a promoter, as well as specific genes which allow phenotypic selection of the transformed cells. Vectors suitable for use in the present invention include, but are not limited to, the T7-based expression vector for expression in bacteria (Rosenberg, et al., *Gene* 56:125, 1987), the pMSXND expression vector for expression in mammalian cells (Lee and Nathans, *J. Biol. Chem.* 263:3521, 1988) and baculovirus-derived vectors for expression in insect cells. The DNA segment can be present in the vector operably linked to regulatory elements, for example, a promoter, which can be a T7 promoter, metallothionein I promoter, polyhedrin promoter, or other promoter as desired, particularly tissue specific promoters or inducible promoters.

Viral expression vectors can be particularly useful for introducing a polynucleotide useful in a method of the invention into a cell, particularly a cell in a subject. Viral vectors provide the advantage that they can infect host cells with relatively high efficiency and can infect specific cell types. For example, a polynucleotide encoding a Glutamate Transporter Associated Protein or functional peptide portion thereof can be cloned into a baculovirus vector, which then can be used to infect an insect host cell, thereby providing a means to produce large amounts of the encoded protein or peptide portion. The viral vector also can be derived from a virus that infects cells of an organism of interest, for example, vertebrate host cells such as mammalian, avian or piscine host cells. Viral vectors can be particularly useful for introducing a polynucleotide useful in performing a method of the invention into a target cell. Viral vectors have been developed for use in particular host systems, particularly mammalian systems and include, for example, retroviral vectors, other lentivirus vectors such as those based on the human immunodeficiency virus (HIV), adenovirus vectors, adeno-associated virus vectors, herpesvirus vectors, vaccinia virus vectors, and the like (see Miller and Rosman, *BioTechniques* 7:980–990, 1992; Anderson et al., *Nature* 392:25–30 Suppl., 1998; Verma and Somia, *Nature* 389:239–242, 1997; Wilson, *New Engl. J. Med.* 334:1185–1187 (1996), each of which is incorporated herein by reference).

When retroviruses, for example, are used for gene transfer, replication competent retroviruses theoretically can develop due to recombination of retroviral vector and viral gene sequences in the packaging cell line utilized to produce the retroviral vector. Packaging cell lines in which the production of replication competent virus by recombination has been reduced or eliminated can be used to minimize the likelihood that a replication competent retrovirus will be produced. All retroviral vector supernatants used to infect cells are screened for replication competent virus by standard assays such as PCR and reverse transcriptase assays. Retroviral vectors allow for integration of a heterologous gene into a host cell genome, which allows for the gene to be passed to daughter cells following cell division.

A polynucleotide, which can be contained in a vector, can be introduced into a cell by any of a variety of methods known in the art (Sambrook et al., *Molecular Cloning: A laboratory manual* (Cold Spring Harbor Laboratory Press 1989); Ausubel et al., *Current Protocols in Molecular Biology*, John Wiley and Sons, Baltimore, Md. (1987, and supplements through 1995), each of which is incorporated herein by reference). Such methods include, for example, transfection, lipofection, microinjection, electroporation and, with viral vectors, infection; and can include the use of liposomes, microemulsions or the like, which can facilitate introduction of the polynucleotide into the cell and can protect the polynucleotide from degradation prior to its introduction into the cell. The selection of a particular method will depend, for example, on the cell into which the polynucleotide is to be introduced, as well as whether the cell is isolated in culture, or is in a tissue or organ in culture or in situ.

Introduction of a polynucleotide into a cell by infection with a viral vector is particularly advantageous in that it can efficiently introduce the nucleic acid molecule into a cell ex vivo or in vivo (see, for example, U.S. Pat. No. 5,399,346, which is incorporated herein by reference). Moreover, viruses are very specialized and can be selected as vectors based on an ability to infect and propagate in one or a few specific cell types. Thus, their natural specificity can be used to target the nucleic acid molecule contained in the vector to specific cell types. As such, a vector based on an HIV can be used to infect T cells, a vector based on an adenovirus can be used, for example, to infect respiratory epithelial cells, a vector based on a herpesvirus can be used to infect neuronal cells, and the like. Other vectors, such as adeno-associated viruses can have greater host cell range and, therefore, can be used to infect various cell types, although viral or non-viral vectors also can be modified with specific receptors or ligands to alter target specificity through receptor mediated events.

A polynucleotide sequence encoding a Glutamate Transporter Associated Protein can be expressed in either prokaryotes or eukaryotes. Hosts can include microbial, yeast, insect and mammalian organisms. Methods of expressing polynucleotides having eukaryotic or viral sequences in prokaryotes are well known in the art, as are biologically functional viral and plasmid DNA vectors capable of expression and replication in a host. Methods for constructing an expression vector containing a polynucleotide of the invention are well known, as are factors to be considered in selecting transcriptional or translational control signals, including, for example; whether the polynucleotide is to be expressed preferentially in a particular cell type or under particular conditions (see, for example, Sambrook et al., supra, 1989).

A variety of host cell/expression vector systems can be utilized to express a Glutamate Transporter Associated Protein coding sequence, including, but not limited to, microorganisms such as bacteria transformed with recombinant bacteriophage DNA, plasmid DNA or cosmid DNA expression vectors; yeast cells transformed with recombinant yeast expression vectors; plant cell systems infected with recombinant virus expression vectors such as a cauliflower mosaic virus or tobacco mosaic virus, or transformed with recombinant plasmid expression vector such as a Ti plasmid; insect cells infected with recombinant virus expression vectors such as a baculovirus; animal cell systems infected with recombinant virus expression vectors such as a retrovirus, adenovirus or vaccinia virus vector; and transformed animal cell systems genetically engineered for stable expression. Where the expressed Glutamate Transporter Associated Protein is post-translationally modified, for example, by glycosylation, it can be particularly advantageous to select a host cell/expression vector system that can effect the desired modification, for example, a mammalian host cell/expression vector system.

Depending on the host cell/vector system utilized, any of a number of suitable transcription and translation elements, including constitutive and inducible promoters, transcription enhancer elements, transcription terminators, and the like can be used in the expression vector (Bitter et al., *Meth. Enzymol.* 153:516–544, 1987). For example, when cloning in bacterial systems, inducible promoters such as pL of bacteriophage Σ, plac, ptrp, ptac (ptrp-lac hybrid promoter) and the like can be used. When cloning in mammalian cell systems, promoters derived from the genome of mammalian cells, for example, a human or mouse metallothionein promoter, or from mammalian viruses, for example, a retrovirus long terminal repeat, an adenovirus late promoter or a vaccinia virus 7.5K promoter, can be used. Promoters produced by recombinant DNA or synthetic techniques can also be used to provide for transcription of the inserted GDF receptors coding sequence.

In yeast cells, a number of vectors containing constitutive or inducible promoters can be used (see Ausubel et al., supra, 1987, see chapter 13; Grant et al., *Meth. Enzymol.* 153:516–544, 1987; Glover, *DNA Cloning* Vol. II (IRL Press, 1986), see chapter 3; Bitter, *Meth. Enzymol.* 152:673–684, 1987; see, also, *The Molecular Biology of the Yeast Saccharomyces* (Eds., Strathern et al., Cold Spring Harbor Laboratory Press, 1982), Vols. I and II). A constitutive yeast promoter such as ADH or LEU2 or an inducible promoter such as GAL can be used (Rothstein, *DNA Cloning* Vol. II (supra, 1986), chapter 3). Alternatively, vectors can be used which promote integration of foreign DNA sequences into the yeast chromosome.

Eukaryotic systems, particularly mammalian expression systems, allow for proper post-transtational modifications of expressed mammalian proteins. Eukaryotic cells which possess the cellular machinery for proper processing of the primary transcript, glycosylation, phosphorylation, and advantageously, plasma membrane insertion of the gene product can be used as host cells for the expression of a Glutamate Transporter Associated Protein, or functional peptide portion thereof.

Mammalian cell systems which utilize recombinant viruses or viral elements to direct expression can be engineered. For example, when using adenovirus expression vectors, the Glutamate Transporter Associated Protein coding sequence can be ligated to an adenovirus transcription/translation control complex, e.g., the late promoter and tripartite leader sequence. Alternatively, the vaccinia virus 7.5K promoter can be used (Mackett et al., *Proc. Natl. Acad. Sci., USA* 79:7415–7419, 1982; Mackett et al., *J. Virol.* 49:857–864, 1984; Panicali et al., *Proc. Natl. Acad. Sci., USA* 79:4927–4931, 1982). Particularly useful are bovine papilloma virus vectors, which can replicate as extrachromosomal elements (Sarver et al., *Mol. Cell. Biol.* 1:486, 1981). Shortly after entry of this DNA into mouse cells, the plasmid replicates to about 100 to 200 copies per cell. Transcription of the inserted cDNA does not require integration of the plasmid into the host cell chromosome, thereby yielding a high level of expression. These vectors can be used for stable expression by including a selectable marker in the plasmid, such as, for example, the neo gene. Alternatively, the retroviral genome can be modified for use as a vector capable of introducing and directing the expression of the Glutamate Transporter Associated Protein gene in host cells (Cone and Mulligan, *Proc. Natl. Acad. Sci., USA* 81:6349–6353, 1984). High level expression can also be achieved using inducible promoters, including, but not limited to, the metallothionein IIA promoter and heat shock promoters.

For long term, high yield production of recombinant proteins, stable expression is preferred. Rather than using expression vectors which contain viral origins of replication, host cells can be transformed with Glutamate Transporter Associated Protein cDNA controlled by appropriate expression control elements such as promoter, enhancer, sequences, transcription terminators, and polyadenylation sites, and a selectable marker. The selectable marker in the recombinant plasmid can confer resistance to the selection, and allows cells to stably integrate the plasmid into their chromosomes and grow to form foci, which, in turn can be cloned and expanded into cell lines. For example, following the introduction of foreign DNA, engineered cells can be allowed to grow for 1 to 2 days in an enriched media, and then are switched to a selective media. A number of selection systems can be used, including, but not limited to, the herpes simplex virus thymidine kinase (Wigler et al., *Cell* 11:223, 1977), hypoxanthine-guanine phosphoribosyltransferase (Szybalska and Szybalski, *Proc. Natl. Acad. Sci., USA* 48:2026, 1982), and adenine phosphoribosyltransferase (Lowy, et al., *Cell* 22:817, 1980) genes can be employed in tk⁻, hgprt⁻ or aprt⁻ cells respectively. Also, antimetabolite resistance can be used as the basis of selection for dhfr, which confers resistance to methotrexate (Wigler, et al., *Proc. Natl. Acad. Sci. USA* 77:3567, 1980; O'Hare et al., *Proc. Natl. Acad. Sci., USA* 78: 1527, 1981); gpt, which confers resistance to mycophenolic acid (Mulligan and Berg, *Proc. Natl. Acad. Sci., USA* 78:2072, 1981); neo, which confers resistance to the aminoglycoside G-418 (Colberre-Garapin et al., *J. Mol. Biol.* 150:1, 1981); and hygro, which confers resistance to hygromycin (Santerre et al., *Gene* 30:147, 1984) genes. Additional selectable genes, including trpB, which allows cells to utilize indole in place of tryptophan; hisD, which allows cells to utilize histinol in place of histidine (Hartman and Mulligan, *Proc. Natl. Acad. Sci., USA* 85:8047, 1988); and ODC (ornithine decarboxylase) which confers resistance to the ornithine decarboxylase inhibitor, 2-(difluoromethyl)-DL-ornithine, DFMO (McConlogue, *Curr. Comm. Mol. Biol.* (Cold Spring Harbor Laboratory Press, 1987), also have been described.

When the host is a eukaryote, such methods of transfection of DNA as calcium phosphate coprecipitates, conventional mechanical procedures such as microinjection, electroporation, insertion of a plasmid encased in liposomes, or virus vectors can be used. Eukaryotic cells can also be cotransformed with DNA sequences encoding Glutamate Transporter Associated Proteins of the invention, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein. (Gluzman, *Eukaryotic Viral Vectors* (Cold Spring Harbor Laboratory Press, 1982)).

The invention provides a method for producing a polypeptide characterized as interacting with a glutamate transporter protein; modulating intracellular glutamate transport; having an expression pattern in Purkinje cells of the brain; and being hydrophobic. The invention also provides a method for producing a polypeptide encoded by the nucleotide sequence of SEQ ID NO:1, SEQ ID NO:3, SEQ ID NO:6 or fragments thereof, including culturing the host cell under conditions suitable for the expression of the polypeptide and recovering the polypeptide from the host cell culture.

A Glutamate Transporter Associated Protein polypeptide or a fragment thereof, can be encoded by a recombinant or non-recombinant nucleic acid molecule and expressed in a cell. Preparation of a Glutamate Transporter Associated Protein polypeptide by recombinant methods provides several advantages. In particular, the nucleic acid sequence encoding the Glutamate Transporter Associated Protein polypeptide can include additional nucleotide sequences encoding, for example, peptides useful for recovering the Glutamate Transporter Associated Protein polypeptide from the host cell. A Glutamate Transporter Associated Protein polypeptide can be recovered using well known methods, including, for example, precipitation, gel filtration, ion exchange, reverse-phase, or affinity chromatography (see, for example, Deutscher et al., "Guide to Protein Purification" in *Meth. Enzymol.*, Vol. 182, (Academic Press, 1990)). Such methods also can be used to purify a fragment of a Glutamate Transporter Associated Protein polypeptide, for example, a particular binding sequence, from a cell in which it is naturally expressed.

A recombinant nucleic acid molecule encoding a Glutamate Transporter Associated Protein polypeptide or a fragment thereof can include, for example, a protease site, which can facilitate cleavage of the Glutamate Transporter Associated Protein polypeptide from a non-Glutamate Transporter Associated Protein polypeptide sequence, for example, a tag peptide, secretory peptide, or the like. As such, the recombinant nucleic acid molecule also can encode a tag peptide such as a polyhistidine sequence, a FLAG peptide (Hopp et al., *Biotechnology* 6:1204 (1988)), a glutathione S-transferase polypeptide or the like, which can be bound by divalent metal ions, a specific antibody (U.S. Pat. No. 5,011,912), or glutathione, respectively, thus facilitating recovery and purification of the Glutamate Transporter Associated Protein polypeptide comprising the peptide tag. Such tag peptides also can facilitate identification of the Glutamate Transporter Associated Protein polypeptide through stages of synthesis, chemical or enzymatic modification, linkage, or the like. Methods for purifying polypeptides comprising such tags are well known in the art and the reagents for performing such methods are commercially available.

A nucleic acid molecule encoding a Glutamate Transporter Associated Protein polypeptide can be engineered to contain one or more restriction endonuclease recognition and cleavage sites, which can facilitate, for example, substitution of an element of the Glutamate Transporter Associated Protein polypeptide such as the selective recognition domain or, where present, a spacer element. As such, related Glutamate Transporter Associated Protein polypeptides can be prepared, each having a similar activity, but having specificity for different function-forming contexts. A restriction endonuclease site also can be engineered into (or out of) the sequence coding a peptide portion of the Glutamate Transporter Associated Protein polypeptide, and can, but need not change one or more amino acids encoded by the particular sequence. Such a site can provide a simple means to identify the nucleic acid sequence, based on cleavage (or lack of cleavage) following contact with the relevant restriction endonuclease, and, where introduction of the site changes an amino acid, can further provide advantages based on the substitution.

In another embodiment of the invention there is provided a substantially pure polypeptide which interacts with amino acid sequence QEAELTLP (SEQ ID NO:9) or the amino acid sequence GRGGNESVM (SEQ ID NO:10). In a preferred embodiment, polypeptides interact with a Glutamate Transporter Associated Protein encoded by a polynucleotide that hybridizes to SEQ ID NO:1. An exemplary protein containing amino acid sequences QEAELTLP (SEQ ID NO:9) and GRGGNESVM (SEQ ID NO:10) is glutamate transport protein EAAT4 (see Examples). In another embodiment of the invention, there is provided a polynucleotide encoding a substantially pure polypeptide which interacts with amino acid sequence QEAELTLP (SEQ ID NO:9) or the amino acid sequence GRGGNESVM (SEQ ID NO:10).

Another embodiment of the invention provides a substantially pure polypeptide which interacts with a polypeptide having the sequence of amino acids found at amino acid residues 527 to 534 of EAAT4 (SEQ ID NO:9). Still another embodiment of the invention provides a substantially pure polypeptide which interacts with a polypeptide sequence having the sequence of amino acid found at amino acid residues 555 to 561 of EAAT4 (SEQ ID NO:10).

Still another embodiment of the invention provides a substantially pure polypeptide which interacts with the amino acid sequence set forth in SEQ ID NO:12. Also provided is a substantially pure polypeptide which interacts with the amino acid sequence set forth in SEQ ID NO:13. Such amino acid sequence are used as "bait" sequences in yeast two-hybrid screen (See Example 1). Polypeptides identified in such screens are interacting proteins. Interacting proteins can mediate or modulate the activities of intracellular proteins.

A method is provided for identifying a compound that modulates a cellular response mediated by a Glutamate Transporter Associated Protein. The method includes incubating the compound with a cell expressing a Glutamate Transporter Associated Protein and a glutamate transporter protein under conditions sufficient to permit the compound to interact with the cell. The effect of the compound on the cellular response is determined, either directly or indirectly, and a cellular response is then compared with a cellular response of a control cell. A suitable control includes, but is not limited to, a cellular response of a cell not contacted with the compound. The cell may be any cell of interest, including but not limited to neuronal cells, glial cells, cardiac cells, bronchial cells, uterine cells, testicular cells, liver cells, renal cells, intestinal cells, cells from the thymus and spleen, placental cells, endothelial cells, endocrine cells including thyroid, parathyroid, pituitary and the like, smooth muscle cells and skeletal muscle cells. The term "incubating" includes conditions which allow contact between the test compound and the cell of interest. "Contacting" may include in solution or in solid phase.

The cellular response can be an increase in glutamate transport or a decrease in glutamate transport. Glutamate transport can be assessed by measuring glutamate uptake assays (see Example 8) and other assays known in the art.

The cellular response can be an increase in cytoskeletal stability or a decrease in cytoskeletal stability. Cytoskeletal stability can be assessed for example, by examining the formation and maintenance of intracellular protein interaction, cell-surface receptor clustering, clustering of glutamate transporter proteins, and the like. Methods for demonstrating such cellular responses are well known in the art (e.g. biochemical methods and histological methods). (See Kornau et al. (1997) Curr. Opin. Neurobiol. 2:368–373; and Huganir et al. (2000) Trends in Cell Biol. 10:274–280, each of which are herein incorporated by reference in their entirety and Examples section for additional methodology).

The cellular response can be an increase in chloride flux or a decrease in chloride flux. Chloride flux can be assessed by methods known to those of skill in the art such as electrophysiological methods including, but not limited to, patch clamp analysis.

Glutamate Transporter Associated Proteins contemplated for use in the invention method includes, for example, GTRAP4-41, GTRAP4-48, PCTAIRE-1a, PCTAIRE-1b, and GTRAP3-18. Glutamate transport proteins contemplated for use in the invention method include GLAST, GLT-1, EAAC1, EAAT1, EAAT2, EAAT3, EAAT4 and EAAT5.

In one preferred embodiment of the invention, the glutamate transport protein is EATT4 and the Glutamate Transporter Associated Protein is GTRAP4-41, GTRAP4-48, PCTAIRE-1a or PCTAIRE-1b. In another embodiment of the invention, the glutamate transport protein is EAAC1 and the Glutamate Transporter Associated Protein is GTRAP3-18.

In an embodiment of the invention, the cell expressing a Glutamate Transporter Associated Protein further expresses a RhoGEF protein. The Rho family of GTP-binding proteins regulates the rearrangement of the actin cytoskeleton. At least one Glutamate Transporter Associated Protein has a domain that permits interaction with a a guanine nucleotide exchange factor (GEF).

Compounds which modulate a cellular response include peptides, peptidomimetics, polypeptides, pharmaceuticals, chemical compounds and biological agents, for example. Antibodies, anti-epileptic compounds and combinatorial compound libraries can also be tested using the method of the invention. One class of organic molecules, preferably small organic compounds having a molecular weight of more than 50 and less than about 2,500 Daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups.

The test agent may also be a combinatorial library for screening a plurality of compounds. Compounds such as peptides identified in the method of the invention can be further cloned, sequenced, and the like, either in solution of after binding to a solid support, by any method usually applied to the isolation of a specific DNA sequence Molecular techniques for DNA analysis (Landegren et al., Science 242:229–237, 1988) and cloning have been reviewed (Sambrook et al., Molecular Cloning: a Laboratory Manual, 2nd Ed.; Cold Spring Harbor Laboratory Press, Plainview, N.Y., 1998, herein incorporated by reference).

Candidate compounds are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc., to produce structural analogs. Candidate agents are also found among biomolecules including, but not limited to: peptides, saccharides, fatty acids, steroids, purines, pyrimidines, derivatives, structural analogs or combinations thereof.

A variety of other agents may be included in the screening assay. These include agents like salts, neutral proteins, e.g., albumin, detergents, etc. that are used to facilitate optimal protein-protein binding and/or reduce nonspecific or background interactions. Reagents that improve the efficiency of the assay, such as protease inhibitors, nuclease inhibitors, antimicrobial agents and the like may be used. The mixture of components are added in any order that provides for the requisite binding. Incubations are performed at any suitable temperature, typically between 4 and 40° C. Incubation periods are selected for optimum activity, but may also be optimized to facilitate rapid high-throughput screening. Typically between 0.1 and 10 h will be sufficient.

Another embodiment of the invention provides a method for identifying a compound that can inhibit an interaction between a Glutamate Transporter Associated Protein and a glutamate transporter protein. The method includes contacting a Glutamate Transporter Associated Protein with a glutamate transporter protein in the presence of the compound, and comparing the formation of a Glutamate Transporter Associated Protein-glutamate transporter complex in the presence of the compound with the formation of the complex in the absence of the compound. Compounds that affect complex formation include peptides, polypeptides, pepidomimetics, chemical compounds and biological agents.

Contacting includes in solution and solid phase. In a preferred embodiment, isolated Glutamate Associated Transporter Proteins are utilized. However, partially purified proteins, fractions of cell extracts, whole cell extracts, or intact cells may be utilized with the method of the invention.

The complex of the Glutamate Associated Transporter Protein and the glutamate transporter protein can be separated from uncomplexed components by conventional means, well known to one of skill in the art. Separation can be accomplished by size separation, physical separation, antibody-mediated separation, or other standard methods. For example, immunoprecipitation or gel electrophoresis can be used to separate Glutamate Transporter Associated Protein-glutamate transporter protein complex from components that are not part of the complex (See Examples section for details).

Also provided is a method of modulating glutamate transport in a subject in need thereof. The method includes administering to the subject a therapeutically effective amount of a compound that modulates expression or activity of a Glutamate Transporter Associated Protein, thereby modulating glutamate transport.

A method is further provided for treating a subject with a disorder associated with glutamate transport comprising administering to the subject a therapeutically effective amount of a compound that modulates Glutamate Transporter Associated Protein activity or interaction with glutamate transporter protein.

Essentially, any disorder that is etiologically linked to glutamate transport or to a Glutamate Transporter Associated Protein could be considered susceptible to treatment with an agent that modulates Glutamate Transporter Associated Protein activity. The disorder may be a neuronal cell disorder. Examples of neuronal cell disorders include but are not limited to epilepsy, neurodegenerative disease (e.g. Alzheimer's disease, Huntington's disease, Amyotrophic lateral sclerosis, Parkinson's disease), spinocerebellar ataxia (SCA), especially of the SCA type 1, multiple sclerosis, disorders of neurotransmitter metabolism, including GABA metabolism and the like, Alzheimer's disease, Parkinson's disease, stroke, and brain or spinal cord injury/damage, including ischemic injury, and the like. Disorders also include glutamate toxicity, a disorder of memory, a disorder of learning or a disorder of brain development, and the like. Also included are disorders of glutamate-GABA imbalance such as schizophrenia, and the like.

In a preferred embodiment, the Glutamate Transporter Associated Protein is GTAP4-41, GTRAP4-48 or PCTAIRE-1 (including PCTAIRE-1a and PCTAIRE-1b) and the disorder is a disorder of the nervous system such as neurodegeneration or spinocerebellar ataxia type 1.

When the Glutamate Transporter Associated Protein is GTRAP3-18 the disorder is epilepsy or a disorder of GABA metabolism (e.g. tremors, spasticity, schizophrenia), for example.

Treatment can include modulation of Glutamate Transporter Associated Protein expression or activity by administration of a therapeutically effective amount of a compound that modulates Glutamate Transporter Associated Protein or Glutamate Transporter Associated Protein activity. The term "modulate" envisions the suppression of Glutamate Transporter Associated Protein activity or expression when the Glutamate Transporter Associated Protein is overexpressed or has an increased activity as compared to a control. The term "modulate" also includes the augmentation of the expression of Glutamate Transporter Associated Protein when it is underexpressed or has a decreased activity as compared to a control. The term "compound" as used herein describes any molecule, e.g., protein, nucleic acid, or pharmaceutical, with the capability of altering the expression of Glutamate Transporter Associated Protein polynucleotide or activity of Glutamate Transporter Associated Protein. Treatment can inhibit the transcription or translation of a Glutamate Transporter Associated Protein nucleotide sequence, inhibit the interaction of a domain of Glutamate Transporter Associated Protein with its target protein, may increase the avidity of this interaction by means of allosteric effects, may block the binding activity of a domain of Glutamate Transporter Associated Protein or influence other functional properties of Glutamate Transporter Associated Proteins.

Candidate agents include nucleic acids that interfere with expression of Glutamate Transporter Associated Protein, such as an antisense nucleic acid, ribozymes, and the like. Candidate agents also encompass numerous chemical classes wherein the agent modulates Glutamate Transporter Associated Protein expression or activity. For example, when the Glutamate Transporter Associated Protein is GTRAP3-18, the compound can be a polynucleotide having a nucleic acid sequence substantially similar to SEQ ID NO:20 (5'-GAGCGGGGCAAGGTTCAC-3'). A nucleotide encoded by SEQ ID NO:20 is antisense to the nucleic acid sequence of GTRRAP3-18 (See Example 13). GTRAP3-18 can also be modulated by retinoic acid (See Example 14).

When the Glutamate Transporter Associated Protein is GTRAP4-41, GTRAP4-48 or PCTAIRE-1, modulatory compounds include a polynucleotide having a nucleic acid sequence that is substantially similar to an antisense nucleic acid sequence that binds to a polynucleotide encoding GTRAP4-41, GTRAP4-48 or PCTAIRE-1.

Modulation of glutamate transport can be an increase in glutamate transport or a decrease in glutamate transport. When a disorder is associated with an increase in glutamate transport, compounds that decrease glutamate transport can be used. For example, compounds that modulate expression of GTRAP3-18 are contemplated. When a disorder is associated with a decrease in glutamate transport, compound that increase glutamate transport are contemplated. For example, compounds that modulate expression of GTRAP4-41, GTRAP4-48, or PCTAIRE-1 (a and b) are contemplated.

Detection of altered (decreased or increased) levels of Glutamate Transporter Associated Protein expression can be accomplished by hybridization of nucleic acids isolated from a cell of interest with a Glutamate Transporter Associated Protein of the invention. Analysis, such as Northern Blot analysis, are utilized to quantitate expression of Glutamate Transporter Associated Protein, such as to measure Glutamate Transporter Associated Protein transcripts. Other standard nucleic acid detection techniques will be known to those of skill in the art. Detection of altered levels of Glutamate Transporter Associated Protein can also accomplished using assays designed to detect Glutamate Transporter Associated Protein polypeptide. For example, antibodies or peptides that specifically bind a Glutamate Transporter Associated Protein polypeptide can be utilized. Analyses, such as radioimmune assay or immunohistochemistry, are then used to measure Glutamate Transporter Associated Protein, such as to measure protein concentration qualitatively or quantitatively.

Where a disorder is associated with the increased expression of Glutamate Transporter Associated Protein, nucleic acid sequences that interfere with the expression of Glutamate Transporter Associated Protein can be used. This approach also utilizes, for example, antisense nucleic acid, ribozymes, or triplex agents to block transcription or translation of Glutamate Transporter Associated Protein mRNA, either by masking that mRNA with an antisense nucleic acid or triplex agent, or by cleaving it with a ribozyme in disorders associated with increased Glutamate Transporter Associated Protein. Alternatively, a dominant negative form of Glutamate Transporter Associated Protein polypeptide could be administered.

When Glutamate Transporter Associated Protein is overexpressed, candidate agents include antisense nucleic acid sequences. Antisense nucleic acids are DNA or RNA molecules that are complementary to at least a portion of a specific mRNA molecule (Weintraub, 1990, *Scientific American*, 262:40). In the cell, the antisense nucleic acids hybridize to the corresponding mRNA, forming a double-stranded molecule. The antisense nucleic acids interfere with the translation of the mRNA, since the cell will not translate a mRNA that is double-stranded. Antisense oligomers of about 15 nucleotides are preferred, since they are easily synthesized and are less likely to cause problems than larger molecules when introduced into the target cell. The use of antisense methods to inhibit the in vitro translation of genes is well known in the art (Marcus-Sakura, 1988, *Anal. Biochem.*, 172:289).

Use of an oligonucleotide to stall transcription is known as the triplex strategy since the oligomer winds around double-helical DNA, forming a three-strand helix. Therefore, these triplex compounds can be designed to recognize a unique site on a chosen gene (Maher, et al., 1991, *Antisense Res. and Dev.*, 1(3):227; Helene, C., 1991, *Anticancer Drug Design*, 6:569).

Ribozymes are RNA molecules possessing the ability to specifically cleave other single-stranded RNA in a manner analogous to DNA restriction endonucleases. Through the modification of nucleotide sequences which encode these RNAs, it is possible to engineer molecules that recognize specific nucleotide sequences in an RNA molecule and cleave it (Cech, 1988, *J. Amer. Med. Assn.*, 260:3030). A major advantage of this approach is that, because they are sequence-specific, only mRNAs with particular sequences are inactivated.

There are two basic types of ribozymes namely, tetrahymena-type (Hasselhoff, 1988, *Nature*, 334:585) and "hammerhead"-type. Tetrahymena-type ribozymes recognize sequences which are four bases in length, while "hammerhead"-type ribozymes recognize base sequences 11–18 bases in length. The longer the recognition sequence, the greater the likelihood that the sequence will occur exclusively in the target mRNA species. Consequently, hammerhead-type ribozymes are preferable to tetrahymena-type ribozymes for inactivating a specific mRNA species and 18-based recognition sequences are preferable to shorter recognition sequences.

When a disorder is associated with the decreased expression of Glutamate Transporter Associated Protein, nucleic acid sequences that encode Glutamate Transporter Associated Protein can be used. An agent which modulates Glutamate Transporter Associated Protein expression includes a polynucleotide encoding a polypeptide of SEQ ID NO:2, SEQ ID NO:4, SEQ ID NO:6, SEQ ID NO:8, SEQ ID NO:22, or a conservative variant thereof. Alternatively, an agent of use with the subject invention includes agents that increase the expression of a polynucleotide encoding Glutamate Transporter Associated Protein or an agent that increases the activity of Glutamate Transporter Associated Protein polypeptide.

In another series of embodiments, the present invention provides transgenic animal models diseases or disorders associated with mutations in the Glutamate Transporter Associated Protein genes. The animal may be essentially any amphibian, reptile, fish, mammal, and the like. Preferably, the transgenic animal is mammalian including rats, mice, hamsters, guinea pigs, rabbits, dogs, cats, goats, sheep, pigs, and non-human primates. In addition, invertebrate models, including nematodes and insects, may be used for certain applications. The animal models are produced by standard transgenic methods including microinjection, transfection, or by other forms of transformation of embryonic stem cells, zygotes, gametes, and germ line cells with vectors including genomic or cDNA fragments, minigenes, homologous recombination vectors, viral insertion vectors and the like. Suitable vectors include vaccinia virus, adenovirus, adeno associated virus, retrovirus, liposome transport, neuraltropic viruses, Herpes simplex virus, and the like. The animal models may include transgenic sequences comprising or derived from Glutamate Transporter Associated Proteins including normal and mutant sequences, intronic, exonic and untranslated sequences, and sequences encoding subsets of Glutamate Transporter Associated Protein such as functional domains.

The major types of animal models provided include: (1) Animals in which a normal human Glutamate Transporter Associated Protein gene has been recombinantly introduced into the genome of the animal as an additional gene, under the regulation of either an exogenous or an endogenous promoter element, and as either a minigene or a large genomic fragment; in which a normal human Glutamate Transporter Associated Protein gene has been recombinantly substituted for one or both copies of the animal's homologous Glutamate Transporter Associated Protein gene by homologous recombination or gene targeting; and/or in which one or both copies of one of the animal's homologous Glutamate Transporter Associated Protein genes have been recombinantly "humanized" by the partial substitution of sequences encoding the human homologue by homologous recombination or gene targeting. (2) Animals in which a mutant human Glutamate Transporter Associated Protein gene has been recombinantly introduced into the genome of the animal as an additional gene, under the regulation of either an exogenous or an endogenous promoter element, and as either a minigene or a large genomic fragment; in which a mutant human Glutamate Transporter Associated Protein gene has been recombinantly substituted for one or both copies of the animal's homologous Glutamate Transporter Associated Protein gene by homologous recombination or gene targeting; and/or in which one or both copies of one of the animal's homologous Glutamate Transporter Associated Protein genes have been recombinantly "humanized" by the partial substitution of sequences encoding a mutant human homologue by homologous recombination or gene targeting. (3) Animals in which a mutant version of one of that animal's Glutamate Transporter Associated Protein genes has been recombinantly introduced into the genome of the animal as an additional gene, under the regulation of either an exogenous or an endogenous promoter element, and as either a minigene or a large genomic fragment; and/or in which a mutant version of one of that animal's Glutamate Transporter Associated Protein genes has been recombinantly substituted for one or both copies of the animal's homologous Glutamate Transporter Associated Protein gene by homologous recombination or gene targeting. (4) "Knock-out" animals in which one or both copies of one of the animal's Glutamate Transporter Associated Protein genes have been partially or completely deleted by homologous recombination or gene targeting, or have been inactivated by the insertion or substitution by homologous recombination or gene targeting of exogenous sequences.

In a preferred embodiment of the invention, there is provided a transgenic non-human animal having a transgene that expresses a Glutamate Transporter Associated Protein-encoding polynucleotide chromosomally integrated into the germ cells of the animal. Animals are referred to as "transgenic" when such animal has had a heterologous DNA sequence, or one or more additional DNA sequences normally endogenous to the animal (collectively referred to herein as "transgenes") chromosomally integrated into the germ cells of the animal. The transgenic animal (including its progeny) will also have the transgene fortuitously integrated into the chromosomes of somatic cells.

Various methods to make the transgenic animals of the subject invention can be employed. Generally speaking, three such methods may be employed. In one such method, an embryo at the pronuclear stage (a "one cell embryo") is harvested from a female and the transgene is microinjected into the embryo, in which case the transgene will be chromosomally integrated into both the germ cells and somatic cells of the resulting mature animal. In another such method, embryonic stem cells are isolated and the transgene incorporated therein by electroporation, plasmid transfection or microinjection, followed by reintroduction of the stem cells into the embryo where they colonize and contribute to the germ line. Methods for microinjection of mammalian species is described in U.S. Pat. No. 4,873,191. In yet another such method, embryonic cells are infected with a retrovirus containing the transgene whereby the germ cells of the embryo have the transgene chromosomally integrated therein. When the animals to be made transgenic are avian, because avian fertilized ova generally go through cell division for the first twenty hours in the oviduct, microinjection into the pronucleus of the fertilized egg is problematic due to the inaccessibility of the pronucleus. Therefore, of the methods to make transgenic animals described generally above, retrovirus infection is preferred for avian species, for example as described in U.S. Pat. No. 5,162,215. If microinjection is to be used with avian species, however, a recently published procedure by Love et al., (Biotechnology, 12, Jan. 1994) can be utilized whereby the embryo is obtained from a sacrificed hen approximately two and one-half h after the laying of the previous laid egg, the transgene is microinjected into the cytoplasm of the germinal disc and the embryo is cultured in a host shell until maturity. When the animals to be made transgenic are bovine or porcine, microinjection can be hampered by the opacity of the ova thereby making the nuclei difficult to identify by traditional differential interference-contrast microscopy. To overcome this problem, the ova can first be centrifuged to segregate the pronuclei for better visualization.

The non-human animals of the invention are murine typically (e.g., mouse). The transgenic non-human animals of the invention are produced by introducing "transgenes" into the germline of the non-human animal. Embryonal target cells at various developmental stages can be used to introduce transgenes. Different methods are used depending on the stage of development of the embryonal target cell. The zygote is the best target for microinjection. The use of zygotes as a target for gene transfer has a major advantage in that in most cases the injected DNA will be incorporated into the host gene before the first cleavage (Brinster et al., Proc. Natl. Acad. Sci. USA 82:4438–4442, 1985). As a consequence, all cells of the transgenic non-human animal will carry the incorporated transgene. This will in general also be reflected in the efficient transmission of the transgene to offspring of the founder since 50% of the germ cells will harbor the transgene.

The term "transgenic" is used to describe an animal which includes exogenous genetic material within all of its cells. A "transgenic" animal can be produced by cross-breeding two chimeric animals which include exogenous genetic material within cells used in reproduction. Twenty-five percent of the resulting offspring will be transgenic i.e., animals which include the exogenous genetic material within all of their cells in both alleles. Fifty percent of the resulting animals will include the exogenous genetic material within one allele and twenty five percent will include no exogenous genetic material.

In the microinjection method useful in the practice of the subject invention, the transgene is digested and purified free from any vector DNA e.g. by gel electrophoresis. It is preferred that the transgene include an operatively associated promoter which interacts with cellular proteins involved in transcription, ultimately resulting in constitutive expression. Promoters useful in this regard include those from cytomegalovirus (CMV), Moloney leukemia virus (MLV), and herpes virus, as well as those from the genes encoding metallothionine, skeletal actin, P-enolpyruvate carboxylase (PEPCK), phosphoglycerate (PGK), DHFR, and thymidine kinase. Promoters for viral long terminal repeats (LTRs) such as Rous Sarcoma Virus can also be employed. Constructs useful in plasmid transfection of embryonic stem cells will employ additional regulatory elements well known in the art such as enhancer elements to stimulate transcription, splice acceptors, termination and polyadenylation signals, and ribosome binding sites to permit translation.

Retroviral infection can also be used to introduce transgene into a non-human animal, as described above. The developing non-human embryo can be cultured in vitro to the blastocyst stage. During this time, the blastomeres can be targets for retro viral infection (Jaenich, R., Proc. Natl. Acad. Sci USA 73:1260–1264, 1976). Efficient infection of the blastomeres is obtained by enzymatic treatment to remove the zona pellucida (Hogan, et al. (1986) in Manipulating the Mouse Embryo, Cold Spring Harbor Laboratory Press, Cold Spring Harbor, N.Y.). The viral vector system used to introduce the transgene is typically a replication-defective retro virus carrying the transgene (Jahner, et al., *Proc. Natl.*

*Acad. Sci. USA* 82:6927–6931, 1985; Van der Putten, et al., *Proc. Natl. Acad. Sci USA* 82:6148–6152, 1985). Transfection is easily and efficiently obtained by culturing the blastomeres on a monolayer of virus-producing cells (Van der Putten, supra; Stewart, et al., *EMBO J*. 6:383–388, 1987). Alternatively, infection can be performed at a later stage. Virus or virus-producing cells can be injected into the blastocoel (D. Jahner et al., *Nature* 2–98:623–628, 1982). Most of the founders will be mosaic for the transgene since incorporation occurs only in a subset of the cells which formed the transgenic nonhuman animal. Further, the founder may contain various retro viral insertions of the transgene at different positions in the genome which generally will segregate in the offspring. In addition, it is also possible to introduce transgenes into the germ line, albeit with low efficiency, by intrauterine retroviral infection of the midgestation embryo (D. Jahner et al., supra).

A third type of target cell for transgene introduction is the embryonal stem cell (ES). ES cells are obtained from pre-implantation embryos cultured in vitro and fused with embryos (M. J. Evans et al. *Nature* 292:154–156, 1981; M. O. Bradley et al., *Nature* 309:255–258, 1984; Gossler, et al., *Proc. Natl. Acad. Sci USA* 83: 9065–9069, 1986; and Robertson et al., *Nature* 322:445–448, 1986). Transgenes can be efficiently introduced into the ES cells by DNA transfection or by retro virus-mediated transduction. Such transformed ES cells can thereafter be combined with blastocysts from a nonhuman animal. The ES cells thereafter colonize the embryo and contribute to the germ line of the resulting chimeric animal. (For review see Jaenisch, R., *Science* 240: 1468–1474, 1988).

"Transformed" means a cell into which (or into an ancestor of which) has been introduced, by means of recombinant nucleic acid techniques, a heterologous nucleic acid molecule. "Heterologous" refers to a nucleic acid sequence that either originates from another species or is modified from either its original form or the form primarily expressed in the cell.

"Transgene" means any piece of DNA which is inserted by artifice into a cell, and becomes part of the genome of the organism (i.e., either stably integrated or as a stable extrachromosomal element) which develops from that cell. Such a transgene may include a gene which is partly or entirely heterologous (i.e., foreign) to the transgenic organism, or may represent a gene homologous to an endogenous gene of the organism. Included within this definition is a transgene created by the providing of an RNA sequence which is transcribed into DNA and then incorporated into the genome. The transgenes of the invention include DNA sequences which encode Glutamate Transporter Associated Protein polypeptide-sense and antisense polynucleotides, which may be expressed in a transgenic non-human animal. The term "transgenic" as used herein additionally includes any organism whose genome has been altered by in vitro manipulation of the early embryo or fertilized egg or by any transgenic technology to induce a specific gene knockout. As used herein, the term "transgenic" includes any transgenic technology familiar to those in the art which can produce an organism carrying an introduced transgene or one in which an endogenous gene has been rendered non-functional or "knocked out".

Another embodiment of the invention provides a computer readable medium having store thereon a nucleic acid sequence selected from the group consisting of SEQ ID NO:1, SEQ ID NO:3, SEQ ID NO:5, SEQ ID NO:7 and sequences substantially identical thereto, or a polypeptide sequence selected from the group consisting of SEQ ID NO:2, SEQ ID NO:4, SEQ ID NO:6, SEQ ID NO:8, SEQ ID NO:22 and sequences substantially identical thereto.

A further embodiment of the invention provides a computer system comprising a processor and a data storage device wherein said date storage device has stored thereon a nucleic acid sequence selected from the group consisting of SEQ ID NO:1, SEQ ID NO:3, SEQ ID NO:5, SEQ ID NO:7 and sequences substantially identical thereto, or a polypeptide sequence selected from the group consisting of SEQ ID NO:2, SEQ ID NO:4, SEQ ID NO:6, SEQ ID NO:8, SEQ ID NO:22 and sequences substantially identical thereto. The computer system, additionally can contain a sequence comparison algorithm and a data storage device having at least one reference sequence stored on it. The sequence comparison algorithm comprises a computer program which indicates polymorphisms. The term "polymorphism", as used herein, refers to the existence of multiple alleles at a single locus. Polymorphism can be are several types including, for example, those that change DNA sequence but do not change protein sequence, those that change protein sequence without changing function, those that create proteins with a different activity, and those that create proteins that are non-functional.

Figure 10:
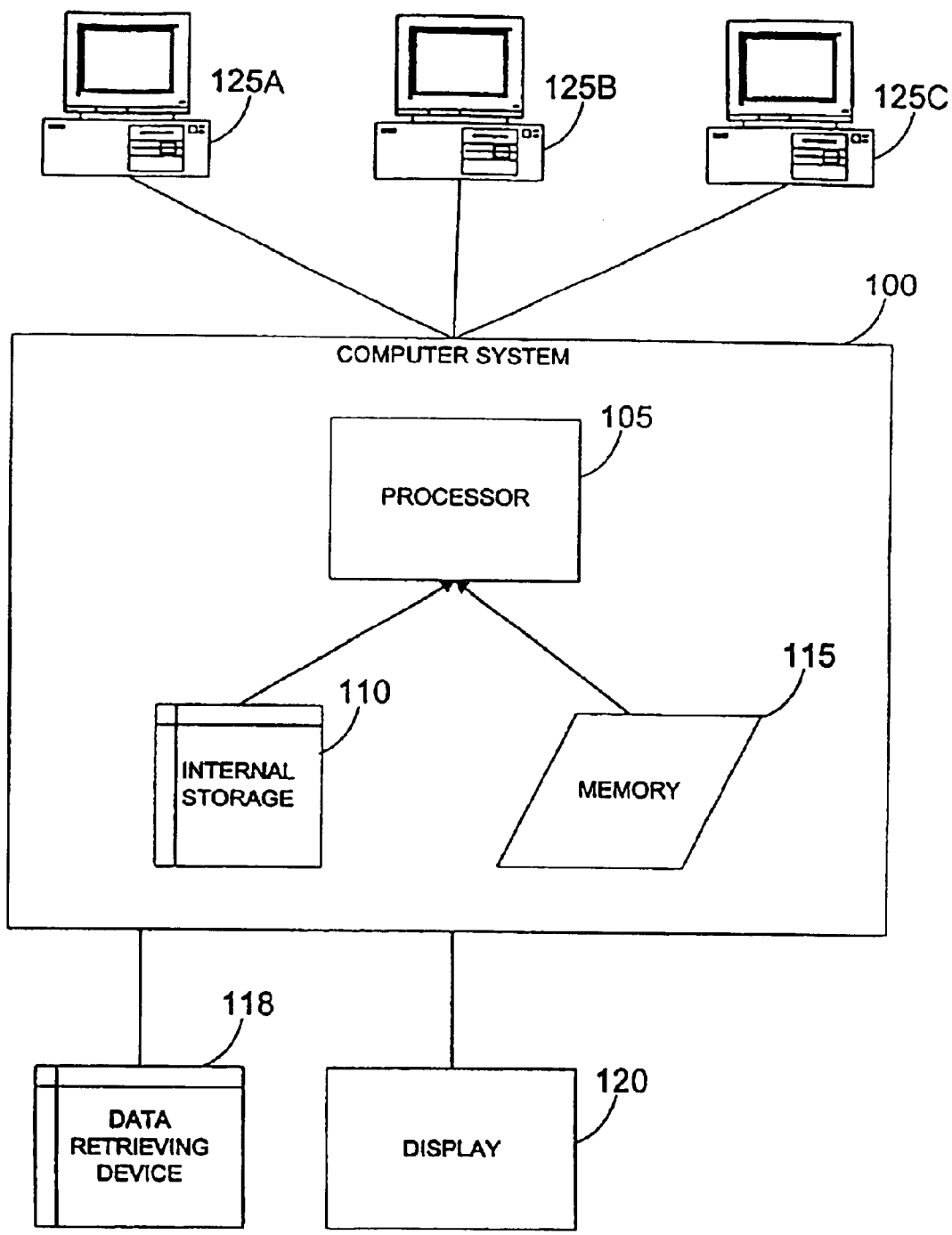
FIG. 10 is a flow diagram illustrating a computer system, data retrieving device and display.

Embodiments of the invention include systems (e.g., internet based systems), particularly computer systems which store and manipulate the coordinate and sequence information described herein. One example of a computer system 100 is illustrated in block diagram form in FIG. 10. As used herein, "a computer system" refers to the hardware components, software components, and data storage components used to analyze the coordinates and sequences as set forth herein. The computer system 100 typically includes a processor for processing, accessing and manipulating the sequence data. The processor 105 can be any well-known type of central processing unit, such as, for example, the Pentium III from Intel Corporation, or similar processor from Sun, Motorola, Compaq, AMD or International Business Machines.

Typically the computer system 100 is a general purpose system that comprises the processor 105 and one or more internal data storage components 110 for storing data, and one or more data retrieving devices for retrieving the data stored on the data storage components. A skilled artisan can readily appreciate that any one of the currently available computer systems are suitable.

In one particular embodiment, the computer system 100 includes a processor 105 connected to a bus which is connected to a main memory 115 (preferably implemented as RAM) and one or more internal data storage devices 110, such as a hard drive and/or other computer readable media having data recorded thereon. In some embodiments, the computer system 100 further includes one or more data retrieving device 118 for reading the data stored on the internal data storage devices 110.

The data retrieving device 118 may represent, for example, a floppy disk drive, a compact disk drive, a magnetic tape drive, or a modem capable of connection to a remote data storage system (e.g., via the internet) etc. In some embodiments, the internal data storage device 110 is a removable computer readable medium such as a floppy disk, a compact disk, a magnetic tape, etc. containing control logic and/or data recorded thereon. The computer system 100 may advantageously include or be programmed by appropriate software for reading the control logic and/or the data from the data storage component once inserted in the data retrieving device.

The computer system 100 includes a display 120 which is used to display output to a computer user. It should also be noted that the computer system 100 can be linked to other computer systems 125*a–c* in a network or wide area network to provide centralized access to the computer system 100.

Figure 11:
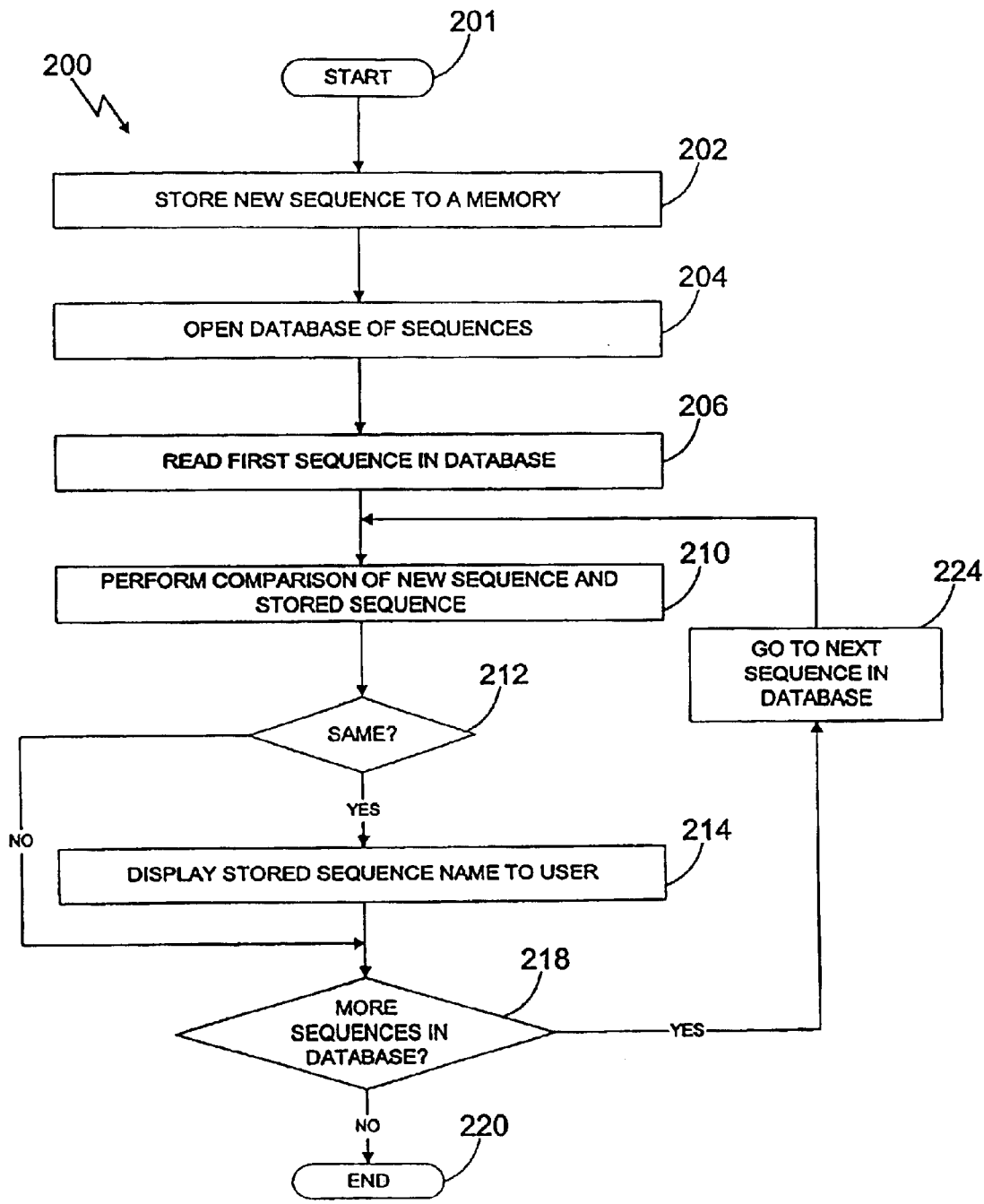
FIG. 11 is a flow diagram illustrating one embodiment of process 200 for comparing a new nucleotide or protein sequence with a database of sequences in order to determine the homology levels between the new sequence and the sequences in the database.

FIG. 11 is a flow diagram illustrating one embodiment of a process 200 for comparing a new nucleotide or protein sequence with a database of sequences in order to determine the homology levels between the new sequence and the sequences in the database. The database of sequences can be a private database stored within the computer system 100, or a public database such as GENBANK that is available through the Internet.

The process 200 begins at a start state 201 and then moves to a state 202 wherein the new sequence to be compared is stored to a memory in a computer system 100. As discussed above, the memory could be any type of memory, including RAM or an internal storage device.

The process 200 then moves to a state 204 wherein a database of sequences is opened for analysis and comparison. The process 200 then moves to a state 206 wherein the first sequence stored in the database is read into a memory on the computer. A comparison is then performed at a state 210 to determine if the first sequence is the same as the second sequence. It is important to note that this step is not limited to performing an exact comparison between the new sequence and the first sequence in the database. Well-known methods are known to those of skill in the art for comparing two nucleotide or protein sequences, even if they are not identical. For example, gaps can be introduced into one sequence in order to raise the homology level between the two tested sequences. The parameters that control whether gaps or other features are introduced into a sequence during comparison are normally entered by the user of the computer system.

Once a comparison of the two sequences has been performed at the state 210, a determination is made at a decision state 210 whether the two sequences are the same. Of course, the term "same" is not limited to sequences that are absolutely identical. Sequences that are within the homology parameters entered by the user will be marked as "same" in the process 200.

If a determination is made that the two sequences are the same, the process 200 moves to a state 214 wherein the name of the sequence from the database is displayed to the user. This state notifies the user that the sequence with the displayed name fulfills the homology constraints that were entered. Once the name of the stored sequence is displayed to the user, the process 200 moves to a decision state 218 wherein a determination is made whether more sequences exist in the database. If no more sequences exist in the database, then the process 200 terminates at an end state 220 However, if more sequences do exist in the database, then the process 200 moves to a state 224 wherein a pointer is moved to the next sequence in the database so that it can be compared to the new sequence. In this manner, the new sequence is aligned and compared with every sequence in the database.

It should be noted that if a determination had been made at the decision state 212 that the sequences were not homologous, then the process 200 would move immediately to the decision state 218 in order to determine if any other sequences were available in the database for comparison.

Figure 12:
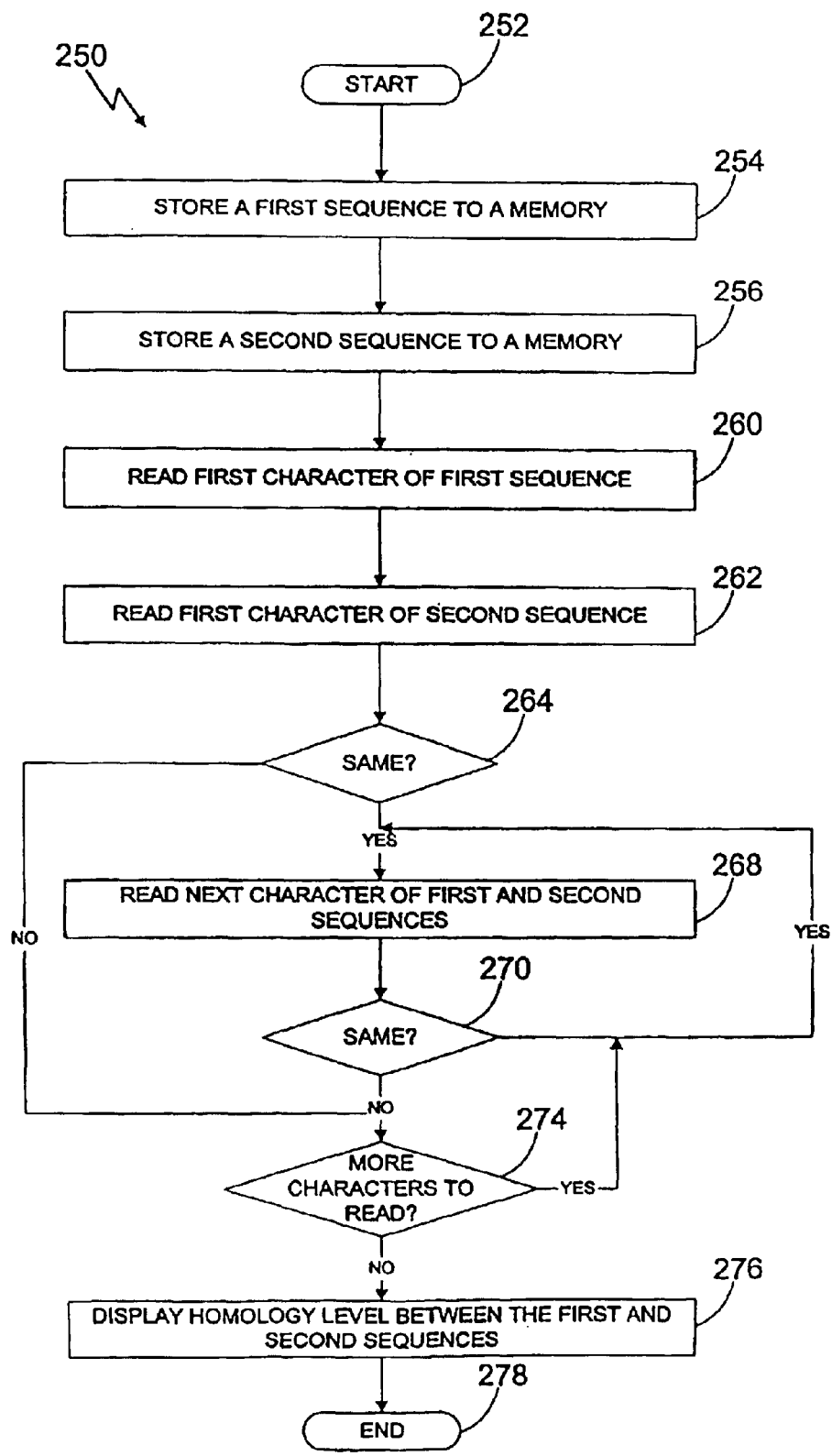
FIG. 12 is a flow diagram illustrating one embodiment of a process 250 in a computer for determining whether two sequences are homologous.

FIG. 12 is a flow diagram illustrating one embodiment of a process 250 in a computer for determining whether two sequences are homologous. The process 250 begins at a start state 252 and then moves to a state 254 wherein a first sequence to be compared is stored to a memory. The second sequence to be compared is then stored to a memory at a state 256. The process 250 then moves to a state 260 wherein the first character in the first sequence is read and then to a state 262 wherein the first character of the second sequence is read. It should be understood that if the sequence is a nucleotide sequence, then the character would normally be either A, T, C, G or U. If the sequence is a protein sequence, then it is preferably in the single letter amino acid code so that the first and sequence sequences can be easily compared.

A determination is then made at a decision state 264 whether the two characters are the same. If they are the same, then the process 250 moves to a state 268 wherein the next characters in the first and second sequences are read. A determination is then made whether the next characters are the same. If they are, then the process 250 continues this loop until two characters are not the same. If a determination is made that the next two characters are not the same, the process 250 moves to a decision state 274 to determine whether there are any more characters either sequence to read.

If there are not any more characters to read, then the process 250 moves to a state 276 wherein the level of homology between the first and second sequences is displayed to the user. The level of homology is determined by calculating the proportion of characters between the sequences that were the same out of the total number of sequences in the first sequence. Thus, if every character in a first 100 nucleotide sequence aligned with a every character in a second sequence, the homology level would be 100%.

Homology or identity is often measured using sequence analysis software (e.g., Sequence Analysis Software Package of the Genetics Computer Group, University of Wisconsin Biotechnology Center, 1710 University Avenue, Madison, Wis. 53705). Such software matches similar sequences by assigning degrees of homology to various deletions, substitutions and other modifications. The terms "homology" and "identity" in the context of two or more nucleic acids or polypeptide sequences, refer to two or more sequences or subsequences that are the same or have a specified percentage of amino acid residues or nucleotides that are the same when compared and aligned for maximum correspondence over a comparison window or designated region as measured using any number of sequence comparison algorithms or by manual alignment and visual inspection.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequence for comparison are well-known in the art. Optimal alignment of sequences for comparison can be conducted, e.g., by the local homology algorithm of Smith & Waterman, Adv. Appl. Math. 2:482, 1981, by the homology alignment algorithm of Needleman & Wunsch, J. Mol. Biol. 48:443, 1970, by the search for similarity method of person & Lipman, Proc. Nat'l. Acad. Sci. USA 85:2444, 1988, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection. Other algorithms for determining homology or identity include, for example, in addition to a BLAST program (Basic Local Alignment Search Tool at the National Center for Biological Information), ALIGN, AMAS (Analysis of Multiply Aligned Sequences), AMPS (Protein Multiple Sequence Alignment), ASSET (Aligned Segment Statistical Evaluation Tool), BANDS, BESTSCOR, BIOSCAN (Biological Sequence Comparative Analysis Node), BLIMPS (BLocks IMProved Searcher), FASTA, Intervals & Points, BMB, CLUSTAL V, CLUSTAL W, CONSENSUS, LCONSENSUS, WCONSENSUS, Smith-Waterman algorithm, DARWIN, Las Vegas algorithm, FNAT (Forced Nucleotide Alignment Tool), Framealign, Framesearch, DYNAMIC, FILTER, FSAP (Fristensky Sequence Analysis Package), GAP (Global Alignment Program), GENAL, GIBBS, GenQuest, ISSC (Sensitive Sequence Comparison), LALIGN (Local Sequence Alignment), LCP (Local Content Program), MACAW (Multiple Alignment Construction & Analysis Workbench), MAP (Multiple Alignment Program), MBLKP, MBLKN, PMA (Pattern-Induced Multi-sequence Alignment), SAGA (Sequence Alignment by Genetic Algorithm) and WHAT-IF. Such alignment programs can also be used to screen genome databases to identify polynucleotide sequences having substantially identical sequences. A number of genome databases are available, for example, a substantial portion of the human genome is available as part of the Human Genome Sequencing Project (Gibbs, 1995). At least twenty-one other genomes have already been sequenced, including, for example, *M. genitalium* (Fraser et al., 1995), *M. jannaschii* (Bult et al., 1996), *H. influenzae* (Fleischmann et al., 1995), *E. coli* (Blattner et al., 1997), and yeast (*S. cerevisiae*) (Mewes et al., 1997), and *D. melanogaster* (Adams et al., 2000). Significant progress has also been made in sequencing the genomes of model organism, such as mouse, *C. elegans*, and Arabadopsis sp. Several databases containing genomic information annotated with some functional information are maintained by different organization, and are accessible via the internet, for example, see the databases available on the world wide web at the web sites for The Institute for Genomic Research, The University of Wisconsin, at Stanford University, The National Center for Biotechnology Information (NCBI), The European Bioinforatics Institute, The Institute Pasteur, The Whitehead Institute of the Massachusetts Institute of Technology, and the HIV Databases at the Los Alamos National Laboratory web site.

One example of a useful algorithm is BLAST and BLAST 2.0 algorithms, which are described in Altschul et al., Nuc. Acids Res. 25:3389–3402, 1977, and Altschul et al., J. Mol. Biol. 215:403–410, 1990, respectively. Software for performing BLAST analyses is publicly available through the National Center for Biotechnology Information world wide web site. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) of 10, M=5, N=−4 and a comparison of both strands. For amino acid sequences, the BLASTP program uses as defaults a word length of 3, and expectations (E) of 10, and the BLOSUM62 scoring matrix (see Henikoff & Henikoff, Proc. Natl. Acad. Sci. USA 89:10915, 1989) alignments (B) of 50, expectation (E) of 10, M=5, N=−4, and a comparison of both strands.

The BLAST algorithm also performs a statistical analysis of the similarity between two sequences (see, e.g., Karlin & Altschul, Proc. Natl. Acad. Sci. USA 90:5873, 1993). One measure of similarity provided by BLAST algorithm is the smallest sum probability (P(N)), which provides an indication of the probability by which a match between two nucleotide or amino acid sequences would occur by chance. For example, a nucleic acid is considered similar to a references sequence if the smallest sum probability in a comparison of the test nucleic acid to the reference nucleic acid is less than about 0.2, more preferably less than about 0.01, and most preferably less than about 0.001.

In one embodiment, protein and nucleic acid sequence homologies are evaluated using the Basic Local Alignment Search Tool ("BLAST") In particular, five specific BLAST programs are used to perform the following task:

(1) BLASTP and BLAST3 compare an amino acid query sequence against a protein sequence database;

(2) BLASTN compares a nucleotide query sequence against a nucleotide sequence database;

(3) BLASTX compares the six-frame conceptual translation products of a query nucleotide sequence (both strands) against a protein sequence database;

(4) TBLASTN compares a query protein sequence against a nucleotide sequence database translated in all six reading frames (both strands); and (5) TBLASTX compares the six-frame translations of a nucleotide query sequence against the six-frame translations of a nucleotide sequence database.

The BLAST programs identify homologous sequences by identifying similar segments, which are referred to herein as "high-scoring segment pairs," between a query amino or nucleic acid sequence and a test sequence which is preferably obtained from a protein or nucleic acid sequence database. High-scoring segment pairs are preferably identified (i.e., aligned) by means of a scoring matrix, many of which are known in the art. Preferably, the scoring matrix used is the BLOSUM62 matrix (Gonnet et al., Science 256:1443–1445, 1992; Henikoff and Henikoff, Proteins 17:49–61, 1993). Less preferably, the PAM or PAM250 matrices may also be used (see, e.g., Schwartz and Dayhoff, eds., 1978, *Matrices for Detecting Distance Relationships: Atlas of Protein Sequence and Structure*, Washington: National Biomedical Research Foundation). BLAST programs are accessible through the U.S. National Library of Medicine, e.g., at The National Center for Biotechnology Information web site.

The parameters used with the above algorithms may be adapted depending on the sequence length and degree of homology studied. In some embodiments, the parameters may be the default parameters used by the algorithms in the absence of instructions from the user.

Figure 13:
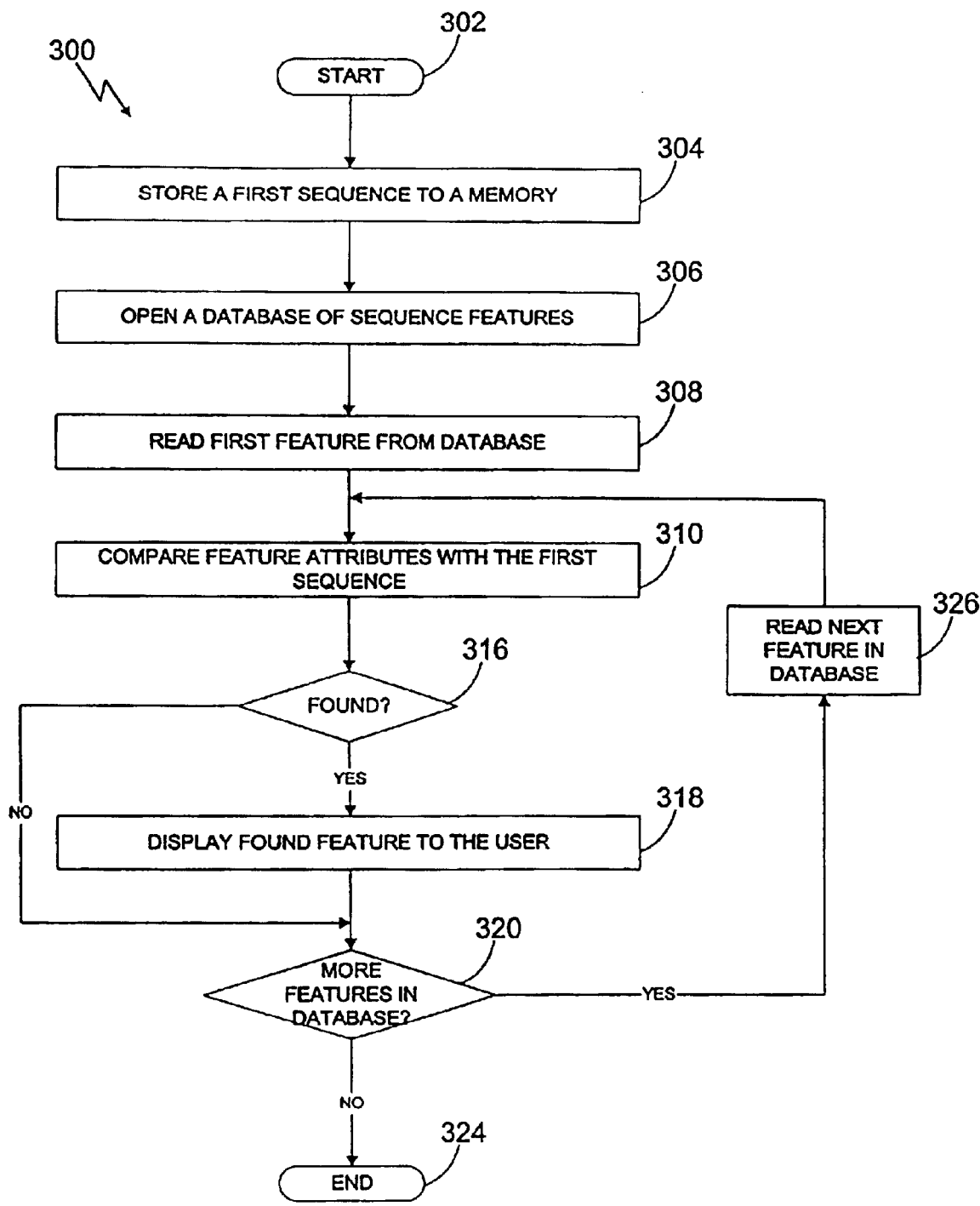
FIG. 13 is a flow diagram illustrating one embodiment of a process 300 for comparing features in polynucleotide and polypeptide sequences.

FIG. 13 is a flow diagram illustrating one embodiment of an identifier process 300 for detecting the presence of a feature in a sequence. The process 300 begins at a start state 302 and then moves to a state 304 wherein a first sequence that is to be checked for features is stored to a memory 115 in the computer system 100. The process 300 then moves to a state 306 wherein a database of sequence features is opened. Such a database would include a list of each feature's attributes along with the name of the feature. For example, a feature name could be "Initiation Codon" and the attribute would be "ATG". Another example would be the feature name "TAATAA Box" and the feature attribute would be "TAATAA". An example of such a database is produced by the University of Wisconsin Genetics Computer Group (GCG) and available at the GCG world wide web site. Alternatively, the features may be structural polypeptide motifs such as alpha helices, beta sheets, or functional polypeptide motifs such as enzymatic active sites, helix-turn-helix motifs or other motifs known to those skilled in the art.

The following examples are intended to illustrate, but not limit, the invention.

EXAMPLE 1

Identification of Proteins Interacting with Glutamate Transporter Proteins

Yeast Two-Hybrid with EAAT4 Yeast two-hybrid screens were performed using the HF7c' yeast strain harboring the reporter genes HIS 3 and β-galactosidase (β-gal) under the control of GAL4 activation. The final 77 amino acids of EAAT4 (carboxy-intracellular domain SEQ ID NO:12) were subcloned in-frame into pGBT9 (GAL4 binding domain vector, CLONTECH) and used to screen a rat brain cDNA library constructed in pGAD10 (GAL4 activation domain vector, CLONTECH). The plasmids were transforrned into HF7c' yeast cells and positive clones selected on triple-minus plates (Leu–, Trp–, His–) and assayed for β-galactosidase activity. Positive clones were co-transformed with either the bait vector or the original pGAD10 vector into yeast cells to confirm the interaction. For a subsequent EAAT4 C-terminal domain analysis, different regions of the final 77 amino acids of EAAT4 were subcloned in-frame into the pGBT9 vector.

Yeast Two-Hybrid Screen with EAAC1 The MATCH-MAKER Two-Hybrid System (Clontech) was used for screening. Using the carboxy-terminal intracellular domain of EAAC1 (the carboxy-87 amino acids, cDNA position 1458–1719; SEQ ID NO:13) as bait in a yeast two-hybrid screen of an adult rat brain cDNA library, 78 clones displaying β-galactosidase activity were identified. Plasmid DNAs were isolated from positive clones and re-cotransforrned with bait cDNA back into yeast to reconfirm the interaction. Restriction and sequencing analyses revealed that ten of these clones with the strongest β-galactosidase activity were identical.

EXAMPLE 2

Isolation and Primary Structure of Glutamate Transporter Associated Proteins

Cloning of full-length GTRAP4-41 and GTRAP4-48 cDNAs. Marathon cDNA amplification (CLONTECH) was used to perform both 5'- and 3'-RACE on cDNA synthesized from rat brain poly(A)$^+$ RNA. The double-stranded cDNA was ligated to the Marathon cDNA Adaptor which contains an adaptor primer (AP1) binding site. The 1.1 kb GTRAP4-41 and 1.4 kb GTRAP4-48 cDNA fragments identified using the yeast two-hybrid system were used to design gene-specific primers (GSPs) which could be used in 5'- and 3'-RACE PCR reactions along with the AP1 primer. The RACE products obtained were sequenced and new GSPs designed, generating a series of overlapping RACE products, which were joined together by PCR. Overlapping RACE products were put through ten cycles of denaturation, annealing and extension in the absence of primers. Nested primers were added and the PCR continued for a further 20 cycles to amplify the overlapped template.

GTRAP4-41 AND 4-48 Two independent cDNA clones were isolated and the proteins they encode were named GTRAP4-41 and GTRAP4-48 (for glutamate transporter 4 associated protein). Isolation of the full-length cDNAs by a series of 5' and 3' RACE PCR reactions demonstrated that the largest open reading frame (ORF) for GTRAP4-41 is 7,164 base pairs (SEQ ID NO:1), which encodes a 2,388 amino acid protein (SEQ ID NO:2) with a predicted relative molecular mass ($M_r$) of 270,958 Da (accession AF225960). A BLAST search of the GenBank database shows that GTRAP4-41 possesses 87% identity with β-spectrin III (accession AB008567). GTRAP4-41 possesses seventeen 16 amino acid spectrin repeats, two α-actinin domains and a pleckstrin homology domain (FIG. 1A).

The largest ORF identified for GTRAP4-48 (accession AF225961) is 4,581 base pairs (SEQ ID NO:3), which encodes a 1,527 amino acid protein (SEQ ID NO:4) with a predicted $M_r$ of 168,698 Da. A BLAST search of the GenBank database shows that GTRAP4-48 is unique, but it possesses significant homology to the KIAA0380 cDNA-encoded protein (90% identity) and the recently described RhoGEF, p115. GTRAP4-48 posses multiple potential interaction and regulatory domains (FIG. 1D). GTRAP4-48 has a PDZ domain, a regulatory G-protein domain, a pleckstrin homology region (PH) and two proline-rich sequences (PRO). These regions have all been implicated in protein-protein interactions by interacting with the C termini of proteins and are thought to be important in the subcellular targeting of the interacting proteins (Katan et al., FEBS Lett. (1999) 452:36–40; LeVine Mol. Neurobiol. (1999); 19:111–149). The function of PH domain is not clearly clarified, several putative functions have been suggested; (1) binding to the β/γ subunit of heterotrimeric G proteins, (2) binding to lipids, (3) binding to phosphorylated Ser/Thr residues, (4) attachment to membrane by an unknown mechanism. The protein multiple PKC phosphorylation sites and one tyrosine kinase phosphorylation site. It contains 3 helix-loop-helix signatures. Finally, the protein contains a separated tandem periodic repeat of SQPEGS of undermined significance.

GTRAP3-18. Following isolation, one clone, E18, was completely sequenced and the protein encoded is named GTRAP3-18 (glutamate transporter EAAC1 associated protein). Clone E18 is a full-length cDNA containing initiation methionine and polyA tail (SEQ ID NO:5). GTRAP3-18 encodes a protein of 188 amino acids (SEQ ID NO:6) with a calculated molecular mass of 22.5 kDa. Protein analysis indicates that it is a very hydrophobic protein with four possible transmembrane domains. Both the carboxy-terminal and amino-terminal domains contain protein kinase C motifs and may be intracellular. JWA protein (Genbank NP006398), a novel human differentially displayed vitamin A responsive gene, is 95% identical to GTRAP3-18, suggesting that GTRAP3-18 is a rat JWA protein homologue.

EXAMPLE 3

Antibodies

Generation of Polyclonal GTRAP4-41 and GTRAP4-48 Antibodies

Affinity purified polyclonal antisera to EAAT4, GTRAP4-41 and GTRAP4-48 were produced using methods identical to previous studies (Rothstein et al., Neuron (1994) 13:713–725. Synthetic peptides corresponding to epitopes of EAAT4 (carboxy-terminal; EKGASRGRGGNESA; SEQ ID NO:14 and amino-terminal; KNSLFLRESGAGGGCL; SEQ ID NO:15), rat GTRAP4-41 (KRGPAPSPMPQSRSSE; SEQ ID NO:16) and rat GTRAP4-48 (KTPERTSPSHHRQPSD; SEQ ID NO:17) were synthesized. Monospecific antibodies to GTRAP4-41 and 4-48 were produced.

The affinity-purified GTRAP4-41 antibodies recognize a 270 KDa protein in HEK 293T cells transfected with the full-length GTRAP4-41 cDNA and the affinity-purified GTRAP4-48 antibodies recognized a 170 KDa protein in HEK 293T cells transfected with the full-length GTRAP4-48 cDNA Generation of Polyclonal GTRAP3-18 Antibodies. Affinity purified polyclonal antisera to GTRAP3-18 was produced as described in Rothstein et al. (1994) using the amino terminal region epitope, (KFFPGSDRFARPDFR SEQ ID NO:18).

EXAMPLE 4

Expression of Glutamate Transporter Associated Proteins

Fusion proteins and in vitro binding. Full-length EAAT4 was subcloned into the EcoR I site of the GST-fusion vector pGEX-6P-1 (Pharmacia). Synthesis of recombinant proteins in BL21 cells (Novagen) was induced by 0.1 mM isopropyl β-D-thiogalactoside for 2 hrs at 30° C. and purified according to the protocol provided by the manufacturer (Pharmacia). HEK 293T cells were transfected with myc-tagged GTRAP4-41 or GTRAP4-48 and harvested in ice-cold immunoprecipitation (IP) buffer (phosphate buffered saline (pH 7.1), 5 mM EDTA, 1 mM sodium orthovanadate, 0.1 mM phenylmethylsulphonyl fluoride (PMSF), 0.3 µM aprotinin and 1% Triton X-100). The cellular lysate was incubated with GST or GST-EAAT4 immobilized on glutathione-Sepharose-4B, and washed to remove non-specifically bound proteins. Specifically bound proteins were eluted with 2×SDS loading buffer and analyzed by immunoblotting using an anti-c-myc antibody.

The Glutathione S-transferase (GST) Gene Fusion System (Pharmacia) was used to construct and generate GST-EAAC1 and GST-GTRAP3-18 fusion proteins using pGEX-6P-1 vector as described herein.

GTRAP4-41 and 4-48 Expression Constructs. For transient expression in HEK 293T cells full-length EAAT4 cDNA was subcloned into the EcoR I/BamH I site of the mammalian expression vector pRK5 (Genentech). For co-immunoprecipitation full-length GTRAP4-41 and GTRAP4-48 cDNAs were subcloned into the Not I site of a myc-tagged pRK5 vector.

Cell culture and cell transfection. HEK 293T cells were obtained from the American Type Culture Collection (Rockville, Md.) and maintained in MEM medium supplemented with 10% fetal bovine serum and L-glutamine. For transient transfections cells, were pre-washed with phosphate buffered saline (PBS) and incubated for 10 min at 4° C. with 40 mg of each plasmid DNA and 20 mg of salmon sperm DNA. Cells were transfected by electroporation at 300 V and 500 µF with a gene pulser (Bio-Rad) and grown for 48–72 h in either 10 cm culture dishes or plated onto poly-D-lysine coated coverslips in 6-well plates for co-localization studies.

Subcloning, stable transfection and maintenance of cell lines The EAAT4 cDNA was subcloned into pcDNA3.1/Hygro(+) (Invitrogen) using the EcoR I restriction site. The plasmid was linearized with Ssp I, ethanol precipitated and transfected into HEK 293T cells using the calcium phosphate-DNA precipitation method. 50 mg of DNA per 10 cm dish was used. Cells were incubated with the precipitate in 5% $CO_2$ at 37° C. for 6 hours, the medium containing the precipitate was removed and the cells were washed twice with PBS before adding fresh MEM medium. 48 h after transfection, the cells were split to 50% confluency and hygromycin (Invitrogen) was added at a concentration of 50 mg/ml. Cell culture medium containing hygromycin was changed every 3 to 4 days. After approximately 2- to 3-weeks of selection, a serial dilution was carried out and cells were plated out, without selection, in a 96-well plate to obtain one cell per well. Several colonies were picked, expanded in selective medium and checked for expression by western blotting. Similarly, the GTRAP4-41 cDNA was cloned into pcDNA3 using the Not I restriction site and linearized with Ssp I. Selection was with G418 (Mediatech) at a concentration of 5 mg/ml. The GTRAP4-48 cDNA was cloned into the inducible expression vector pIND (Invitrogen) using the EcoR I restriction site and linearized with Sca I. Selection was with G418 and expression of GTRAP4-48 was induced with 5 mM Ponasterone A (Ecdysone-Inducible Mammalian Expression System, Invitrogen).

Co-immunoprecipitation in heterologous cells. Full-length GTRAP4-41 and GTRAP4-48 cDNAs were subcloned into the Not I site of a myc-tagged pRK5 vector and used to transfect the HEK-rEAAT4 cell line by electroporation at 300 V and 500 µF with a gene-pulser (Bio-Rad). After transfection (48–72 h), cells were solubilized with 1 ml of ice-cold IP buffer for 2 h at 4° C. with rotation and centrifuged to remove cellular debris. 5 µg of rabbit anti-NEAAT4 antibody was added to 0.5 ml of supernatant and incubated overnight at 4° C. 150 µl protein A-Sepharose (Pharmacia) was then added for 2 h at 4° C., washed once with IP buffer and three times with IP minus Triton X-100. Bound protein was eluted by boiling in 3×SDS loading buffer, and analyzed by immunoblotting using the anti-c-myc antibody.

GTRAP3-18 Expression. For transient expression in HEK 293T cells, full-length EAAC1 cDNA was subcloned into the EcoR I/BamH I site of the mammalian expression vector pRK5 (Genentech). For co-immunoprecipitation full-length GTRAP3-18 cDNA were subcloned into the Not I site of a myc-tagged pRK5 vector.

Cell culture and cell transfection of GTRAP3-18 For transient transfections cells were pre-washed with PBS, incubated for with 40 mg of each plasmid DNA/20 mg of salmon sperm DNA and electroporated as described herein. In some cases, C6 glioma cells, known to naturally express high levels of EAAC1, were transfected with GTRAP3-18.

EXAMPLE 5

To determine the biochemical interaction between Glutamate Transporter Associated Proteins and glutamate transporter proteins, binding and immunoprecipitation assasys in vivo and in vitro were performed.

GTRAP4-41 and 4-48 Immunoprecipitation with Fusion Proteins. Full-length EAAT4 was subcloned into the EcoR I site of the GST-fusion vector pGEX-6P-1 (Pharmacia). Synthesis of recombinant proteins in BL21 cells (Novagen) was induced by 0.1 mM isopropyl b-D-thiogalactoside for 2 hrs at 30° C. and prepared as a crude bacterial lysate by mild sonication in ice-cold 1 C PBS and solubilization in 1% Triton X-100. Cell debris was removed by centrifugation at 7,000 g and the cleared bacterial lysate applied to glutathione-Sepharose-4B (Pharmacia). HEK 293T cells were transfected with myc-tagged GTRAP4-41 or GTRAP4-48 as described herein and harvested in ice-cold immunoprecipitation (IP) buffer (phosphate buffered saline (pH 7.1), 5 mM EDTA, 1 mM sodium orthovanadate, 0.1 mM phenylmethylsulphonyl fluoride (PMSF), 0.3 mM aprotinin and 1% Triton X-100) with 1% Triton X-100. The cellular lysate was incubated with GST or GST-EAAT4 immobilized on glutathione-Sepharose-4B, and washed to remove non-specifically bound proteins. Specifically bound proteins were eluted with 3×SDS loading buffer and analyzed by immunoblotting using an anti-c-myc antibody. Bands were visualized by HRP-conjugated secondary antibodies and ECL chemiluminescence (Amersham).

GTRAP4-41 and GTRAP4-48 bind to GST-EAAT4 fusion protein, but do not bind to GST.

Co-immunoprecipitation in heterologous cells Transiently transfected cells (as described herein) were solubilized with 1 ml of ice-cold IP buffer for 2 h at 4° C. with rotation and centrifuged to remove cellular debris. 1.2 mg of mouse anti-c-myc antibody was added to 0.5 ml of supernatant and incubated overnight at 4° C. 150 ml protein A-Sepharose (Pharmacia) was then added for 2 h at 4° C., washed once with IP buffer and three times with IP minus Triton X-100. Bound EAAT4 was eluted by boiling in 3×SDS loading buffer, and analyzed by immunoblotting using the anti-carboxy-terminal EAAT4 antibody.

GTRAP4-41, GTRAP4-48 and KIAA0380 (a close homolog of GTRAP4-48) are coimmunoprecipitated with EAAT4 protein using the amino-terminal anti-EAAT4 antibody.

Immunoprecipitation from cerebellum lysate. Sprague-Dawley (SD) rat cerebellum was dissected, washed with 50 mM Tris-HCl (pH 7.5), 2 mM EDTA and 0.5 mM DTT, and homogenized on ice in buffer containing 20 mM Tris-HCl (pH 7.5), 10% sucrose, 1 mM EDTA, 0.1 mM PMSF, 0.3 mM aprotinin, 1 mM benamidine, 10 mg/ml leupeptine and 10 mg/ml pepstatine. Protein concentration was measured and adjusted to 2–3 mg/ml, and the homogenate was mixed in a 1:1 ratio with the solubilization buffer (homogenization buffer plus 2% Triton X-100). After 2 h, the lysate was spun at 10,000 g for 10 min. For each immunoprecipitation, 500 mg of the Triton-lysate was incubated overnight at 4° C. with 5 μg of the anti-amino-terminal EAAT4 antibody. Immune complexes were precipitated with protein A Sepharose (Pharmacia), washed three times with 10 mM Tris-HCl (pH 7.5) and 5 mM EDTA, eluted with 3×SDS loading buffer, and processed for western blot analysis. The filters were probed with affinity purified rabbit antibodies against GTRAP4-41 and GTRAP4-48.

The biochemical interaction between GTRAP4-41 or GTRAP4-48 and EAAT4 was confirmed using an in vitro binding assay. Full-length myc-tagged GTRAP4-41 and GTRAP4-48 were expressed in HEK 293T cells. The solubilized cell extracts were then mixed with bead-linked GST-EAAT4 or GST alone and the bound proteins were eluted. GTRAP4-41 and GTRAP4-48 were specifically retained by the GST-EAAT4 fusion protein, but not by GST alone.

To further assess the interaction between GTRAP4-41 or GTRAP4-48 and EAAT4 in a cellular context, immunoprecipitation studies in transfected heterologous cells were performed. A stable rat EAAT4 expressing cell line was generated in HEK 293T cells (HEK-rEAT4) and transfected with cDNAs encoding myc-tagged GTRAP4-41 and GTRAP4-48. Antibodies directed to the amino-terminus of EAAT4 were used to immunoprecipitate the antigen and any associated protein.

Western blot analysis using an anti-c-myc antibody demonstrates that GTRAP4-41 and GTRAP4-48 coimmunoprecipitate with EAAT4. No coimmunoprecipitation is observed when the precipitating antibody is omitted. Similarly, when the anti-c-myc antibody is used, EAAT4 is co-immunoprecipitated with GTRAP4-41 and GTRAP4-48.

The GTRAP4-41 and GTRAP4-48 interaction with EAAT4 was then studied in vivo using solubilized brain preparations. GTRAP4-41 and GTRAP4-48 are co-immunoprecipitated with EAAT4 from brain by antibodies directed at the amino-terminus of EAAT4 but not by antibodies directed at the carboxy-terminus. However, since the site of interaction is within the carboxy-terminus of EAAT4, it is likely that the carboxy-terminal antibodies disrupt the protein-protein interaction. Furthermore, GTRAP4-41 and GTRAP4-48 appear to specifically interact with EAAT4, as GTRAP4-41 and GTRAP4-48 do not co-immunoprecipitate from brain with antibodies directed at the other glutamate transporters, e.g., GLT-1, GLAST and EAAC1. GTRAP4-48 is also not co-immunoprecipitated from brain with antibodies directed at GTRAP4-41. Similarly, GTRAP4-41 is not co-immunoprecipitated with antibodies directed at GTRAP4-48 from HEK 293T cells that were transfected with full-length myc-tagged GTRAP4-41 and GTRAP4-48, indicating that there is no direct interaction between GTRAP4-41 and GTRAP4-48.

GTRAP3-18 Immunoprecipitation. Coronal sections of rat brain were sliced at 1–2 mm intervals from the cerebellum to the olfactory bulbs. The cortex region was excised from the brain and placed in cold buffer A (50 mM Tris pH 7.5, 2 mM EDTA, 150 mM NaCl, 0.5 mM DTT). The tissue was washed three times in buffer A and the tissue was weighted. The tissue was then homogenized using a blender in 2.5 vol of buffer B (50 mM Tris pH 7.5, 10% glycerol, 5 mM Mg acetate, 0.2 mM EDTA, 0.5 mM DTT, 1 mM PMSF). The particulate material was removed by centrifugation at 15,000×g for 30 min at 4° C. The supernatant fraction was incubated with Protein A Sepharose beads and primary antibodies as described herein.

The interaction of GTRAP3-18 with EAAC1 was examined using in vitro and in vivo methods. For in vitro cell-free binding, EAAC1 was expressed as a fusion protein with glutathione S-transferase (GST), and GTRAP3-18 was produced and labeled with [$^{35}$S]-methionine by in vitro transcription and translation. Purified GST or GST-EAAC 1 fusion proteins immobilized on glutathione-Sepharose were incubated with [$^{35}$S]-labeled GTRAP3-18 protein. GTRAP3-18 specifically binds to immobilized GST-EAAC1 but not to GST alone, indicating an in vitro interaction.

Immunoprecipitation experiments were performed to test if EAAC1 and GTRAP3-18 interact in vivo. This was first examined in transfected HEK293 cells using amino-terminus c-myc tagged GTRAP3-18. EAAC1 is co-immunoprecipitated with c-myc-GTRAP3-18 in the cell extract prepared from co-expression cells but not from EAAC1 or c-myc-GTRAP3-18 single expression cells. Theses studies with single expression cells show that binding is specific since they rule out the possibility that the results are due to artifact from immunobead nonspecific binding or antibody cross-reaction, respectively. A truncated EAAC1 lacking the interacting carboxy-terminal domain (described herein) is not co-immunoprecipitated with c-myc-GTRAP3-18, further demonstrating the interaction of EAAC1 and GTRAP3-18. This interaction was specific, since EAAT4, another neuronal glutamate transporter subtype, is not immunoprecipitated with c-myc-GTRAP3-18. Identical results are obtained using COS-7 and C6 glioma cell lines.

To study the protein interaction in vivo, anti-EAAC1 or GTRAP3-18 polyclonal antibodies were used to immunoprecipitate EAAC1 or GTRAP3-18 from rat brain extract. Western blotting demonstrates that EAAC1 is specifically co-immunoprecipitated with GTRAP3-18, but not with GLAST, GLT-1 or EAAT4. Similarly, GTRAP3-18 was co-immunoprecipitated with EAAC1. These studies suggest that EAAC1 and GTRAP3-18 interact in vivo.

EXAMPLE 6

Identification of the EAAT4- GTRAP4-48 interaction site
To evaluate the general/region and or amino acid motif required for the association of GTRAP4-41 and GTRAP4-48 with EAAT4, a series of two-hybrid screen using different EAAT4, carboxy-terminal truncations and GTRAP proteins as bait was performed. A series of successively larger carboxy terminal deletions of the 77-amino acid carboxy-terminal EAAT4 bait was used to identify regions necessary for ginding of GTRAP4-41 and GTRAP4-48 to EAAT4. Residues 555–561 (QEAELTLP; SEQ ID NO:9) and 527–534 (GRGGNESVM; SEQ ID NO:10) are required for GTRAP4-41 and GTRAP4-48 binding, respectively (FIG. 2).

EXAMPLE 7

Expression and Localization of GTRAP

Expression of GTRAP4-41 and 4-48 protein in brain. GTRAP4-41 and GTRAP4-48 are expressed exclusively in the brain. The highest level of expression of both proteins is in the cerebellum, and somewhat lower levels of expression in the cortex. The apparent molecular weight for GTRAP4-41 is greater than 201 kD; the apparent molecular weight for GTRAP4-48 is less that 200 kD. The native proteins migrate in PAGE identical to proteins expressed in transfected HEK cells Expression of GTRAP3-18 mRNA in brain Northern analyses of GTRAP3-18 mRNA were performed in brain as well as various body organ tissues. Total RNA was isolated from various rat tissues using a Stratagene RNA isolation kit, separated on 1% agarose gel with 6.7% formaldehyde and blotted onto a nylon membrane (Gene-screen Plus; NEN) by capillary transfer. The blot was hybridized to the full length cDNA probe labeled with $^{32}$P by random priming, washed for 2×10 min in 2×SSC, 0.1% SDS at 42° C., 1×20 min in 0.1×SSC, 0.1% SDS at 65° C. and autoradiographed overnight.

GTRAP3-18 mRNA is widely distributed; GTRAP3-18 mRNA is found in the brain, kidney, heart, muscle, liver and cortex. This pattern is consistent with the distribution of EAAC1 in peripheral tissues (Furuta et al., J Neuroscience (1997) 17:8363–8375; Shayakul et al., Amer. J. Physiol. Renal Physiol. (1997) 42:F1023–F1029). Similarly, GTRAP3-18 protein is expressed in many neural and non-neural tissues, based on immunocytochemical studies using a polyclonal oligopeptide antibody to the amino-terminus of GTRAP3. GTRAP3-18 protein appears to aggregate as multimers. The dimeric form of GTRAP3-18 is the predominant species in tissue homogenates. The dimeric form is also observed when purified GTRAP3-18 protein is detected using the amino-terminal GTRAP3-18 antibody, and when c-myc-GTRAP3-18 protein is detected using anti-c-myc antibodies. Immunohistological analysis of rat brain reveals that GTRAP3-18 protein is expressed widely and is primarily localized to neurons such as cerebellar Purkinje cells which is identical to the distribution of EAAC1. In transfected HEK293 cells, EAAC1 protein appears to be aggregated at the cell membrane, while GTRAP3-18 protein is typically localized to the cell membrane and cytosol, and co-associated with EAAC1 protein at the cell membrane.

Co-localization of GTRAP4-48 or GTRAP4-41 with EATT4 HEK cells, transientlytransfected with EAAT4 (20 $\mu$g) and/or GTRAP4-41 (20 $\mu$g) and/or GTRAP4-48 (20 $\mu$g), were fixed with paraformaldehyde (4%) in phosphate buffer (0.1 M, pH7.4) for 20 min. The cells were then permeabilized with 0.1% Triton X-100, stained with the primary antibodies EAAT4 (1 mg/ml) and c-myc (5 mg/ml) for 1 h, rinsed and incubated with Texas-red and FITC-conjugated secondary antibodies at dilutions of 1:200. Immunofluorescence was viewed with a confocal microscope. Confocal microscopy of transfected cells and of brain sections was performed with a Zeiss LSM 510 laser scanning microscope using fluorescein (Vector, #FI1000) and Texas red (Vector, TI12000) flurochromes.

Both GTRAP4-41 and 4-48 co-localize to membranes domains with EAAT4. GTRAP4-48 expression is associated with a re-distribution of the protein on the membrane in a punctate-like organization.

Immunohistochemistry The cellular localization of GTRAP4-41 and 4-48 was studied in rat brain tissue. Rat brain sections were stained, as previously described Furuta, A. et al., *Neuroscience* 81, 1031–1042 (1997)) using the following antibodies: carboxy-terminal anti-EAAT4 (1.5 $\mu$g/ml), anti-GTRAP4-41 (127 ng/ml) or anti-GTRAP4-48 (132 ng/ml) antibodies. Texas-red and FITC-conjugated secondary antibodies were used at dilutions of 1:200.

Both GTRAP4-41 and GTRAP4-48 are highly localized to rat cerebellar cortex, with prominent immunolocalization to Purkinje cell somas and dendrites.

GTRAP4-41 and GTRAP4-48 are selectively localized to brain. In rat, GTRAP4-41 and GTRAP4-48 are predominately expressed in the cerebellum, especially the cerebellar cortex with prominent immunolocalization observed in Purkinje cell somas and dendrites, with low level immunoreactivity in striatum, hippocampus and thalamus. Previous studies have shown that EAAT4 is selectively localized to cerebellar Purkinje cells, although low level expression is observed in cerebral cortex, hippocampus and striatum (Furuta et al., *Neuroscience* 81, 1031–1042 (1997)) Thus, GTRAP4-41, GTRAP4-48 and EAAT4 are co-localized in brain tissue.

GTRAP3-18 mRNA is widely expressed in brain regions and body organs, consistent with the distribution of EAAC1 (Hediger et al., *Am. J Physiol* 277, F477–F480 (1999); Hediger *Am. J Physiol* 277, F487–F492 (1999)). Similarly, GTRAP3-18 protein is expressed in many neural and non-neural tissues when protein localization is examined using a polyclonal oligopeptide antibody to the amino-terminus of GTRAP3. GTRAP3-18 protein appears aggregated as multimers. The dimeric form of GTRAP3-18 is the predominant species in tissue homogenates and the dimeric form is also observed when purified GTRAP3-18 protein is detected using the amino-terminal GTRAP3-18 antibody, as well as when c-myc-GTRAP3-18 protein is detected using anti-c-myc antibodies. Immunohistological analysis of rat brain reveals that GTRAP3-18 protein is expressed widely and primarily localized to neurons such as cerebellar Purkinje cells, identical to the expression pattern observed for EAAC1 (He et al., *J Comp Neurol* 418, 255–269 (2000); Rothstein et al. *Neuron* 13, 713–725 (1994)).

Localization in heterologous cells In transfected HEK293 cells, EAAC1 protein appears aggregated at the cell membrane while GTRAP3-18 protein is typically localized to the cell membrane and cytosol, and co-associated with EAAC1 protein at the cell membrane.

EXAMPLE 8

GTRAPs Modulate Glutamate Transport

To determine function relationships between GTRAPs and glutamate transporter proteins, sodium-dependent, glutamate transport activity was measured in HEK-rEAAT4 cells transfected with one or more interacting proteins.

To determine the effects of GTRAPs on glutamate transport function, $Na^+$-dependent glutamate transport activity was measured in cells stably transfected with EAAT4, EAAC1, or another glutamate transporter protein and one or more interacter proteins. Stably transfected cells were grown in a monolayer on 6-well plates in MEM supplemented with 10% fetal bovine serum and L-glutamine. Assays were conducted when cells reached ~80% confluency. The wells were pre-rinsed twice with 2 ml of ice-cold tissue buffer (50 mM Tris, 320 mM sucrose, pH 7.4). The cells were then incubated for 4 min at 37° C. with 1 ml of either sodium- (120 mM NaCl, 25 mM $NaHCO_3$, 5 mM KCl, 2 mM $CaCl_2$, 1 mM $KH_2PO_4$, 1 mM $MgSO_4$, 10% glucose and 10 mM glutamate) or choline-(120 mM choline Cl, 25 mM Tris-HCl pH 7.4, 5 mM KCl, 2 mM $CaCl_2$, 1 mM $KH_2PO_4$, 1 mM $MgSO_4$, 10% glucose and 10 mM glutamate) containing buffer labeled with L-[$^3$H]Glu. Uptake was stopped by rinsing three times with 2 ml of ice-cold wash buffer (50 mM Tris pH 7.5 and 160 mM NaCl). Cells were solubilized in 1 ml of 0.1 N NaOH, and 500 ml of lysate was analyzed for radioactivity in a scintillation counter. $Na^+$-dependent uptake was defined as the difference in radioactivity accumulated in $Na^+$-containing buffer and in choline-containing buffer. Protein content was measured and glutamate uptake calculated as nmole glutamate per mg of protein. In some cases, homogenates were examined for EAAT4, GTRAP4-41 and GTRAP4-48 protein.

In an alternative protocol, HEK-rEAAT4 cells transfected with GTRAP4-41 and GTRAP4-48 were grown in a monolayer on 6-well plates in MEM supplemented with 10% fetal bovine serum and L-glutamine. Assays were conducted about 72 h after transfection using the method of Davis (Davis et al., *J. Neurosci.* 18, 2475–2485 (1999)). GTRAP4-41 and GTRAP4-48 were subcloned into the Eco RI site of HSV PrPUC amplicon parent vector (pHSVPrPUC) (Geller, A. I., et al., *Proc Natl Acad Sci U.S.A* 87, 8950–8954 (1990)). 3.6 μg of amplicon vector DNA and 25 μg pBAC-V2 DNA were used to transfect $2–10^7$ baby hamster kidney cells according to previously published methods (Stavropoulos and Strathdee, *J. Virol.* 72, 7137–7143 (1998)). Virus was harvested about 72 hrs after transfection and titered as previously described (Bowers et al. *Mol. Ther.* 1, 294–299 (2000)). $2 \times 10^5$ expression particles were injected intra-cisternally into male Sprague-Dawley rats (250 g) obtained from Zivic Miller. About 48 h after injection, the rats were sacrificed and synaptosomal preparations of the cerebelli were prepared using a polytron. Glutamate transport was measured by methods described herein.

Figure 3A:
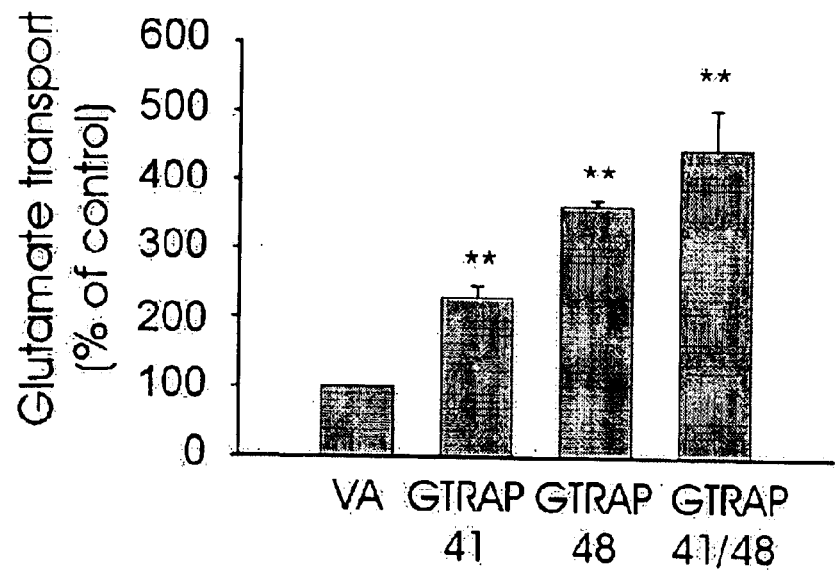
FIG. 3A shows the effect of GTRAP4-41 and GTRAP4-48 on sodium-dependent glutamate uptake in transfected HEK-rEAAT4 cells.
Figure 3B:
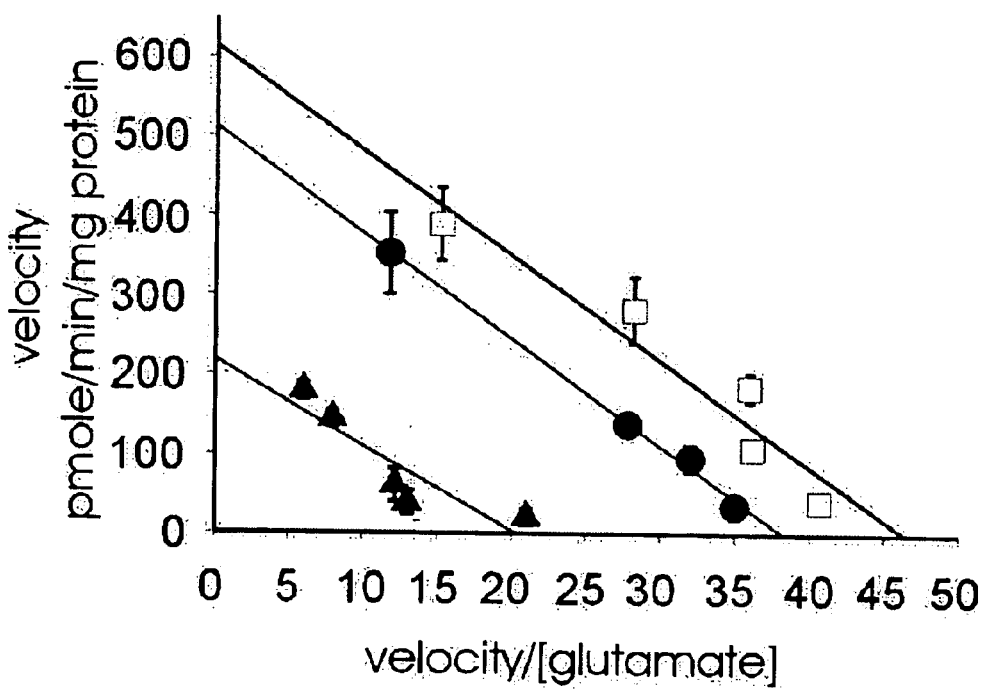
FIG. 3B shows kinetic data which demonstrates that GTRAP4-41, in the presence of EAAT4, increases the $V_{max}$ of glutamate uptake.

GTRAP4-41 and GTRAP4-48 produce a two- to four-fold increase in glutamate transport, respectively. The co-expression of GTRAP4-41 and GTRAP4-48 results in a further increase in glutamate uptake. Kinetic analysis indicates that GTRAP4-41 and GTRAP4-48 produced an increase in the $V_{max}$ of glutamate transport activity (FIG. 3). There is also a small increase in the $K_m$ values when GTRAP4-41 and GTRAP4-48 are co-expressed, but these are not statistically significant, suggesting that the interacting proteins do not alter the affinity of the transporter for glutamate. GTRAP4-41 and GTRAP4-48 may therefore enhance glutamate transport either via an increase in the catalytic rate of the transporter or via an increase in cell surface availability. Results are presented in FIG. 3. GTRAP41 and GTRAP48 expression in HEK-rEAAT4 cells increase glutamate uptake significantly over vector alone (VA) transfected cells. Data in FIG. 3A are the mean±SEM of at least four independent observations and were compared by students t test, (**$p<0.005$). Concentration dependence of $Na^+$-dependent L-[$^3$H]-glutamate uptake was assayed in the presence of increasing concentrations of glutamate. In FIG. 3B, the values are expressed as the mean±SEM of a representative experiment carried out in triplicate. Kinetic data shows that GTRAP41 (□) increases the $V_{max}$ from 222 to 605 pmol/mg/min and increases the $K_m$ slightly from 7 to 11 μM, compared to EAAT4 alone (▲). GTRAP48 increases the $V_{max}$ from 208 to 512 pmol/mg/min (•) and increased the $K_m$ from 10 to 13 μM.

Figure 4A:
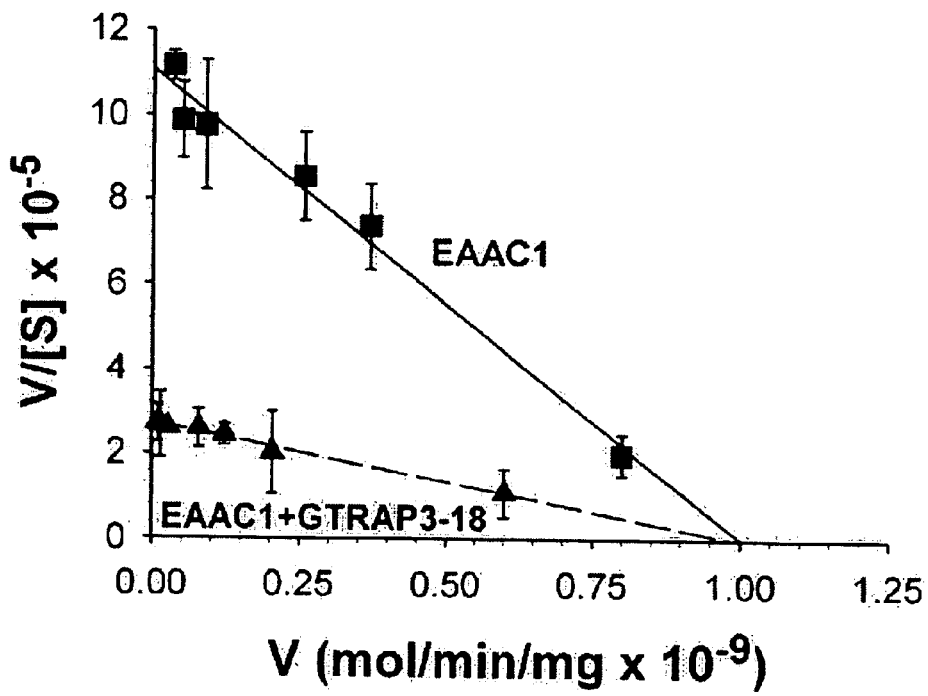
FIG. 4A shows the effect of GTRAP3-18 on sodium-dependent glutamate transport in transfected HEK-293 cells.
Figure 4B:
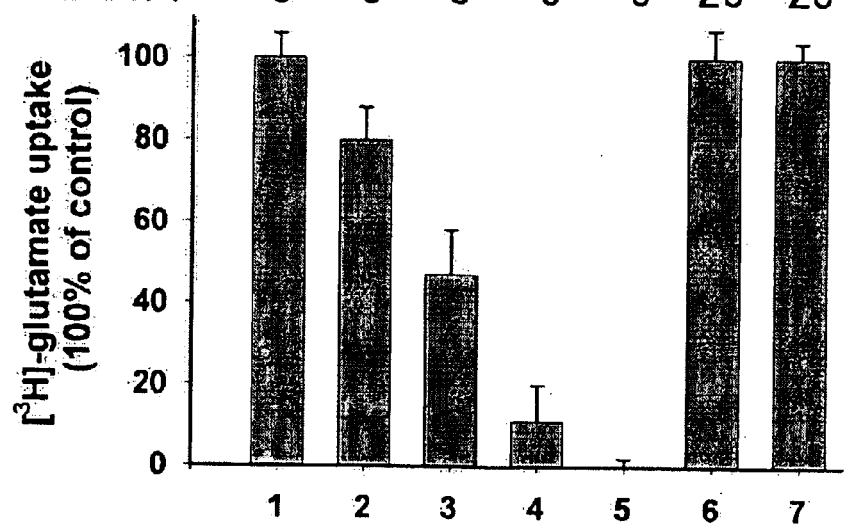
FIG. 4B shows that the effect of GTRAP3-18 on EAAC1-mediated glutamate transport is specific.

To test if GTRAP3-18 modulates EAAC1 function, sodium-dependent [$^3$H]-glutamate transport was studied in HEK293 cells co-expressing both proteins, 72 hrs after transfection (Rothstein et al. *Neuron* 16, 675–686 (1996); Lin et al., *Neuron* 20, 589–602 (1998)). Total glutamate transport progressively decreases with increasing GTRAP3-18 protein expression (FIG. 4). GTRAP3-18 negatively modulates EAAC1-mediated glutamate transport. Glutamate transport was studied in HEK293 cells transfected with plasmids indicated in FIG. 4. GTRAP3-18 inhibited EAAC1-mediated transport, but had no effect on EAAT4 (n=6). The co-expression of GTRAP-3-18 has no effect on total EAAC1 protein expression. Analysis of HEK293 cells by confocal microscopy and surface biotinylation reveal no alteration in the membranous localization of EAAC1. Superoxide dismutase (SOD1) was used as a control. Eadie-Scatchard plot of glutamate transport in transfected HEK293 cells reveals a 4–10 fold decrease in affinity (n=4). This effect is specific for EAAC1; co-expression of GTRAP3-18 with EAAT4 has no effect on transport activity.

The inhibition of transport is not due to a decrease of EAAC1 protein level by the co-expression of GTRAP3-18, as quantitated by Western blotting. Similarly, the loss of EAAC1 activity is not due to altered protein trafficking; even at high levels of GTRAP3-18 expression, when little EAAC1-mediated transport is observed, EAAC1 surface expression is unaltered as determined by surface biotinylation and confocal microscopy.

To evaluate the biochemical nature of altered transport, kinetic analyses were performed with HEK293 cells co-expressing EAAC1 and GTRAP3-18. EAAC1 and GTRAP3-18 co-expressing cells show a decrease in affinity ($K_m$=40 μM, Vmax=0.99 nmol/min/mg protein; n=4, P<0.01) without a shift in the $V_{max}$ when compared to cells only expressing EAAC1 ($K_m$=9 μM; $V_{max}$=1.02 nmol/min/mg protein; FIG. 4A). Similar results are observed with other cell lines (COS7 and C6 glioma).

EXAMPLE 9

Cell Surface Levels of GTRAPs and Cytoskeletal Stability

To examine changes in the cell surface levels of EAAT4, a cell membrane-impermeant biotinylation reagent to label cell surface proteins selectively. Biotinylation of cell surface proteins was performed as described in Duan et al. (Duan, et al., *J. Neurosci.* 19, 10193–10200 (1999)). SOD1 was used to control for total protein and to determine whether the biotinylation reagent labels proteins in the intracellular compartment. Densitometry was performed using the NIH Image program.

Figure 5A:
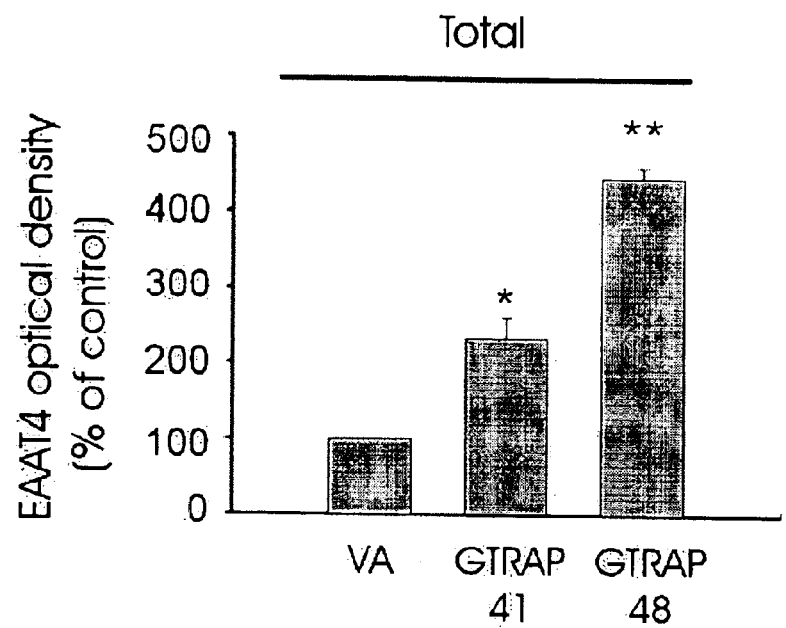
FIGS. 5A and 5B show the effect of Glutamate Transporter Associated Proteins (GTRAPs) on glutamate transporter protein expression.
Figure 5B:
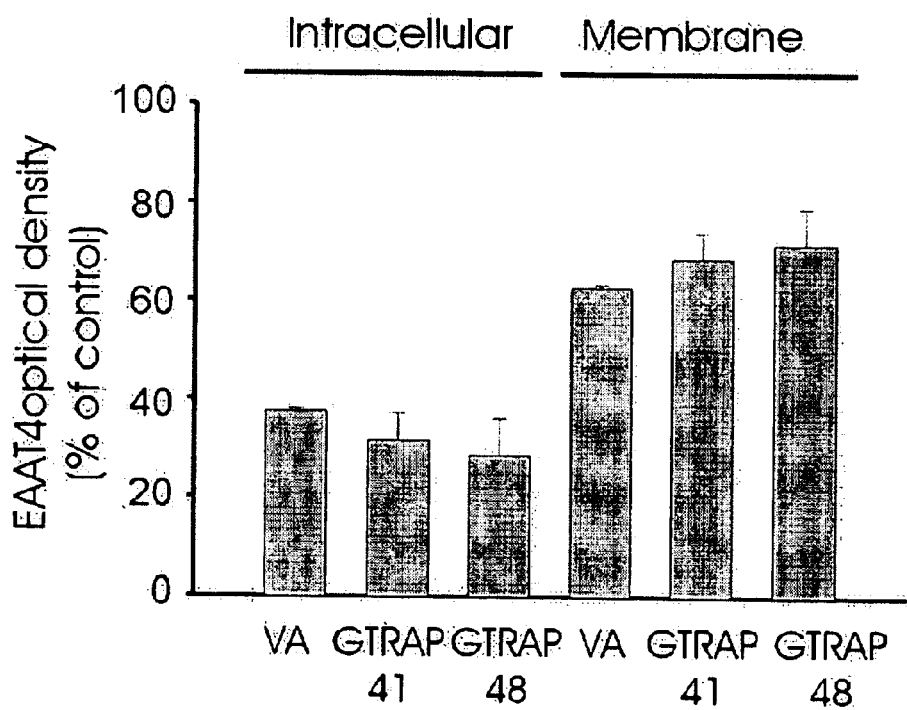

The total amount of EAAT4 is increased when GTRAP4-41 and GTRAP4-48 are coexpressed (FIG. 5). In contrast the total amount of SOD1, a control for total amount of protein loaded, is unaltered or decreased in the GTRAP4-41 and GTRAP4-48 samples, respectively. The majority of the EAAT4 is biotinylated, indicating that it is at the cell surface. However the percentage of total EAAT4 that is at the cell surface remains the same when GTRAP4-41 and GTRAP4-48 are co-expressed. Taken together, these results indicate that GTRAP4-41 and GTRAP4-48 stabilize/anchor EAAT4 at the cell membrane, making it less likely to be internalized and subsequently degraded, rather than causing an increased trafficking of EAAT4 to the cell surface.

However it is also possible that there is increased expression of the cell's native gene. To address this question cells were treated 48 hrs after transfection with cycloheximide, an inhibitor of protein synthesis. Quantification by densitometry shows that 12 hrs after treatment, the EAAT4 protein in HEK-rEAAT4 cells is reduced to 54±0.6% of the level prior to cycloheximide treatment. In contrast, 81±2% and 74±1.7% of the EAAT4 protein remains after 12 hrs when GTRAP4-41 and GTRAP4-48 are coexpressed, respectively. These results provide evidence that GTRAP4-41 and GTRAP4-48 do stabilize EAAT4 at the membrane.

EXAMPLE 10

GTRAP-Glutamate Transport Protein Interactions

To determine whether the EAAT4/GTRAP4-48 interaction is required to mediate the increase in EAAT4 activity, HEK-rEAAT4 cells were transfected with GTRAP4-48 constructs lacking the last 155 amino acids which were pulled out by EAAT4 in the yeast two-hybrid screen. The carboxy-terminally truncated GTRAP4-48 had only a modest effect on stimulating EAAT4 activity, indicating that the protein-protein interaction is responsible for the majority of the increase in uptake activity. HEK-rEAAT4 cells were co-transfected with GTRAP4-48 and a myc-tagged cDNA construct encoding the last 77 amino acids of EAAT4 to disrupt the interaction of GTRAP4-48 with full-length EAAT4. Co-expression of this construct inhibits the GTRAP4-48 mediated effect by approximately 25%, but co-expression of a smaller construct (residues 1452 to 1578), which lacked the GTRAP4-48 binding domain, has no effect. Taken together these results indicate that the EAAT4/GTRAP4-48 interaction plays an important role in the modulation of EAAT4 uptake activity.

Figure 6A:
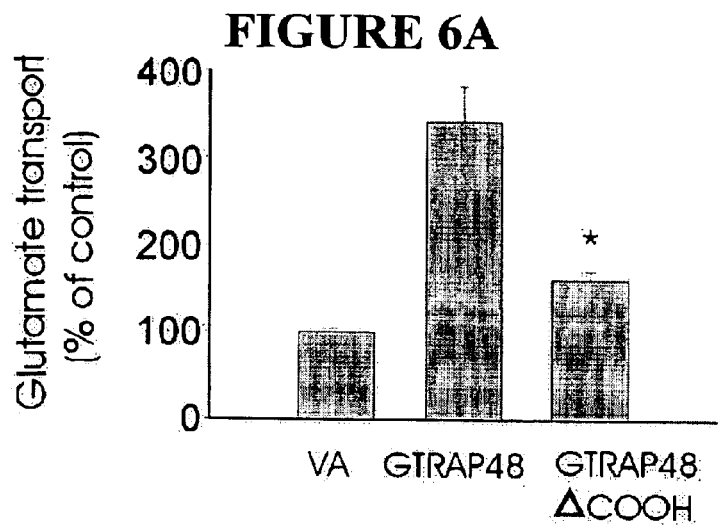
FIGS. 6A–C show the effect of GTRAPs on glutamate transporter protein activity.
Figure 6B:
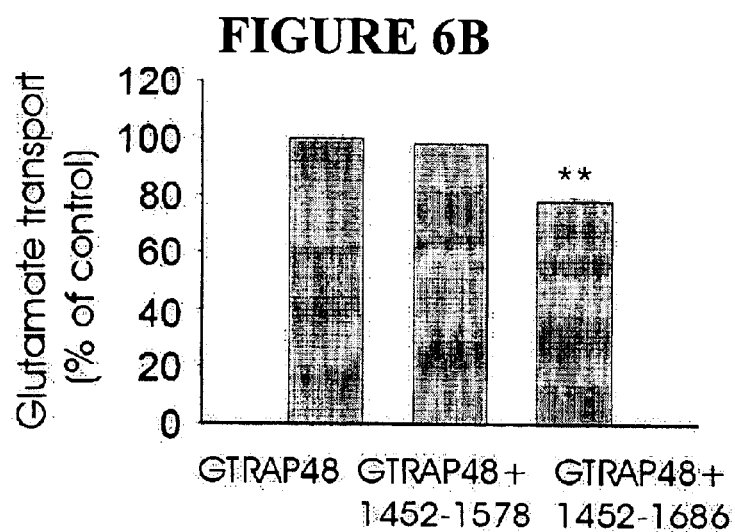
Figure 6C:
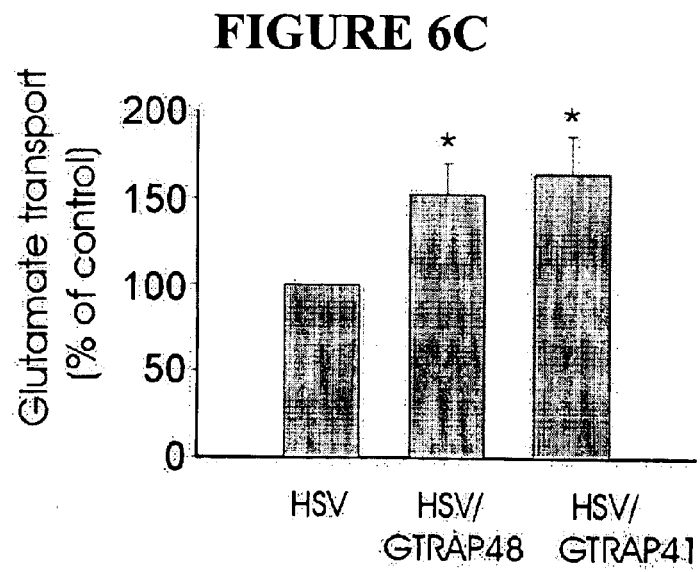

These results are summarized in FIG. 6. FIG. 6A shows results of experiments in which HEK-rEAAT4 cells were transfected with a GTRAP48 construct that lacked the C-terminus (domain that interacts with EAAT4). Disruption of the EAAT4/GTRAP48 interaction significantly reduces the GTRAP48-mediated increase in EAAT4 uptake activity (*p<0.05). Disruption of the protein-protein interaction by overexpression of the EAAT4 C-terminus in HEK-rEAAT4 cells transfected with GTRAP48. The GTRAP48-mediated effect on EAAT4 activity was reduced by ~25% (**p<0.005; FIG. 6B). $Na^+$-dependent L-[$^3$H]-glutamate was assayed in triplicate and values are expressed as the mean±SEM of six independent experiments. GTRAP41 and GTRAP48 significantly increased glutamate uptake in vivo (*p<0.05; FIG. 6C).

The physiological relevance of GTRAP4-41 and GTRAP4-48 on EAAT4 uptake activity in vivo was subsequently examined by the intra-cisternal injection of HSV amplicon vectors expressing GTRAP4-41 and GTRAP4-48. Cerebellar glutamate uptake was measured 48 hrs after injection and found to be elevated when GTRAP4-41 and GTRAP4-48 are expressed but not when the control HSVlac amplicon vector was injected (FIG. 6C). Dihydrokainic acid (DHK), an inhibitor of GLT-1 mediated glutamate transport, has no effect on cerebellar glutamate uptake, ruling out any involvement of GLT-1. Unfortunately there is no method to distinguish functionally between GLAST, EAAC1 and EAAT4. However it has been have shown that GTRAP4-41 and GTRAP4-48 do not interact directly with any other transporter, it is likely that the observed increase in uptake is attributed to an increase in EAAT4 activity. Western blot analysis confirms increased expression of GTRAP4-41 and GTRAP4-48 in the cerebellum following the injections.

EXAMPLE 11

Clustering of Glutamate Transporter Proteins at Synapses

To examine whether GTRAPs are involved in, or associated with, the clustering of EAAT4 at synapses primary cultures of rat Purkinje cell neurons were examined immunocytochemically. Rat brain sections were stained, as previously described (Furuta et al., Neurosciences 81:1031–1042 (1997)) using the following antibodies: carboxy-terminal anti-EAAT4 (1.5 μg/ml), anti-GTRAP4-41 (127 ng/ml) or anti-GTRAP4-48 (132 ng/ml) antibodies. Texas-red and FITC-conjugated secondary antibodies were used at dilutions of 1:200.

EAAT4 and GTRAP4-41 immunoreactivity is observed throughout the soma and dendrites but is also found to colocalize in distinct clusters. Labeling with synaptophysin, a presynaptic protein, reveals that 71% of synapses possessed clusters of EAAT4 and GTRAP4-41 [n=12]. This perisynaptic distribution of GTRAP4-41 correlates with earlier EM studies that showed that EAAT4 is a perisynaptic protein. Similar studies could not be carried out for GTRAP4-48 due to low level of expression at this early developmental stage.

EXAMPLE 12

Interaction with Rho: Since GTRAP4-48 possesses areas of homology to p115 and PDZRhoGEF, two novel RhoGEFs that selectively activate Rho (Hart et al., *J. Biol. Chem.* 271, 25452–25458 (1996), Fukuhara et al., *J. Biol. Chem.* 274, 5868–5879 (1999)), interaction of GTRAP4-48 with the Rho family of GTPases was investigated.

Guanine nucleotide exchange assay. Small G proteins GST-RhoA, GST-CDC42 and GST-Rac were expressed in bacterial cells and affinity purified to ~80% purity using a glutathione column. Twenty pmoles of each protein were incubated with 100 pmoles GTPγS for 10 min at 30° C. with varying concentrations of full-length GTRAP4-48 or p115. The binding reactions were filtered through BA-85 nitrocellulose and the amount of GTPγS bound to small G protein was quantitated by scintillation counting of the dried filters. The amount of GTPγS that bound to GST-RhoA, GST-Cdc42 and GST-Rac in the presence of full-length GTRAP4-48 or p115 was measured.

Figure 7A:
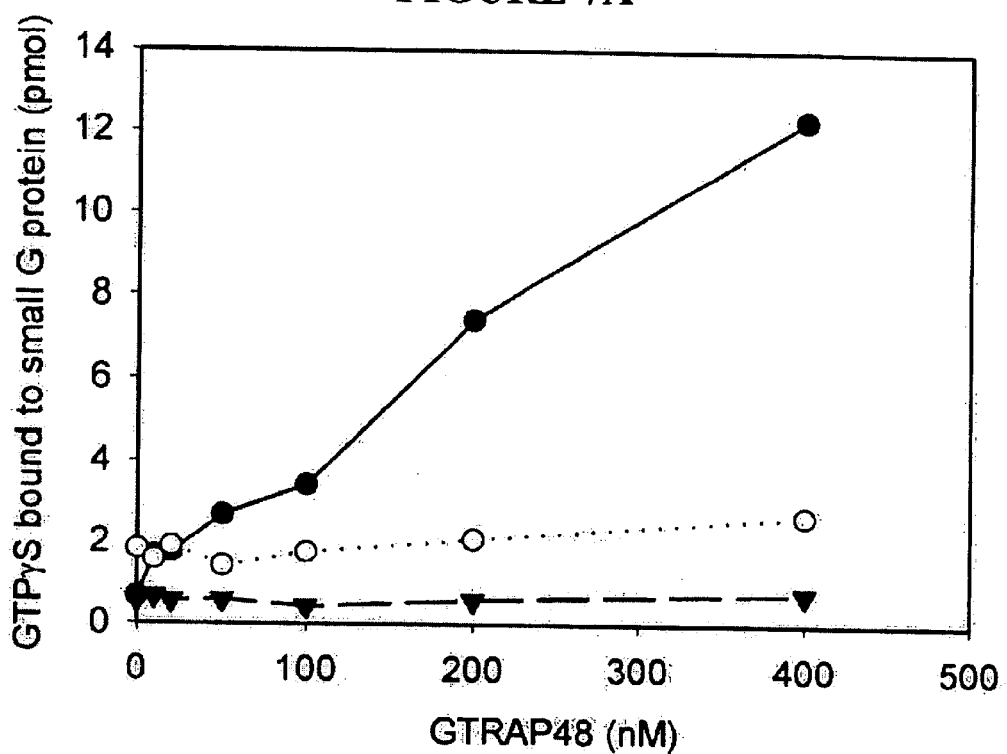
FIGS. 7A and 7B show the interaction between GTRAP4-48 and RhoGEF.
Figure 7B:
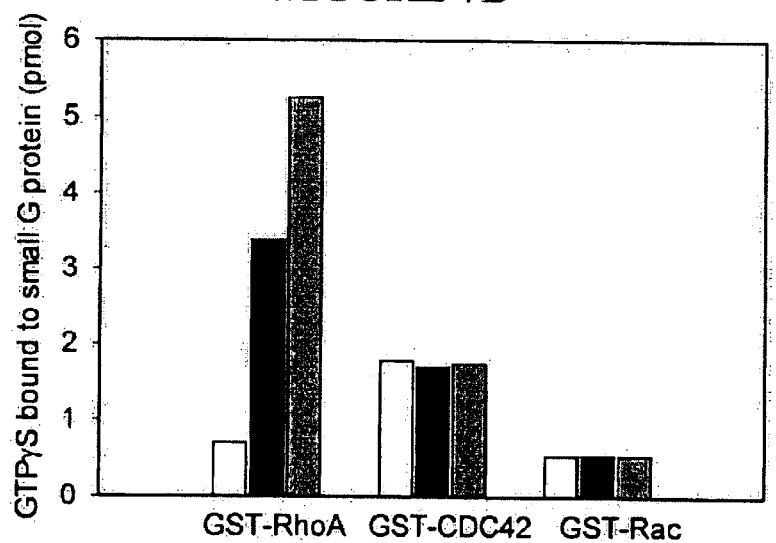

GTRAP4-48, like p115, demonstrates a specific guanine nucleotide exchange activity for Rho (FIG. 7). Co-immunoprecipitation assays also show that GTRAP4-48 interacts with the active form (in the presence of aluminium fluoride) of the $G\alpha_{13}$ subunit and therefore, may act as a link between G-protein coupled receptors and their downstream targets. However, unlike p115, regulation of the GTRAP4-48 RhoGEF activity by $G\alpha_{13}$ nor the stimulation of the GTPase activity of $G\alpha_{13}$ by GTRAP4-48 could be demonstrated. Rho is known to regulate the remodeling of the actin cytoskeleton through various actin-binding proteins, although the mechanism is not yet well characterized (Hall, *Science* 279, 509–514 (1998)).

Since GTRAP4-48 can activate Rho, expression of GTRAP4-48 was studied to determine if it could induce the reorganization of the actin cytoskeleton and whether it alters the distribution of GTRAP4-41, a possible actin binding protein. When GTRAP4-41 is expressed alone there is a close relationship between actin and GTRAP4-41 at the cell membrane but there are very few organized actin filaments. Conversely, when GTRAP4-41 and GTRAP4-48 are co-expressed, GTRAP4-41 is found to co-localize with actin in structures that resembled actin-stress fibers, a typical Rho-dependent effect. Overexpression of GTRAP4-48 also induces the formation of membrane ruffling and filopodia, suggesting some degree of cross-talk between the small GTPases, as these are typical Rac and Cdc42 dependent effects. These results indicate that there is a close relationship between GTRAP4-48 and the reorganization of GTRAP4-41 and the actin cytoskeleton.

EXAMPLE 13

Antisense Treatment with GTRAP3-18

To demonstrate tonic modulation of EAAC1 activity by GTRAP3-18, antisense oligomers were used to lower GTRAP3-18 expression in HEK293 cells. Western blot analyses and glutamate uptake assays reveal endogenous expression of EAAC1 and GTRAP3-18 protein in HEK cells, but no expression of other transporter subtypes, e.g., GLAST, GLT-1, or EAAT4. Antisense oligomers, targeted to the 5'-GTRAP3-18 transcript, were transfected into HEK293 cells.

Figure 8A:
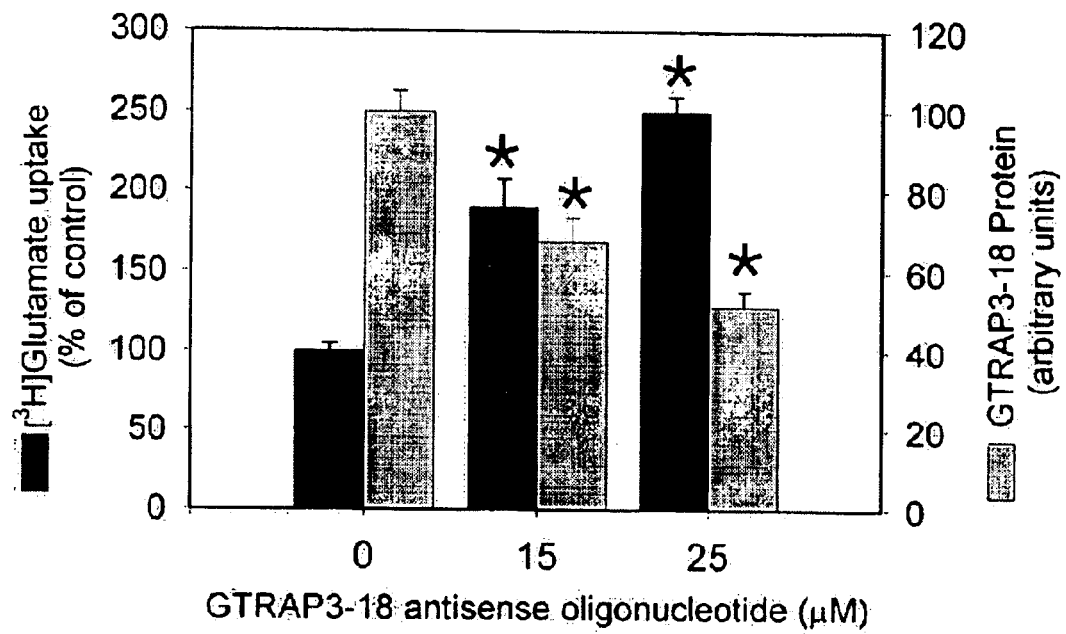
FIGS. 8A–C show the effects of GTRAP3-18 antisense oligonucleotide on glutamate transport.

Antisense oligomers specifically reduced endogenous GTRAP3-18 protein level (FIG. 8A, gray bars); EAAC1 protein level was not affected. Significantly, glutamate transport activity was concomitantly elevated with the reduction of GTRAP3-18 protein level (black bars).

To examine modulation of EAAC1 by GTRAP3-18 in vivo, GTRAP3-18 antisense oligomers were administered intraventricularly. Sequences for the novel phosphodiester oligonucleotides used were: sense GTRAP3-18: 5'-GTGAACCTTGCCCGCTC-3', antisense GTRAP3-18: 5'-GAGCGGGGCAAGGTTCAC-3' Oligonucleotides (5 µg/µL), separately or in combination were administered intraventricularly over 3–11 days, by mini-osmotic pumps (Alza Corp., Palo Alto, Calif.) as described previously (Rothstein et al., (1994)).

Figure 8B:
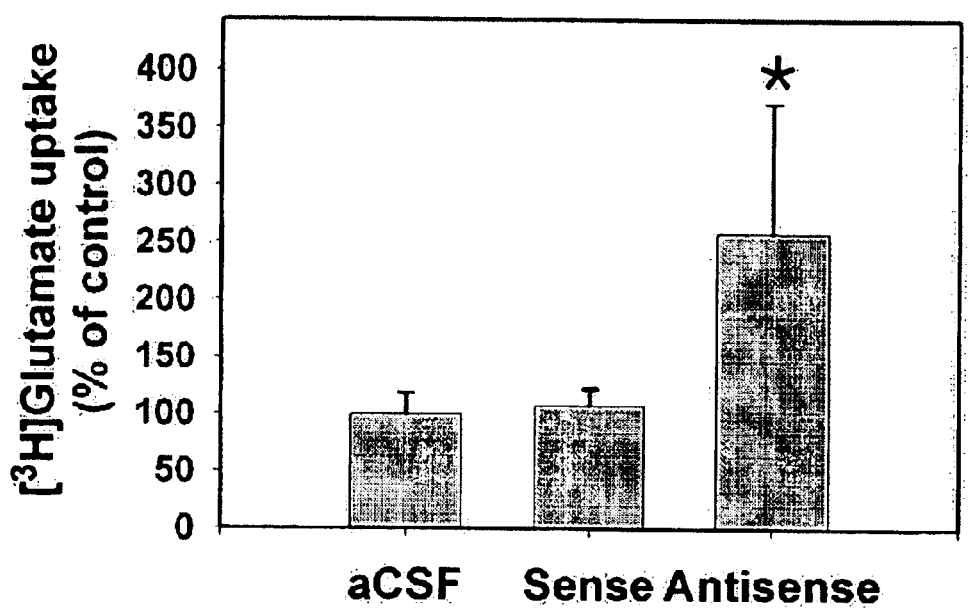
Figure 8C:
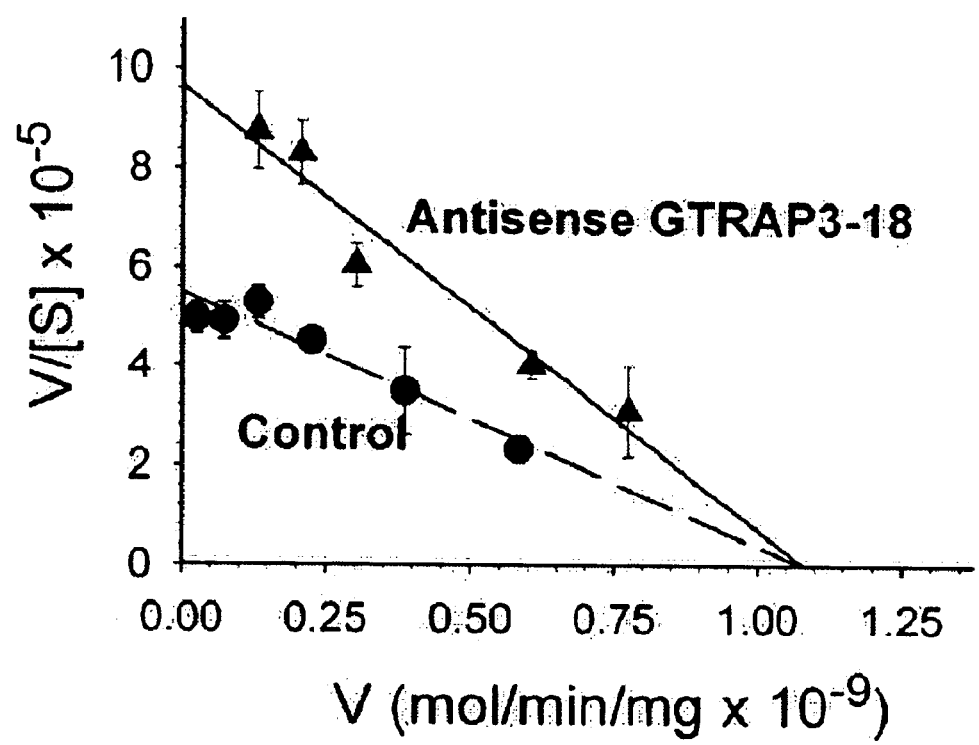

Eleven days of antisense treatment resulted in a reduction of GTRAP3-18 protein level and a significant increase in cortical glutamate uptake, whereas glutamate uptake was not altered in sense oligomer-treated animals (FIG. 8B). The effect was due to increased EAAC1-mediated transport because it was not altered by dihydrokainic acid (DHK), an inhibitor of GLT-1-mediated glutamate transport (Robinson et al. (1998) Neurochem. Int. 33:479–491). In kinetic studies of DHK-insensitive, cortical glutamate uptake from antisense-treated animals, the apparent affinity for glutamate was increased (antisense $K_m$=10 µM, $V_{max}$=1.08 nmol/min/mg protein) compared to artifical CSF or sense treated control animals (control $K_m$=19.7 µM; $V_{max}$=1.08 nmol/min/mg protein; FIG. 8C). These results suggest that GTRAP3-18 negatively modulates EAAC1 glutamate transport activity in vivo.

EXAMPLE 14

Regulation of GTRAP3-18 by Retinoic Acid

Figure 9A:
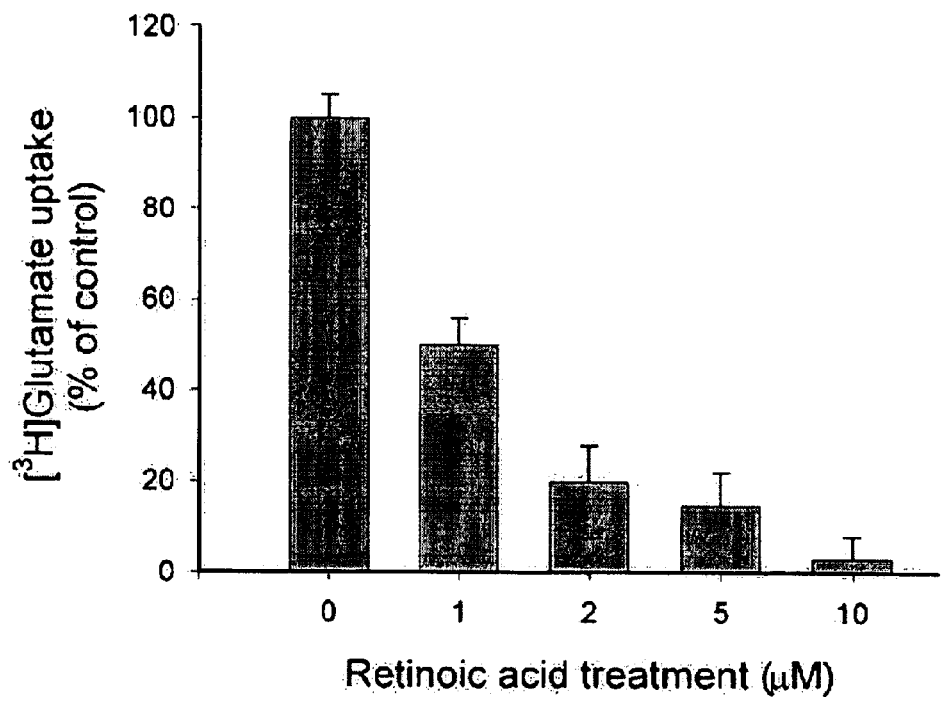
FIGS. 9A–E show the effect of retinoic acid on GTRAP3-18-mediated glutamate transport.
Figure 9B:
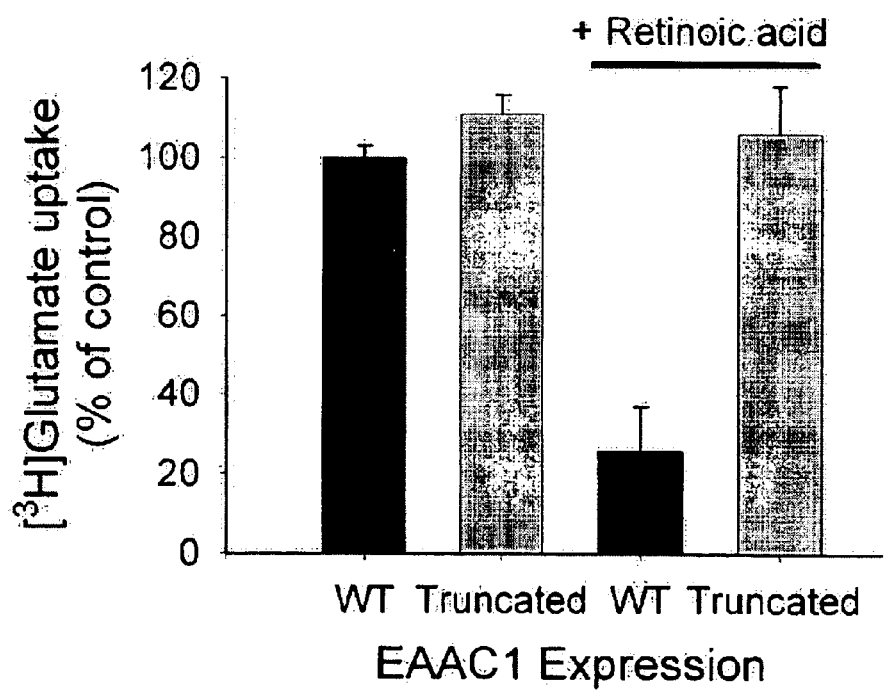
Figure 9C:
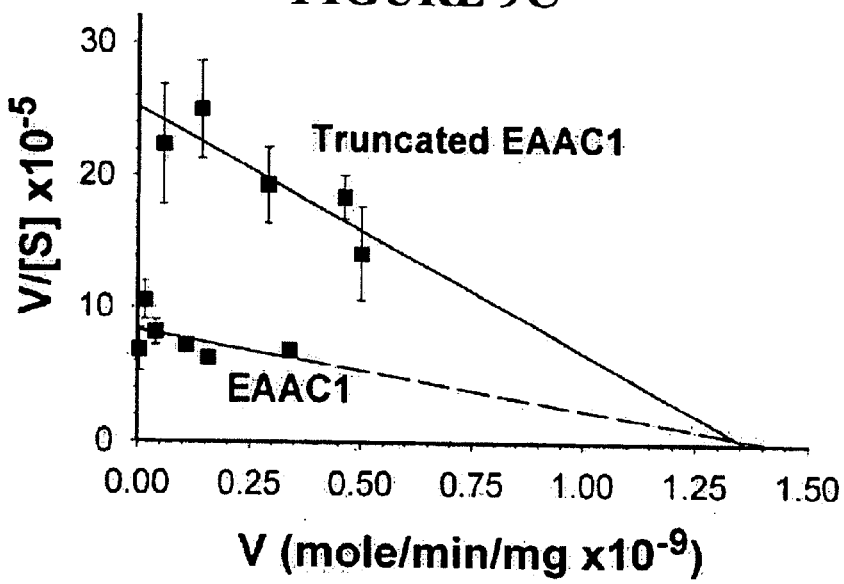
Figure 9D:
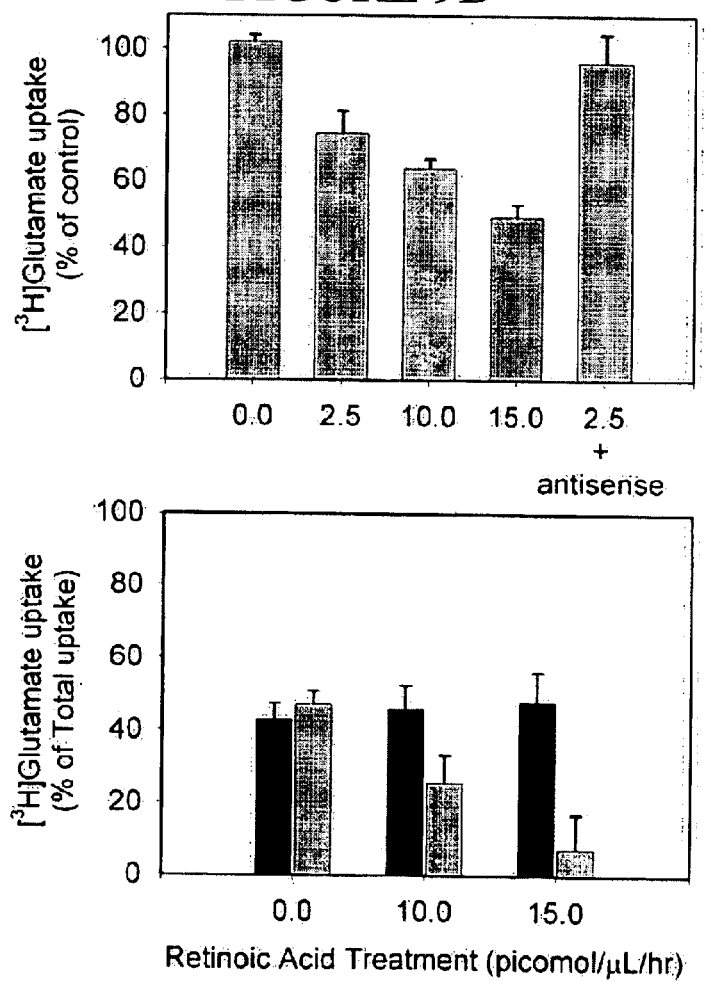
Figure 9E:
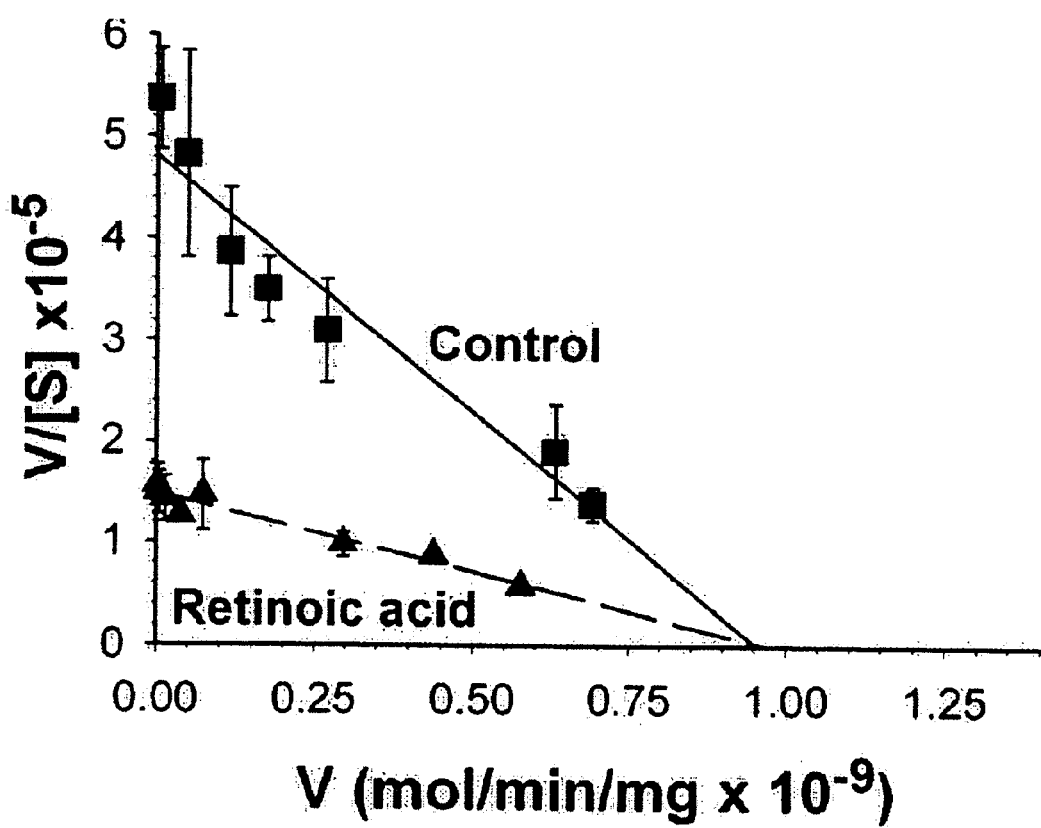

Human GTRAP3-18 (JWA protein) was originally identified as a retinoic acid responsive gene. Therefore, retinoic acid was tested for its ability to up-regulate GTRAP3-18 expression and consequently inhibit EAAC1-mediated glutamate transport in HEK293 cells. Retinoic acid induces a large increase in GTRAP3-18 expression, over a non-toxic dose range from 1–10 µM. A significant decrease in glutamate transport activity paralleled the increase of GTRAP3-18 protein level (FIG. 9). The loss of transport activity is not due to changes in EAAC1 protein level (FIG. 9A) or the cellular membrane localization of EAAC1 protein by retinoic acid as examined by fluorescent microscopy. To confirm that loss of transport activity was specifically due to GTRAP3-18 and not by other factors induced by retinoic acid or direct effects on EAAC1, a truncated EAAC1 cDNA, lacking the last 93 amino acids, was constructed. The truncation corresponded to the region used as bait in yeast two-hybrid screening, and was not able to interact with GTRAP3-18. Nevertheless, after transient expression in HEK293 cells, the truncated EAAC1 transported glutamate. Importantly, retinoic acid treatment does not alter activity of the truncated EAAC1 protein; even though GTRAP3-18 protein expression was markedly elevated (FIG. 10B). Thus, the loss of transport activity by retinoic acid was the result of GTRAP3-18 induction. Interestingly, truncated EAAC1 has increased glutamate transport activity compared to wild-type. Truncated EAAC1 had a $K_m$ of 5.4 µM, which was greater than a three-fold increase in affinity compared to wild-type EAAC1 (Km=17 µM; FIG. 9C). This could reflect lack of natural inhibition of the truncated protein EAAC1 by endogenous GTRAP3-18-results similar to the effects of GTRAP3-18 antisense treatment (FIG. 9E).

To test this hypothesis in vivo, retinoic acid was infused intraventricularly (1–20 μM; 0–20 pmol/μL). After 4 days of treatment, cortical GTRAP3-18 protein expression was increased in a dose dependent manner, and this was associated with a significant decrease of total glutamate uptake (FIG. 9D, top panel). This effect is specifically due to decreased EAAC1-mediated transport because it was not altered by the glutamate transport inhibitor dihydrokainic acid, at a concentration that predominantly effects GLT-1 (Robinson et al. (1998)). Kinetic analysis of DHK-insensitive, cortical glutamate transport from animals treated four days with intraventricular retinoic acid reveals a 4-fold decrease in affinity compared to control transport (FIG. 9E) which is very similar to that seen in vitro (FIG. 9B). In addition, retinoic acid inhibition of glutamate transport could be reversed in vivo; chronic intraventricular treatment with antisense GTRAP3-18 oligomer (50–100 ng/day, for 7–10 days) blocks the retinoic acid (2.5 μM) induction of GTRAP3-18, and also blocks the inhibition of glutamate transport seen with retinoic acid treatment (FIG. 9D, top panel). Retinoic acid had no effect on glutamate transport by cells expressing GLT-1 or EAAT4.

EXAMPLE 15

Glutamate Transporter Associated Protein PCTAIRE-1

The glutamate transporter EAAT4 possesses high affinity $Na^+$-dependent transport activity, as well as a unique ligand-gated $C^-$ conductance. Largely located in the somatodendritic compartment of the cerebellar Purkinje cell, altered function of EAAT4 may contribute to the pathogenesis of spinocerebellar ataxia and alcoholic cerebellar degeneration. In an effort to delineate possible regulatory mechanisms of EAAT4, we have identified glutamate transporter associated proteins (GTRAPs). Using the amino terminus of rat EAAT4 as bait in a yeast two-hybrid screen, an interacting protein was isolated. Subsequent sequence analysis identified the GTRAP as PCTAIRE-1, a serine/threonine kinase related to the cyclin-dependent kinase 2 (cdk2) family. In vitro and in vivo co-immunoprecipitations from rat cerebelli were performed, confirming specificity of interaction; co-localization of EAAT4 and PCTAIRE-1 within the cerebellum was determined using immunofluorescence. In order to investigate regulatory physiology of the PCTAIRE-1/EAAT4 interaction, co-transfection experiments and pharmacologic manipulation were carried out. PCTAIRE-1, although a member of the cdk2 family, is present mainly in terminally differentiated tissues such as brain. It has been shown to interact with members of signal transduction cascades (14-3-3 proteins) and components of cellular protein networks such as p11, a target for annexin II. These data suggest a mechanism by which EAAT4 may be linked to cellular regulatory machinery via the GTRAP PCTAIRE-1.

Methods. Yeast Two-Hybrid Screening: Screening was performed using the AH109 yeast strain harboring the reporter genes ADE/HIS, as well α- and β-galactosidase. The initial 60 amino acids of EAAT4 were subcloned in-frame into pGBKT7 (GAL4 binding domain, CLONTECH), and used to screen a rat brain cDNA library constructed in pACT2 (GAL4 activation domain, CLONTECH). Following cotransformation and verification of true positive colonies, DNA sequence analysis was performed. Obtained sequences were compared to known GENBANK submissions, resulting in identification of a true postive with with >95% homology to the final 201 amino acids of rat PCTAIRE-1.

Creation of expression constructs: Full length rat PCTAIRE-1 was isolated from a rat brain cDNA library via PCR amplification using upstream and downstream primers based on the known PCTAIRE sequence. Products were cloned into pCMVmyc tagged eukaryotic expression vector (CLONTECH), and expression verified by western blotting.

Two PCTAIRE-1 proteins are identified. PCTAIRE-1a is encoded by PCTAIRE-1 nucleic acid sequence, nucleotides 251–451 and 583–1872 (SEQ ID NO:8) and PCTAIRE-1b is encoded by PCTAIRE-1 nucleic acid sequence, nucleotides 487–1872 (SEQ ID NO:22).

Immunoprecipitations. In-vitro coimmunoprecipitations were performed on stably transfected HEK cells expressing EAAT4. Vector DNA or myc-tagged PCTAIRE vector was then introduced. Following expression, cells were solubilized with ice-cold IP buffer and centrifuged to remove cellular debris. 0.5 ml of supernatant was then incubated with or without 1.5 μg anti-c-myc antibody (Boehringer-Mannheim). Complexes were then isolated using protein-A Sepharose, washed four times with IP buffer with and without Triton X-100, and visualized using SDS-PAGE. EAAT4 western blotting was performed using affinity purified rabbit polyclonal Ab at 1:200 dilution.

In-vitro coimmunoprecipitation of EAAT4 with myc tagged antibody in EAAT4 expressing HEK cells transfected with myc-labeled PCTAIREs is demonstrated.

In-vivo coimmunoprecipitation was performed using the cerebellum of a 5 day-old Sprague-Dawley rat. Homogenization was performed on ice using a buffer containing 20 MM Tris-HCl (pH 7.5), 10% sucrose, 1 mM EDTA, and protease inhibitors. The homogenate was mixed 1:1 with buffer containing 2% Triton X-100, and solubilized for 2 h at 4° C. 0.5 mg of protein was used for each immunoprecipitation. Antibodies to the carboxy terminal EAAT4 (2.0 μg), as well as antibody to the transporter GLT (2.0 μg) were used. In addition, blocking peptide was presorbed to EAAT4 Ab to further demonstrate specificity. Western blotting was performed using PCTAIRE-1 antibody at 1:200 dilution (Santa Cruz).

In-vivo coimmunoprecipitation of PCTAIRE by EAAT4 is found in neonatal rat cerebellum. A PCTAIRE doublet (62 and 68 kDa) is recovered by immunoprecipitation with c-terminal EAAT4 Ab, and inhibited by preabsorption of EAAT4 Ab with blocking peptide.

Transfection of EAAT4 expressing HEK cells with PCTAIRE results in diminished $Na^+$-dependent glutamate uptake. HEK cells and EAAT4 expressing HEK cells were transfected with 1.0 μg of pCMV PCTAIRE plasmid, and allowed to express for 48 hours. Cell monolayers were then washed with tissue buffer (50 mM Tris, 320 mM sucrose, pH 7.4). The cells were then incubated for 4 min at 37° C. with 1 mL of either sodium-(120 mM NaCl, 25 mM NaHCO₃, 5 mM KCl, 2 mM CaCl₂, 1 mM KH₂PO₄, 1 mM MgSO₄, 10% glucose and 10 μM glutamate or choline-(120 mM choline-Cl, 25 mM Tris-HCl, 5 mM KCl, 2 mM CaCl₂, 1 mM KH₂PO₄, 1 mM MgSO₄, 10% glucose and 10 μM glutamate) containing buffer. Glutamate uptake assays were then performed using L-[³H]-Glutamate in the presence and absence of $Na^+$. After rinsing, cells were lysed in 0.1 N NaOH and lysate radioactivity measured using a scintillation counter. Protein content was measured and glutamate uptake calculated as the difference between $Na^+$ containing and sodium free values per mg of protein.

Inhibition of $Na^+$-dependent glutamate uptake by PCTAIRE is reversible using the cdk2 inhibitor olomucine. HEK cells expressing EAAT4 were transfected with 1.0 μg of pCMV PCTAIRE plasmid as described above, and allowed to express for 48 hours. Prior to glutamate uptake assay, cells were treated with 100 μM olomucine for 30 minutes at 37° C. as indicated. Olomocine belongs to a class of cyclin dependent kinase inhibitors which inhibit activity via competition at the ATP binding site.

Immunofluorescence microscopy displays colocalization of EAAT4 and PCTAIRE in the Purkinje cell layer of the rat cerebellum. A five day-old rat pup was perfusion fixed, the brain extracted, and 25 μm sections stained with antibodies to c-terminal EAAT4 (1.5 μg/mL) and PCTAIRE-1 (1.5 μg/mL). Prominent double-labeling is evident in the Purkinje cell layer, especially the cell soma, where EAAT4 is known to be present during the early postnatal period.

These results indicate that the serine/threonine kinase PCTAIRE interacts with the amino-terminus of the glutamate transporter EAAT4. This interaction results in downregulation of $Na^+$-dependent glutamate uptake, and this process is reversible using an inhibitor of cyclin dependent kinases. In addition, immunofluorescence reveals that both EAAT4 and PCTAIRE localize to the cerebellum, particularly the purkinje cell layer. Although PCTAIRE bears homology to the family of cyclin dependent kinases involved in proliferation, it is found mainly in terminally differentiated tissues such as brain. Other EAAT4 interacting proteins have recently been identified, both of which interact at the carboxy-terminus, and upregulate glutamate uptake. GTRAP41 is a new member of the β-III spectrin family, and is likely an actin-binding protein. GTRAP4-48 is a novel RhoGEF that may provide a link between the heterotrimeric G-proteins and small GTP-binding proteins of the Rho family. Together with PCTAIRE, these interactors may regulate glutamate uptake through EAAT4.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An isolated polynucleotide selected from the group consisting of:
   (a) a polynucleotide encoding a polypeptide having an amino acid sequence as set forth in SEQ ID NO:4;
   (b) a polynucleotide of (a), wherein all T's are replaced by U's;
   (c) a polynucleotide complementary to the full length polynucleotide of (a); and
   (d) a polynucleotide having a nucleotide sequence as set forth in SEQ ID NO:3.

2. An expression vector comprising a polynucleotide of claim 1.

3. The expression vector of claim 2, wherein the vector is virus-derived.

4. The expression vector of claim 2, wherein the vector is plasmid-derived.

5. An isolated host cell comprising a vector of claim 2.

6. A method for producing a polypeptide comprising the steps of:
   (a) culturing a host cell of claim 5 under conditions suitable for the expression of the polypeptide; and
   (b) recovering the polypeptide from the host cell culture.

7. The isolated polynucleotide of claim 1, wherein the polynucleotide encodes a peptide having an amino acid sequence as set forth in SEQ ID NO:4.

8. The isolated polynucleotide of claim 1, wherein the polynucleotide has a nucleotide sequence as set forth in SEQ ID NO:3.

* * * * *

SEQUENCE LISTING

<160> NUMBER OF SEQ ID NOS: 22

<210> SEQ ID NO 1
<211> LENGTH: 7240
<212> TYPE: DNA
<213> ORGANISM: Rattus
<220> FEATURE:
<221> NAME/KEY: CDS
<222> LOCATION: (1)..(7164)

<400> SEQUENCE: 1

```
atg agc agc acc ctg tca ccc act gac ttc gac agc ttg gag atc cag      48
Met Ser Ser Thr Leu Ser Pro Thr Asp Phe Asp Ser Leu Glu Ile Gln
1               5                   10                  15 ggc cag tac agt gac atc aac aac cgc tgg gac ctg ccc gac tca gat      96
Gly Gln Tyr Ser Asp Ile Asn Asn Arg Trp Asp Leu Pro Asp Ser Asp
            20                  25                  30 tgg gac aat gac agc agt tca gcc cgc ctc ttt gag agg tcc aga att     144
Trp Asp Asn Asp Ser Ser Ser Ala Arg Leu Phe Glu Arg Ser Arg Ile
        35                  40                  45 aag gcc ctg gca gat gag cga gaa gcc gtg cag aag aaa acc ttc acc     192
Lys Ala Leu Ala Asp Glu Arg Glu Ala Val Gln Lys Lys Thr Phe Thr
    50                  55                  60 aag tgg gtg aac tcc cac ctg gcc cgg gtg aca tgc cgg gtg gga gac     240
Lys Trp Val Asn Ser His Leu Ala Arg Val Thr Cys Arg Val Gly Asp
65                  70                  75                  80 ctg tac agc gac ctg cgg gac ggg cgc aac ctc ctg agg ctc ctg gag     288
Leu Tyr Ser Asp Leu Arg Asp Gly Arg Asn Leu Leu Arg Leu Leu Glu
                85                  90                  95 gtg ctc tcg gga gag acc ctg cca aaa ccc acc aag ggc cgg atg cgg     336
Val Leu Ser Gly Glu Thr Leu Pro Lys Pro Thr Lys Gly Arg Met Arg
            100                 105                 110 att cac tgc ctg gag aat gtc gac aaa gca ctg cag ttc ctg aag gag     384
Ile His Cys Leu Glu Asn Val Asp Lys Ala Leu Gln Phe Leu Lys Glu
        115                 120                 125 cag aag gtg cac ctg gaa aac atg ggc tcc cac gac att gtg gat ggg     432
Gln Lys Val His Leu Glu Asn Met Gly Ser His Asp Ile Val Asp Gly
    130                 135                 140 aac cac cgt ctg acc ctt ggg cta gtg tgg acc atc atc ctc cga ttt     480
Asn His Arg Leu Thr Leu Gly Leu Val Trp Thr Ile Ile Leu Arg Phe
145                 150                 155                 160 cag atc caa gac atc agt gtg gag aca gaa gac aac aag gag aag aag     528
Gln Ile Gln Asp Ile Ser Val Glu Thr Glu Asp Asn Lys Glu Lys Lys
```

```
                    165                 170                 175
tca gcc aag gat gcc ctg ctg ctg tgg tgc cag atg aag act gca ggg      576
Ser Ala Lys Asp Ala Leu Leu Leu Trp Cys Gln Met Lys Thr Ala Gly
            180                 185                 190 tat ccc aat gtc aat gtg cac aac ttt acc acc agt tgg aga gat ggg      624
Tyr Pro Asn Val Asn Val His Asn Phe Thr Thr Ser Trp Arg Asp Gly
        195                 200                 205 ctg gcc ttt aat gcc att gtg cac aaa cac cgg cca gac ctg ttg gat      672
Leu Ala Phe Asn Ala Ile Val His Lys His Arg Pro Asp Leu Leu Asp
    210                 215                 220 ttt gag tcc ctg aag aag tgt aac gca cac tac aat ctg cag aat gct      720
Phe Glu Ser Leu Lys Lys Cys Asn Ala His Tyr Asn Leu Gln Asn Ala
225                 230                 235                 240 ttc aat ctg gct gaa aag gaa ctt ggc ctg acg aag ctc ctg gat cct      768
Phe Asn Leu Ala Glu Lys Glu Leu Gly Leu Thr Lys Leu Leu Asp Pro
                245                 250                 255 gaa gat gtg aac gta gac caa ccc gat gag aag tcc atc atc acc tac      816
Glu Asp Val Asn Val Asp Gln Pro Asp Glu Lys Ser Ile Ile Thr Tyr
            260                 265                 270 gtg gcc act tac tac cac tac ttc tcg aag atg aag gcc ctg gct gtg      864
Val Ala Thr Tyr Tyr His Tyr Phe Ser Lys Met Lys Ala Leu Ala Val
        275                 280                 285 gaa ggc aaa agg att ggc aag gtc ctg gac cat gcc atg gag gca gaa      912
Glu Gly Lys Arg Ile Gly Lys Val Leu Asp His Ala Met Glu Ala Glu
    290                 295                 300 cac ctg gta gag aaa tat gag tcc ctg gcc tct gaa ctg ctg cag tgg      960
His Leu Val Glu Lys Tyr Glu Ser Leu Ala Ser Glu Leu Leu Gln Trp
305                 310                 315                 320 atc gag caa acg att ggg acc ttc aat gac cga cag ctg gcc aac tcc     1008
Ile Glu Gln Thr Ile Gly Thr Phe Asn Asp Arg Gln Leu Ala Asn Ser
                325                 330                 335 ctg agt ggc gtc cag aac cag ctg cag tct ttc aat tcc tac cgc acg     1056
Leu Ser Gly Val Gln Asn Gln Leu Gln Ser Phe Asn Ser Tyr Arg Thr
            340                 345                 350 gtg gag aag cca ccc aag ttc aca gag aaa ggg aac ttg gag gtg ttg     1104
Val Glu Lys Pro Pro Lys Phe Thr Glu Lys Gly Asn Leu Glu Val Leu
        355                 360                 365 ctc ttc acc atc cag agt aag ctg cgg gcc aac aac cag aaa gtc tac     1152
Leu Phe Thr Ile Gln Ser Lys Leu Arg Ala Asn Asn Gln Lys Val Tyr
    370                 375                 380 aca cca cgc gaa ggc cgg ctc atc tcg gac atc aac aag gcc tgg gag     1200
Thr Pro Arg Glu Gly Arg Leu Ile Ser Asp Ile Asn Lys Ala Trp Glu
385                 390                 395                 400 cgg cta gag aaa gcc gaa cat gag cga gag ctg gcc ctg cgc acg gag     1248
Arg Leu Glu Lys Ala Glu His Glu Arg Glu Leu Ala Leu Arg Thr Glu
                405                 410                 415 ctg atc cgc cag gag aag ctg gag caa ctg gct gct cgc ttc gac cgc     1296
Leu Ile Arg Gln Glu Lys Leu Glu Gln Leu Ala Ala Arg Phe Asp Arg
            420                 425                 430 aag gct gcc atg cgg gag acc tgg ctc agt gag aac cag cgc ctc gtc     1344
Lys Ala Ala Met Arg Glu Thr Trp Leu Ser Glu Asn Gln Arg Leu Val
        435                 440                 445 tcc cag gac aac ttt ggc ctg gag ctg gca gca gtg gag gca gca gtg     1392
Ser Gln Asp Asn Phe Gly Leu Glu Leu Ala Ala Val Glu Ala Ala Val
    450                 455                 460 cgg aag cat gaa gcc att gag aca gac att gtg gcc tac agc ggc cgg     1440
Arg Lys His Glu Ala Ile Glu Thr Asp Ile Val Ala Tyr Ser Gly Arg
465                 470                 475                 480 gtg caa gcg gtg gac gcc gta gcc gca gaa ctg gcc gct gag cat tac     1488
```

```
                 Val Gln Ala Val Asp Ala Val Ala Ala Glu Leu Ala Ala Glu His Tyr
                                 485                 490                 495 cat gac att aag cgc att gcg gcg cgg cag aac aac gtg gcc cgg ctc           1536
His Asp Ile Lys Arg Ile Ala Ala Arg Gln Asn Asn Val Ala Arg Leu
                500                 505                 510 tgg gac ttc tta cga gag atg gtg gcc gcc cgc cgt gag cgg ctc ctt           1584
Trp Asp Phe Leu Arg Glu Met Val Ala Ala Arg Arg Glu Arg Leu Leu
                515                 520                 525 ctc aac ctg gag ctg cag aag gtg ttt cag gac ctg ctc tac ctc atg           1632
Leu Asn Leu Glu Leu Gln Lys Val Phe Gln Asp Leu Leu Tyr Leu Met
                530                 535                 540 gac tgg atg gca gag atg aag ggc cgg ctg cag tct cag gac cta ggc           1680
Asp Trp Met Ala Glu Met Lys Gly Arg Leu Gln Ser Gln Asp Leu Gly
545                 550                 555                 560 aag cat ctg gct gga gtg gaa gat cta ctg caa cta cac gaa ctg gtg           1728
Lys His Leu Ala Gly Val Glu Asp Leu Leu Gln Leu His Glu Leu Val
                565                 570                 575 gag gcg gac att gca gtt cag gct gag agg gtg cga gcg gtc agc gcc           1776
Glu Ala Asp Ile Ala Val Gln Ala Glu Arg Val Arg Ala Val Ser Ala
                580                 585                 590 tct gcc ctg cgc ttc tgc gac cca ggg aaa gag tat aga cct tgc ggc           1824
Ser Ala Leu Arg Phe Cys Asp Pro Gly Lys Glu Tyr Arg Pro Cys Gly
                595                 600                 605 ccg cag cta gtg tca gag agg gta gcc act ctg gag cag agc tat gag           1872
Pro Gln Leu Val Ser Glu Arg Val Ala Thr Leu Glu Gln Ser Tyr Glu
                610                 615                 620 gcc ctg tgc gaa ttg gca gca act cga agg gcc cga ctg gaa gag tcc           1920
Ala Leu Cys Glu Leu Ala Ala Thr Arg Arg Ala Arg Leu Glu Glu Ser
625                 630                 635                 640 cgt cgt ctc tgg agg ttc ctc tgg gaa gtg ggt gag gcc gag gcc tgg           1968
Arg Arg Leu Trp Arg Phe Leu Trp Glu Val Gly Glu Ala Glu Ala Trp
                645                 650                 655 gtt cgg gag cag cag cac ctc ctg gcc tca gct gag aca ggc cgg gac           2016
Val Arg Glu Gln Gln His Leu Leu Ala Ser Ala Glu Thr Gly Arg Asp
                660                 665                 670 ctg act ggt gtc ctc cgc ctg ctc aat aag cac aca gcc cta cgg ggt           2064
Leu Thr Gly Val Leu Arg Leu Leu Asn Lys His Thr Ala Leu Arg Gly
                675                 680                 685 gag atg agt ggc cgc ctg ggg ccc ctg aag ctc acc ctg gaa caa ggt           2112
Glu Met Ser Gly Arg Leu Gly Pro Leu Lys Leu Thr Leu Glu Gln Gly
                690                 695                 700 cag cag tta gtt gcc gag ggc cac cct gga gct aac caa gcc tca acc           2160
Gln Gln Leu Val Ala Glu Gly His Pro Gly Ala Asn Gln Ala Ser Thr
705                 710                 715                 720 cgt gca gca gag ctc cag gcc cag tgg gag cga cta gaa gcc ctg gcc           2208
Arg Ala Ala Glu Leu Gln Ala Gln Trp Glu Arg Leu Glu Ala Leu Ala
                725                 730                 735 gag gag cga gcc cag cgg cta gca cag gct gcc agc ctc tac cag ttc           2256
Glu Glu Arg Ala Gln Arg Leu Ala Gln Ala Ala Ser Leu Tyr Gln Phe
                740                 745                 750 cag gca gat gcc aat gac atg gag gct tgg ttg gtg gac gca cta cgc           2304
Gln Ala Asp Ala Asn Asp Met Glu Ala Trp Leu Val Asp Ala Leu Arg
                755                 760                 765 ctg gta tct agc cct gag gta ggg cac gat gag ttc tcc acg cag gcc           2352
Leu Val Ser Ser Pro Glu Val Gly His Asp Glu Phe Ser Thr Gln Ala
                770                 775                 780 ctg gcc agg cag cac agg gcc ctt gag gag gag atc gag gcc cac cgg           2400
Leu Ala Arg Gln His Arg Ala Leu Glu Glu Glu Ile Arg Ala His Arg
785                 790                 795                 800
```

```
cct aca ctg gat gcc ttg agg gag cag gct gca gcc ctg cca cct gca        2448
Pro Thr Leu Asp Ala Leu Arg Glu Gln Ala Ala Ala Leu Pro Pro Ala
            805                 810                 815 ctg agc cac aca cct gag gta cag ggc agg gtg ccc act ctg gag cag        2496
Leu Ser His Thr Pro Glu Val Gln Gly Arg Val Pro Thr Leu Glu Gln
            820                 825                 830 cac tat gag gag ctg cag gcc cgg gca ggt gag cgt gca cga gcc ctg        2544
His Tyr Glu Glu Leu Gln Ala Arg Ala Gly Glu Arg Ala Arg Ala Leu
            835                 840                 845 gaa gca gcc ctg gcg ttc tat acc atg ctc agc gag gcc ggg gct tgt        2592
Glu Ala Ala Leu Ala Phe Tyr Thr Met Leu Ser Glu Ala Gly Ala Cys
        850                 855                 860 ggg ctc tgg gta gag gag aag gag cag tgg ctc aac ggg ctg gcc cta        2640
Gly Leu Trp Val Glu Glu Lys Glu Gln Trp Leu Asn Gly Leu Ala Leu
865                 870                 875                 880 cct gag cgc ctg gag gac ccg gag gtg gtc caa cag agg ttt gag acc        2688
Pro Glu Arg Leu Glu Asp Pro Glu Val Val Gln Gln Arg Phe Glu Thr
                    885                 890                 895 tta gag ccc gaa atg aac gcc ctg gct gca cgg att act gct gtc agt        2736
Leu Glu Pro Glu Met Asn Ala Leu Ala Ala Arg Ile Thr Ala Val Ser
                900                 905                 910 gac ata gct gag cag ttg ctg aag gcc agt cca cca ggc aag gac cgc        2784
Asp Ile Ala Glu Gln Leu Leu Lys Ala Ser Pro Pro Gly Lys Asp Arg
            915                 920                 925 atc att ggc acc cag gag cag ctc aac caa agg tgg cag cag ttc agg        2832
Ile Ile Gly Thr Gln Glu Gln Leu Asn Gln Arg Trp Gln Gln Phe Arg
        930                 935                 940 tcc ctg gca ggt ggc aaa aag gca gct ctg aca tca gcc ctg agc atc        2880
Ser Leu Ala Gly Gly Lys Lys Ala Ala Leu Thr Ser Ala Leu Ser Ile
945                 950                 955                 960 cag aat tac cac cta gag tgc aca gag acc cag gcc tgg atg aga gaa        2928
Gln Asn Tyr His Leu Glu Cys Thr Glu Thr Gln Ala Trp Met Arg Glu
                    965                 970                 975 aag acc aag gtc att gag tct acc cag gac cta ggc aat gat cta gct        2976
Lys Thr Lys Val Ile Glu Ser Thr Gln Asp Leu Gly Asn Asp Leu Ala
                980                 985                 990 ggt gtg ctg gcc ctg cag cgg aag  ctg gca ggc act gag  aga gat ctg      3024
Gly Val Leu Ala Leu Gln Arg Lys  Leu Ala Gly Thr Glu  Arg Asp Leu
            995                 1000                1005 gaa gcc  atc tct gcc cgg gtg  ggt gag ctg acc caa  gag gca aat         3069
Glu Ala  Ile Ser Ala Arg Val  Gly Glu Leu Thr Gln  Glu Ala Asn
    1010                1015                1020 gct ttg  gct gct ggg cac cca  gcc caa gcc cct gcc  atc aac aca         3114
Ala Leu  Ala Ala Gly His Pro  Ala Gln Ala Pro Ala  Ile Asn Thr
    1025                1030                1035 cgg ctt  gga gag gtt caa act  gga tgg gag gat ctt  cgg gca acc         3159
Arg Leu  Gly Glu Val Gln Thr  Gly Trp Glu Asp Leu  Arg Ala Thr
    1040                1045                1050 atg agg  cgg aga gaa gag tcc  ctg ggt gag gct cga  cgg ctg caa         3204
Met Arg  Arg Arg Glu Glu Ser  Leu Gly Glu Ala Arg  Arg Leu Gln
    1055                1060                1065 gat ttc  ctg cgc agc tta gat  gac ttc cag gcc tgg  cta ggc cgc         3249
Asp Phe  Leu Arg Ser Leu Asp  Asp Phe Gln Ala Trp  Leu Gly Arg
    1070                1075                1080 aca cag  act gct gta gcc tct  gag gaa gga cca gcc  acc ctt cca         3294
Thr Gln  Thr Ala Val Ala Ser  Glu Glu Gly Pro Ala  Thr Leu Pro
    1085                1090                1095 gag gca  gaa gcc ctc tta gcc  cag cat gca gct ctg  cgg gga gag         3339
Glu Ala  Glu Ala Leu Leu Ala  Gln His Ala Ala Leu  Arg Gly Glu
    1100                1105                1110
```

```
                                          -continued gtg gag aga gcc cag agc gag tac agc cgc ctc agg acc ttg ggc       3384
Val Glu Arg Ala Gln Ser Glu Tyr Ser Arg Leu Arg Thr Leu Gly
    1115                1120                1125 gag gag gtg acc aga gac cag gct gat ccc caa tgc ctc ttc ctc       3429
Glu Glu Val Thr Arg Asp Gln Ala Asp Pro Gln Cys Leu Phe Leu
1130                1135                1140 aga cag agg ctg gaa gcc ctt gga acc ggc tgg gag gag ctg ggt       3474
Arg Gln Arg Leu Glu Ala Leu Gly Thr Gly Trp Glu Glu Leu Gly
            1145                1150                1155 cgc atg tgg gag agc cgg caa ggc cgc ttg gcc caa gcc cat ggc       3519
Arg Met Trp Glu Ser Arg Gln Gly Arg Leu Ala Gln Ala His Gly
        1160                1165                1170 ttc cag ggg ttt ttg aga gat gct cgc cag gct gag gga gtt ctc       3564
Phe Gln Gly Phe Leu Arg Asp Ala Arg Gln Ala Glu Gly Val Leu
    1175                1180                1185 agc agc cag gaa tat gtt ctg tct cac acg gag atg cca ggg aca       3609
Ser Ser Gln Glu Tyr Val Leu Ser His Thr Glu Met Pro Gly Thr
1190                1195                1200 ctg cag gcg gcg gat gca gcc att aaa aag ctg gaa gac ttc atg       3654
Leu Gln Ala Ala Asp Ala Ala Ile Lys Lys Leu Glu Asp Phe Met
            1205                1210                1215 agc acc atg gac gcc aat gga gag cgc atc cgt gga ctc ctg gag       3699
Ser Thr Met Asp Ala Asn Gly Glu Arg Ile Arg Gly Leu Leu Glu
        1220                1225                1230 gct ggc cgt cag ctg gtg tcc aag ggc aat atc cat gct gag aag       3744
Ala Gly Arg Gln Leu Val Ser Lys Gly Asn Ile His Ala Glu Lys
    1235                1240                1245 atc caa gag aag gca gac tcc atc gag aag agg cac aga aag aac       3789
Ile Gln Glu Lys Ala Asp Ser Ile Glu Lys Arg His Arg Lys Asn
1250                1255                1260 cag gag gcc gtg cag cag ctt cta ggc cgc ctt cgg gac aac cga       3834
Gln Glu Ala Val Gln Gln Leu Leu Gly Arg Leu Arg Asp Asn Arg
            1265                1270                1275 gag cag cag cac ttc ttg caa gac tgt cag gag ctg aaa ctc tgg       3879
Glu Gln Gln His Phe Leu Gln Asp Cys Gln Glu Leu Lys Leu Trp
        1280                1285                1290 att gac gag aag atg ctg aca gct cag gat gtg tcc tat gat gag       3924
Ile Asp Glu Lys Met Leu Thr Ala Gln Asp Val Ser Tyr Asp Glu
    1295                1300                1305 gca cgc aac ctg cac acc aag tgg caa aaa cac cag gca ttc atg       3969
Ala Arg Asn Leu His Thr Lys Trp Gln Lys His Gln Ala Phe Met
1310                1315                1320 gcc gag ctg gca gcc aac aag gac tgg ctg gac aaa gtg gac aag       4014
Ala Glu Leu Ala Ala Asn Lys Asp Trp Leu Asp Lys Val Asp Lys
            1325                1330                1335 gaa ggg cgg gag ctg act ctt gaa aag cca gaa ctc aaa gtc cta       4059
Glu Gly Arg Glu Leu Thr Leu Glu Lys Pro Glu Leu Lys Val Leu
        1340                1345                1350 gtg tca gag aag ctg gag gac ctg cac agg cgc tgg gat gaa ctg       4104
Val Ser Glu Lys Leu Glu Asp Leu His Arg Arg Trp Asp Glu Leu
    1355                1360                1365 gag act acc acc caa gcc aag gcc cgc agt ctt ttt gat gct aac       4149
Glu Thr Thr Thr Gln Ala Lys Ala Arg Ser Leu Phe Asp Ala Asn
1370                1375                1380 cgg gca gag cta ttt gcc caa agc tgt tct gcc ctg gag agc tgg       4194
Arg Ala Glu Leu Phe Ala Gln Ser Cys Ser Ala Leu Glu Ser Trp
            1385                1390                1395 ctg gag agc ctg cag gcc cag ctg cac tca gat gac tat ggc aag       4239
Leu Glu Ser Leu Gln Ala Gln Leu His Ser Asp Asp Tyr Gly Lys
```

```
                                         -continued
        1400             1405             1410 gac ctc acc agt gtc aac att ctg cta aag aag caa cag atg ctg    4284
Asp Leu Thr Ser Val Asn Ile Leu Leu Lys Lys Gln Gln Met Leu
    1415             1420             1425 gaa cga gag atg gct gtg aga gag aag gag gta gag gct atc cag    4329
Glu Arg Glu Met Ala Val Arg Glu Lys Glu Val Glu Ala Ile Gln
    1430             1435             1440 gcc cag gca aaa gcc ctg gcc cag gaa gac caa agt gca gga gag    4374
Ala Gln Ala Lys Ala Leu Ala Gln Glu Asp Gln Ser Ala Gly Glu
    1445             1450             1455 gtg gaa agg acc tcc aga gct gtg gag gag aag ttc agg gcc ttg    4419
Val Glu Arg Thr Ser Arg Ala Val Glu Glu Lys Phe Arg Ala Leu
    1460             1465             1470 tgt cag ccc atg aag gac cgc tgc cgg cgc ctg caa gcc tcc cga    4464
Cys Gln Pro Met Lys Asp Arg Cys Arg Arg Leu Gln Ala Ser Arg
    1475             1480             1485 gag cag cac cag ttc cac cgg gat gtg gag gat gag ata ctg tgg    4509
Glu Gln His Gln Phe His Arg Asp Val Glu Asp Glu Ile Leu Trp
    1490             1495             1500 gtg acc gag cgg ctt ccc atg gcc agc tct ctg gag cat ggc aag    4554
Val Thr Glu Arg Leu Pro Met Ala Ser Ser Leu Glu His Gly Lys
    1505             1510             1515 gac ttg ccc agc gtc cag ctt ctc atg aag aaa aac cag act ctg    4599
Asp Leu Pro Ser Val Gln Leu Leu Met Lys Lys Asn Gln Thr Leu
    1520             1525             1530 cag aag gag atc cag ggc cat gag ccc cgg att gca gac ctc aaa    4644
Gln Lys Glu Ile Gln Gly His Glu Pro Arg Ile Ala Asp Leu Lys
    1535             1540             1545 gag agg cag cgc act ctg aga aca gca gca gcg ggt cca gag ctg    4689
Glu Arg Gln Arg Thr Leu Arg Thr Ala Ala Ala Gly Pro Glu Leu
    1550             1555             1560 gct gag ctc cag gaa atg tgg aaa cgc ctg agc cat gag ctg gag    4734
Ala Glu Leu Gln Glu Met Trp Lys Arg Leu Ser His Glu Leu Glu
    1565             1570             1575 ctt cgg ggt aaa cga ctg gag gag gcc ctt cga gcc cag caa ttc    4779
Leu Arg Gly Lys Arg Leu Glu Glu Ala Leu Arg Ala Gln Gln Phe
    1580             1585             1590 tat cgt gac gct gca gag gcc gag gct tgg atg ggg gag cag gag    4824
Tyr Arg Asp Ala Ala Glu Ala Glu Ala Trp Met Gly Glu Gln Glu
    1595             1600             1605 tta cat atg atg ggc cag gaa aag gcc aag gat gag ctg agc gcc    4869
Leu His Met Met Gly Gln Glu Lys Ala Lys Asp Glu Leu Ser Ala
    1610             1615             1620 cag gca gaa gtg aag aag cat cag gta cta gaa caa gcc ctt gct    4914
Gln Ala Glu Val Lys Lys His Gln Val Leu Glu Gln Ala Leu Ala
    1625             1630             1635 gac tat gcc cag acc atc aaa caa cta gca gcc agc agt caa gat    4959
Asp Tyr Ala Gln Thr Ile Lys Gln Leu Ala Ala Ser Ser Gln Asp
    1640             1645             1650 atg att gac cat gaa cat cca gag agc aca agg tta aca ata cgc    5004
Met Ile Asp His Glu His Pro Glu Ser Thr Arg Leu Thr Ile Arg
    1655             1660             1665 caa gcc cag gtg gac aag ctg tac gcc ggc cta aag gag ctg gca    5049
Gln Ala Gln Val Asp Lys Leu Tyr Ala Gly Leu Lys Glu Leu Ala
    1670             1675             1680 gga gag cgg cgt gag cgt ctg cag gag cac ctc agg ctg tgc cag    5094
Gly Glu Arg Arg Glu Arg Leu Gln Glu His Leu Arg Leu Cys Gln
    1685             1690             1695 ctc cgc aga gag ctg gat gac ctg gag cag tgg ata cag gag cga    5139
```

-continued

| | | | | | | | | | | | | |
|---|---|---|---|---|---|---|---|---|---|---|---|---|
| Leu | Arg | Arg | Glu | Leu | Asp | Asp | Leu | Glu | Gln | Trp | Ile | Gln | Glu | Arg |
| | 1700 | | | | 1705 | | | | 1710 | | | |

| gaa | gtc | gtg | gca | gcc | tcc | cat | gaa | ctg | ggc | cag | gac | tat | gag | cat | 5184 |
|---|---|---|---|---|---|---|---|---|---|---|---|---|---|---|---|
| Glu | Val | Val | Ala | Ala | Ser | His | Glu | Leu | Gly | Gln | Asp | Tyr | Glu | His |
| | 1715 | | | | 1720 | | | | 1725 |

| gtg | act | atg | ctt | cgg | gac | aaa | ttc | cga | gag | ttc | tcc | agg | gac | acc | 5229 |
|---|---|---|---|---|---|---|---|---|---|---|---|---|---|---|---|
| Val | Thr | Met | Leu | Arg | Asp | Lys | Phe | Arg | Glu | Phe | Ser | Arg | Asp | Thr |
| 1730 | | | | 1735 | | | | 1740 |

| agc | acc | att | ggc | caa | gag | cgt | gta | gac | agt | gcc | aat | gcc | ctg | gcc | 5274 |
|---|---|---|---|---|---|---|---|---|---|---|---|---|---|---|---|
| Ser | Thr | Ile | Gly | Gln | Glu | Arg | Val | Asp | Ser | Ala | Asn | Ala | Leu | Ala |
| 1745 | | | | 1750 | | | | 1755 |

| aat | ggg | ctc | att | gct | ggg | ggc | cat | gct | gca | tgg | gcc | acc | gtg | gcc | 5319 |
|---|---|---|---|---|---|---|---|---|---|---|---|---|---|---|---|
| Asn | Gly | Leu | Ile | Ala | Gly | Gly | His | Ala | Ala | Trp | Ala | Thr | Val | Ala |
| 1760 | | | | 1765 | | | | 1770 |

| gag | tgg | aag | gac | agt | ctc | aat | gag | gcc | tgg | gct | gac | ctg | ctg | gag | 5364 |
|---|---|---|---|---|---|---|---|---|---|---|---|---|---|---|---|
| Glu | Trp | Lys | Asp | Ser | Leu | Asn | Glu | Ala | Trp | Ala | Asp | Leu | Leu | Glu |
| 1775 | | | | 1780 | | | | 1785 |

| ctg | ctg | gac | aca | aga | ggt | cag | gtg | ctg | gct | gct | gct | tat | gag | ctg | 5409 |
|---|---|---|---|---|---|---|---|---|---|---|---|---|---|---|---|
| Leu | Leu | Asp | Thr | Arg | Gly | Gln | Val | Leu | Ala | Ala | Ala | Tyr | Glu | Leu |
| 1790 | | | | 1795 | | | | 1800 |

| cag | cgc | ttc | ctg | cat | ggg | gcc | cgc | caa | gcc | ctg | gca | cgg | gtg | cag | 5454 |
|---|---|---|---|---|---|---|---|---|---|---|---|---|---|---|---|
| Gln | Arg | Phe | Leu | His | Gly | Ala | Arg | Gln | Ala | Leu | Ala | Arg | Val | Gln |
| 1805 | | | | 1810 | | | | 1815 |

| cac | aag | cag | cag | cag | ctt | cca | gat | ggg | acg | ggc | cgc | gac | ctc | aat | 5499 |
|---|---|---|---|---|---|---|---|---|---|---|---|---|---|---|---|
| His | Lys | Gln | Gln | Gln | Leu | Pro | Asp | Gly | Thr | Gly | Arg | Asp | Leu | Asn |
| 1820 | | | | 1825 | | | | 1830 |

| gct | gct | gag | gcc | ctg | cag | cgc | cgg | cac | tgc | gcc | tat | gag | cac | gac | 5544 |
|---|---|---|---|---|---|---|---|---|---|---|---|---|---|---|---|
| Ala | Ala | Glu | Ala | Leu | Gln | Arg | Arg | His | Cys | Ala | Tyr | Glu | His | Asp |
| 1835 | | | | 1840 | | | | 1845 |

| atc | caa | gcc | ctc | agc | act | cag | gtc | cag | cag | gtt | cag | gac | gat | ggc | 5589 |
|---|---|---|---|---|---|---|---|---|---|---|---|---|---|---|---|
| Ile | Gln | Ala | Leu | Ser | Thr | Gln | Val | Gln | Gln | Val | Gln | Asp | Asp | Gly |
| 1850 | | | | 1855 | | | | 1860 |

| ctc | agg | cta | caa | aag | gcc | tat | gct | gga | gac | aag | gct | gag | gaa | att | 5634 |
|---|---|---|---|---|---|---|---|---|---|---|---|---|---|---|---|
| Leu | Arg | Leu | Gln | Lys | Ala | Tyr | Ala | Gly | Asp | Lys | Ala | Glu | Glu | Ile |
| 1865 | | | | 1870 | | | | 1875 |

| ggc | cgt | cac | atg | cag | gca | gtg | gct | gag | gcg | tgg | gcc | cag | ctc | cag | 5679 |
|---|---|---|---|---|---|---|---|---|---|---|---|---|---|---|---|
| Gly | Arg | His | Met | Gln | Ala | Val | Ala | Glu | Ala | Trp | Ala | Gln | Leu | Gln |
| 1880 | | | | 1885 | | | | 1890 |

| gga | agt | tct | gct | gcc | cgt | cgc | cag | ctg | tta | ctg | gat | acc | aca | gac | 5724 |
|---|---|---|---|---|---|---|---|---|---|---|---|---|---|---|---|
| Gly | Ser | Ser | Ala | Ala | Arg | Arg | Gln | Leu | Leu | Leu | Asp | Thr | Thr | Asp |
| 1895 | | | | 1900 | | | | 1905 |

| aaa | ttc | cga | ttc | ttc | aag | gct | gtc | cgg | gag | ttg | atg | ctg | tgg | atg | 5769 |
|---|---|---|---|---|---|---|---|---|---|---|---|---|---|---|---|
| Lys | Phe | Arg | Phe | Phe | Lys | Ala | Val | Arg | Glu | Leu | Met | Leu | Trp | Met |
| 1910 | | | | 1915 | | | | 1920 |

| gat | ggg | att | aac | ctg | cag | atg | gat | gcc | cag | gag | agg | ccc | cgg | gat | 5814 |
|---|---|---|---|---|---|---|---|---|---|---|---|---|---|---|---|
| Asp | Gly | Ile | Asn | Leu | Gln | Met | Asp | Ala | Gln | Glu | Arg | Pro | Arg | Asp |
| 1925 | | | | 1930 | | | | 1935 |

| gtg | tcc | tct | gca | gat | tta | gtc | atc | aaa | aac | caa | caa | ggc | atc | aaa | 5859 |
|---|---|---|---|---|---|---|---|---|---|---|---|---|---|---|---|
| Val | Ser | Ser | Ala | Asp | Leu | Val | Ile | Lys | Asn | Gln | Gln | Gly | Ile | Lys |
| 1940 | | | | 1945 | | | | 1950 |

| gca | gag | ata | gag | gca | aga | gct | gac | agg | ttc | tcc | gcc | tgc | att | gac | 5904 |
|---|---|---|---|---|---|---|---|---|---|---|---|---|---|---|---|
| Ala | Glu | Ile | Glu | Ala | Arg | Ala | Asp | Arg | Phe | Ser | Ala | Cys | Ile | Asp |
| 1955 | | | | 1960 | | | | 1965 |

| atg | ggg | caa | gag | ctg | ctg | gcc | cgg | aac | cac | tat | gcc | gct | gag | gag | 5949 |
|---|---|---|---|---|---|---|---|---|---|---|---|---|---|---|---|
| Met | Gly | Gln | Glu | Leu | Leu | Ala | Arg | Asn | His | Tyr | Ala | Ala | Glu | Glu |
| 1970 | | | | 1975 | | | | 1980 |

| atc | tca | gag | aag | ctg | tct | cag | cta | cag | tcc | cgg | cgc | cag | gag | aca | 5994 |
|---|---|---|---|---|---|---|---|---|---|---|---|---|---|---|---|
| Ile | Ser | Glu | Lys | Leu | Ser | Gln | Leu | Gln | Ser | Arg | Arg | Gln | Glu | Thr |
| 1985 | | | | 1990 | | | | 1995 |

```
                                                    -continued gct gaa aag tgg cag gag aag atg gac tgg cta cag ctt gtt ttg         6039
Ala Glu Lys Trp Gln Glu Lys Met Asp Trp Leu Gln Leu Val Leu
    2000            2005            2010 gag gtg ctt gtg ttt ggg aga gat gca ggc atg gca gag gcc tgg         6084
Glu Val Leu Val Phe Gly Arg Asp Ala Gly Met Ala Glu Ala Trp
    2015            2020            2025 cta tgc agt cag gag cca ttg gtg cga agt gca gaa ctg ggt tgc         6129
Leu Cys Ser Gln Glu Pro Leu Val Arg Ser Ala Glu Leu Gly Cys
    2030            2035            2040 act gtg gat gaa gta gag agc ctc atc aag cgg cat gaa gcc ttc         6174
Thr Val Asp Glu Val Glu Ser Leu Ile Lys Arg His Glu Ala Phe
    2045            2050            2055 cag aag tca gca gtg gcc tgg gag gag cgt ttc agt gcc ctg gag         6219
Gln Lys Ser Ala Val Ala Trp Glu Glu Arg Phe Ser Ala Leu Glu
    2060            2065            2070 aag ctc act gcg ctg gaa gag cgg gag aat gag cag aaa agg aag         6264
Lys Leu Thr Ala Leu Glu Glu Arg Glu Asn Glu Gln Lys Arg Lys
    2075            2080            2085 agg gag gag gag gaa cga agg aaa cag ccc cct act tca gag ccc         6309
Arg Glu Glu Glu Glu Arg Arg Lys Gln Pro Pro Thr Ser Glu Pro
    2090            2095            2100 atg gct agt caa ccg gaa ggg agt ctg gta gat ggc cag aga gtt         6354
Met Ala Ser Gln Pro Glu Gly Ser Leu Val Asp Gly Gln Arg Val
    2105            2110            2115 ctt gac act gcc tgg gat ggg acc cag tca aaa ttg cca cca tcc         6399
Leu Asp Thr Ala Trp Asp Gly Thr Gln Ser Lys Leu Pro Pro Ser
    2120            2125            2130 aca caa gca ccc agc att aat ggg gtc tgc acg gac acg gag tcc         6444
Thr Gln Ala Pro Ser Ile Asn Gly Val Cys Thr Asp Thr Glu Ser
    2135            2140            2145 tca cag cct ctg ttg gaa cag caa aga ctt gaa cag agc aat gtc         6489
Ser Gln Pro Leu Leu Glu Gln Gln Arg Leu Glu Gln Ser Asn Val
    2150            2155            2160 cca gaa ggg cct gga tct ggc aca gga gac gag tcc agc ggg ccc         6534
Pro Glu Gly Pro Gly Ser Gly Thr Gly Asp Glu Ser Ser Gly Pro
    2165            2170            2175 cgg gga gag agg cag acc ctg ccc cgg ggc cct gct ccg tct cca         6579
Arg Gly Glu Arg Gln Thr Leu Pro Arg Gly Pro Ala Pro Ser Pro
    2180            2185            2190 atg ccc cag agc aga tcg tct gag tca gct cat gtt gcc acc ctg         6624
Met Pro Gln Ser Arg Ser Ser Glu Ser Ala His Val Ala Thr Leu
    2195            2200            2205 ccc gca cga ggt gct gag ctc tct gct cag gaa cag atg gaa ggg         6669
Pro Ala Arg Gly Ala Glu Leu Ser Ala Gln Glu Gln Met Glu Gly
    2210            2215            2220 acg ctg tgc cgc aaa cag gag atg gaa gcc ttc aat aag aaa gct         6714
Thr Leu Cys Arg Lys Gln Glu Met Glu Ala Phe Asn Lys Lys Ala
    2225            2230            2235 gcc aac agg tcc tgg cag aat gtg tac tgt gta ctt cgg cgt gga         6759
Ala Asn Arg Ser Trp Gln Asn Val Tyr Cys Val Leu Arg Arg Gly
    2240            2245            2250 agc ctc ggc ttt tac aag gat gcc agg gca gct agt gca gga gtg         6804
Ser Leu Gly Phe Tyr Lys Asp Ala Arg Ala Ala Ser Ala Gly Val
    2255            2260            2265 cca tac cat gga gaa gtg cct gtc agt ctg gcc agg gcc cag ggc         6849
Pro Tyr His Gly Glu Val Pro Val Ser Leu Ala Arg Ala Gln Gly
    2270            2275            2280 agt gtg gcc ttt gat tat cgg aaa cgc aaa cat gtc ttc aag ctg         6894
Ser Val Ala Phe Asp Tyr Arg Lys Arg Lys His Val Phe Lys Leu
    2285            2290            2295
```

```
ggc ttg cag gat ggg aaa gag tat cta ttc cag gcc aag gat gag        6939
Gly Leu Gln Asp Gly Lys Glu Tyr Leu Phe Gln Ala Lys Asp Glu
        2300                2305                2310 gca gag atg agc tca tgg ctg aga gtg gtg aat gca gcc att gcc        6984
Ala Glu Met Ser Ser Trp Leu Arg Val Val Asn Ala Ala Ile Ala
    2315                2320                2325 act gcg tcc tcg gcc tct gga gag cca gaa gag cca gtg gtg ccc        7029
Thr Ala Ser Ser Ala Ser Gly Glu Pro Glu Glu Pro Val Val Pro
2330                2335                2340 agt gcc agc cgg ggt ctg acc agg gcc atg acc atg ccc cca gtg        7074
Ser Ala Ser Arg Gly Leu Thr Arg Ala Met Thr Met Pro Pro Val
    2345                2350                2355 tca cag cct gag ggc tcc atc gtg ctt cgc agc aag gat ggc aga        7119
Ser Gln Pro Glu Gly Ser Ile Val Leu Arg Ser Lys Asp Gly Arg
        2360                2365                2370 gaa aga gag cga gaa aaa cga ttc agc ttc ttt aag aag aac aag        7164
Glu Arg Glu Arg Glu Lys Arg Phe Ser Phe Phe Lys Lys Asn Lys
    2375                2380                2385 tagttggggc aagactccca ggccagctcc ctccctctgt tcaggaaact gccagggact   7224
gtcgacagag accacc                                                  7240

<210> SEQ ID NO 2
<211> LENGTH: 2388
<212> TYPE: PRT
<213> ORGANISM: Rattus

<400> SEQUENCE: 2

Met Ser Ser Thr Leu Ser Pro Thr Asp Phe Asp Ser Leu Glu Ile Gln
1               5                   10                  15

Gly Gln Tyr Ser Asp Ile Asn Asn Arg Trp Asp Leu Pro Ser Asp
            20                  25                  30

Trp Asp Asn Asp Ser Ser Ala Arg Leu Phe Glu Arg Ser Arg Ile
        35                  40                  45

Lys Ala Leu Ala Asp Glu Arg Glu Ala Val Gln Lys Lys Thr Phe Thr
50                  55                  60

Lys Trp Val Asn Ser His Leu Ala Arg Val Thr Cys Arg Val Gly Asp
65                  70                  75                  80

Leu Tyr Ser Asp Leu Arg Asp Gly Arg Asn Leu Leu Arg Leu Leu Glu
                85                  90                  95

Val Leu Ser Gly Glu Thr Leu Pro Lys Pro Thr Lys Gly Arg Met Arg
            100                 105                 110

Ile His Cys Leu Glu Asn Val Asp Lys Ala Leu Gln Phe Leu Lys Glu
        115                 120                 125

Gln Lys Val His Leu Glu Asn Met Gly Ser His Asp Ile Val Asp Gly
    130                 135                 140

Asn His Arg Leu Thr Leu Gly Leu Val Trp Thr Ile Ile Leu Arg Phe
145                 150                 155                 160

Gln Ile Gln Asp Ile Ser Val Glu Thr Glu Asp Asn Lys Glu Lys Lys
                165                 170                 175

Ser Ala Lys Asp Ala Leu Leu Leu Trp Cys Gln Met Lys Thr Ala Gly
            180                 185                 190

Tyr Pro Asn Val Asn Val His Asn Phe Thr Thr Ser Trp Arg Asp Gly
        195                 200                 205

Leu Ala Phe Asn Ala Ile Val His Lys His Arg Pro Asp Leu Leu Asp
    210                 215                 220
```

-continued

```
Phe Glu Ser Leu Lys Lys Cys Asn Ala His Tyr Asn Leu Gln Asn Ala
225                 230                 235                 240

Phe Asn Leu Ala Glu Lys Glu Leu Gly Leu Thr Lys Leu Leu Asp Pro
            245                 250                 255

Glu Asp Val Asn Val Asp Gln Pro Asp Glu Lys Ser Ile Ile Thr Tyr
                260                 265                 270

Val Ala Thr Tyr Tyr His Tyr Phe Ser Lys Met Lys Ala Leu Ala Val
            275                 280                 285

Glu Gly Lys Arg Ile Gly Lys Val Leu Asp His Ala Met Glu Ala Glu
        290                 295                 300

His Leu Val Glu Lys Tyr Glu Ser Leu Ala Ser Glu Leu Leu Gln Trp
305                 310                 315                 320

Ile Glu Gln Thr Ile Gly Thr Phe Asn Asp Arg Gln Leu Ala Asn Ser
                325                 330                 335

Leu Ser Gly Val Gln Asn Gln Leu Gln Ser Phe Asn Ser Tyr Arg Thr
            340                 345                 350

Val Glu Lys Pro Pro Lys Phe Thr Glu Lys Gly Asn Leu Glu Val Leu
        355                 360                 365

Leu Phe Thr Ile Gln Ser Lys Leu Arg Ala Asn Asn Gln Lys Val Tyr
370                 375                 380

Thr Pro Arg Glu Gly Arg Leu Ile Ser Asp Ile Asn Lys Ala Trp Glu
385                 390                 395                 400

Arg Leu Glu Lys Ala Glu His Glu Arg Glu Leu Ala Leu Arg Thr Glu
                405                 410                 415

Leu Ile Arg Gln Glu Lys Leu Glu Gln Leu Ala Ala Arg Phe Asp Arg
            420                 425                 430

Lys Ala Ala Met Arg Glu Thr Trp Leu Ser Glu Asn Gln Arg Leu Val
        435                 440                 445

Ser Gln Asp Asn Phe Gly Leu Glu Leu Ala Ala Val Glu Ala Ala Val
450                 455                 460

Arg Lys His Glu Ala Ile Glu Thr Asp Ile Val Ala Tyr Ser Gly Arg
465                 470                 475                 480

Val Gln Ala Val Asp Ala Val Ala Ala Glu Leu Ala Ala Glu His Tyr
                485                 490                 495

His Asp Ile Lys Arg Ile Ala Ala Arg Gln Asn Asn Val Ala Arg Leu
            500                 505                 510

Trp Asp Phe Leu Arg Glu Met Val Ala Ala Arg Arg Glu Arg Leu Leu
        515                 520                 525

Leu Asn Leu Glu Leu Gln Lys Val Phe Gln Asp Leu Leu Tyr Leu Met
530                 535                 540

Asp Trp Met Ala Glu Met Lys Gly Arg Leu Gln Ser Gln Asp Leu Gly
545                 550                 555                 560

Lys His Leu Ala Gly Val Glu Asp Leu Leu Gln Leu His Glu Leu Val
                565                 570                 575

Glu Ala Asp Ile Ala Val Gln Ala Glu Arg Val Arg Ala Val Ser Ala
            580                 585                 590

Ser Ala Leu Arg Phe Cys Asp Pro Gly Lys Glu Tyr Arg Pro Cys Gly
        595                 600                 605

Pro Gln Leu Val Ser Glu Arg Val Ala Thr Leu Glu Gln Ser Tyr Glu
610                 615                 620

Ala Leu Cys Glu Leu Ala Ala Thr Arg Ala Arg Leu Glu Glu Ser
625                 630                 635                 640

Arg Arg Leu Trp Arg Phe Leu Trp Glu Val Gly Glu Ala Glu Ala Trp
```

-continued

```
                645                 650                 655
Val Arg Glu Gln Gln His Leu Leu Ala Ser Ala Glu Thr Gly Arg Asp
            660                 665                 670
Leu Thr Gly Val Leu Arg Leu Leu Asn Lys His Thr Ala Leu Arg Gly
            675                 680                 685
Glu Met Ser Gly Arg Leu Gly Pro Leu Lys Leu Thr Leu Glu Gln Gly
            690                 695                 700
Gln Gln Leu Val Ala Glu Gly His Pro Gly Ala Asn Gln Ala Ser Thr
705                 710                 715                 720
Arg Ala Ala Glu Leu Gln Ala Gln Trp Glu Arg Leu Glu Ala Leu Ala
            725                 730                 735
Glu Glu Arg Ala Gln Arg Leu Ala Gln Ala Ala Ser Leu Tyr Gln Phe
            740                 745                 750
Gln Ala Asp Ala Asn Asp Met Glu Ala Trp Leu Val Asp Ala Leu Arg
            755                 760                 765
Leu Val Ser Ser Pro Glu Val Gly His Asp Glu Phe Ser Thr Gln Ala
            770                 775                 780
Leu Ala Arg Gln His Arg Ala Leu Glu Glu Ile Arg Ala His Arg
785                 790                 795                 800
Pro Thr Leu Asp Ala Leu Arg Glu Gln Ala Ala Ala Leu Pro Pro Ala
            805                 810                 815
Leu Ser His Thr Pro Glu Val Gln Gly Arg Val Pro Thr Leu Glu Gln
            820                 825                 830
His Tyr Glu Glu Leu Gln Ala Arg Ala Gly Glu Arg Ala Arg Ala Leu
            835                 840                 845
Glu Ala Ala Leu Ala Phe Tyr Thr Met Leu Ser Glu Ala Gly Ala Cys
850                 855                 860
Gly Leu Trp Val Glu Glu Lys Glu Gln Trp Leu Asn Gly Leu Ala Leu
865                 870                 875                 880
Pro Glu Arg Leu Glu Asp Pro Glu Val Val Gln Gln Arg Phe Glu Thr
            885                 890                 895
Leu Glu Pro Glu Met Asn Ala Leu Ala Ala Arg Ile Thr Ala Val Ser
            900                 905                 910
Asp Ile Ala Glu Gln Leu Leu Lys Ala Ser Pro Pro Gly Lys Asp Arg
            915                 920                 925
Ile Ile Gly Thr Gln Glu Gln Leu Asn Gln Arg Trp Gln Gln Phe Arg
930                 935                 940
Ser Leu Ala Gly Gly Lys Lys Ala Ala Leu Thr Ser Ala Leu Ser Ile
945                 950                 955                 960
Gln Asn Tyr His Leu Glu Cys Thr Glu Thr Gln Ala Trp Met Arg Glu
            965                 970                 975
Lys Thr Lys Val Ile Glu Ser Thr Gln Asp Leu Gly Asn Asp Leu Ala
            980                 985                 990
Gly Val Leu Ala Leu Gln Arg Lys  Leu Ala Gly Thr Glu  Arg Asp Leu
            995                 1000                 1005
Glu Ala Ile Ser Ala Arg Val  Gly Glu Leu Thr Gln  Glu Ala Asn
            1010                 1015                 1020
Ala Leu Ala Ala Gly His Pro  Ala Gln Ala Pro Ala  Ile Asn Thr
            1025                 1030                 1035
Arg Leu Gly Glu Val Gln Thr  Gly Trp Glu Asp Leu  Arg Ala Thr
            1040                 1045                 1050
Met Arg Arg Arg Glu Glu Ser  Leu Gly Glu Ala Arg  Arg Leu Gln
            1055                 1060                 1065
```

-continued

```
Asp Phe Leu Arg Ser Leu Asp Asp Phe Gln Ala Trp Leu Gly Arg
    1070            1075            1080

Thr Gln Thr Ala Val Ala Ser Glu Glu Gly Pro Ala Thr Leu Pro
    1085            1090            1095

Glu Ala Glu Ala Leu Leu Ala Gln His Ala Ala Leu Arg Gly Glu
    1100            1105            1110

Val Glu Arg Ala Gln Ser Glu Tyr Ser Arg Leu Arg Thr Leu Gly
    1115            1120            1125

Glu Glu Val Thr Arg Asp Gln Ala Asp Pro Gln Cys Leu Phe Leu
    1130            1135            1140

Arg Gln Arg Leu Glu Ala Leu Gly Thr Gly Trp Glu Glu Leu Gly
    1145            1150            1155

Arg Met Trp Glu Ser Arg Gln Gly Arg Leu Ala Gln Ala His Gly
    1160            1165            1170

Phe Gln Gly Phe Leu Arg Asp Ala Arg Gln Ala Glu Gly Val Leu
    1175            1180            1185

Ser Ser Gln Glu Tyr Val Leu Ser His Thr Glu Met Pro Gly Thr
    1190            1195            1200

Leu Gln Ala Ala Asp Ala Ala Ile Lys Lys Leu Glu Asp Phe Met
    1205            1210            1215

Ser Thr Met Asp Ala Asn Gly Glu Arg Ile Arg Gly Leu Leu Glu
    1220            1225            1230

Ala Gly Arg Gln Leu Val Ser Lys Gly Asn Ile His Ala Glu Lys
    1235            1240            1245

Ile Gln Glu Lys Ala Asp Ser Ile Glu Lys Arg His Arg Lys Asn
    1250            1255            1260

Gln Glu Ala Val Gln Gln Leu Leu Gly Arg Leu Arg Asp Asn Arg
    1265            1270            1275

Glu Gln Gln His Phe Leu Gln Asp Cys Gln Glu Leu Lys Leu Trp
    1280            1285            1290

Ile Asp Glu Lys Met Leu Thr Ala Gln Asp Val Ser Tyr Asp Glu
    1295            1300            1305

Ala Arg Asn Leu His Thr Lys Trp Gln Lys His Gln Ala Phe Met
    1310            1315            1320

Ala Glu Leu Ala Ala Asn Lys Asp Trp Leu Asp Lys Val Asp Lys
    1325            1330            1335

Glu Gly Arg Glu Leu Thr Leu Glu Lys Pro Glu Leu Lys Val Leu
    1340            1345            1350

Val Ser Glu Lys Leu Glu Asp Leu His Arg Arg Trp Asp Glu Leu
    1355            1360            1365

Glu Thr Thr Thr Gln Ala Lys Ala Arg Ser Leu Phe Asp Ala Asn
    1370            1375            1380

Arg Ala Glu Leu Phe Ala Gln Ser Cys Ser Ala Leu Glu Ser Trp
    1385            1390            1395

Leu Glu Ser Leu Gln Ala Gln Leu His Ser Asp Asp Tyr Gly Lys
    1400            1405            1410

Asp Leu Thr Ser Val Asn Ile Leu Leu Lys Lys Gln Gln Met Leu
    1415            1420            1425

Glu Arg Glu Met Ala Val Arg Glu Lys Glu Val Glu Ala Ile Gln
    1430            1435            1440

Ala Gln Ala Lys Ala Leu Ala Gln Glu Asp Gln Ser Ala Gly Glu
    1445            1450            1455
```

-continued

| | | | | | | | | | | | |
|---|---|---|---|---|---|---|---|---|---|---|---|
|Val|Glu|Arg|Thr|Ser|Arg|Ala|Val|Glu|Lys|Phe|Arg|Ala|Leu|
|1460| | | | |1465| | | |1470| | |
|Cys|Gln|Pro|Met|Lys|Asp|Arg|Cys|Arg|Arg|Leu|Gln|Ala|Ser|Arg|
|1475| | | | |1480| | | |1485| | |
|Glu|Gln|His|Gln|Phe|His|Arg|Asp|Val|Glu|Asp|Glu|Ile|Leu|Trp|
|1490| | | | |1495| | | |1500| | |
|Val|Thr|Glu|Arg|Leu|Pro|Met|Ala|Ser|Ser|Leu|Glu|His|Gly|Lys|
|1505| | | | |1510| | | |1515| | |
|Asp|Leu|Pro|Ser|Val|Gln|Leu|Leu|Met|Lys|Lys|Asn|Gln|Thr|Leu|
|1520| | | | |1525| | | |1530| | |
|Gln|Lys|Glu|Ile|Gln|Gly|His|Glu|Pro|Arg|Ile|Ala|Asp|Leu|Lys|
|1535| | | | |1540| | | |1545| | |
|Glu|Arg|Gln|Arg|Thr|Leu|Arg|Thr|Ala|Ala|Ala|Gly|Pro|Glu|Leu|
|1550| | | | |1555| | | |1560| | |
|Ala|Glu|Leu|Gln|Glu|Met|Trp|Lys|Arg|Leu|Ser|His|Glu|Leu|Glu|
|1565| | | | |1570| | | |1575| | |
|Leu|Arg|Gly|Lys|Arg|Leu|Glu|Glu|Ala|Leu|Arg|Ala|Gln|Gln|Phe|
|1580| | | | |1585| | | |1590| | |
|Tyr|Arg|Asp|Ala|Ala|Glu|Ala|Glu|Ala|Trp|Met|Gly|Glu|Gln|Glu|
|1595| | | | |1600| | | |1605| | |
|Leu|His|Met|Met|Gly|Gln|Glu|Lys|Ala|Lys|Asp|Glu|Leu|Ser|Ala|
|1610| | | | |1615| | | |1620| | |
|Gln|Ala|Glu|Val|Lys|Lys|His|Gln|Val|Leu|Glu|Gln|Ala|Leu|Ala|
|1625| | | | |1630| | | |1635| | |
|Asp|Tyr|Ala|Gln|Thr|Ile|Lys|Gln|Leu|Ala|Ala|Ser|Ser|Gln|Asp|
|1640| | | | |1645| | | |1650| | |
|Met|Ile|Asp|His|Glu|His|Pro|Glu|Ser|Thr|Arg|Leu|Thr|Ile|Arg|
|1655| | | | |1660| | | |1665| | |
|Gln|Ala|Gln|Val|Asp|Lys|Leu|Tyr|Ala|Gly|Leu|Lys|Glu|Leu|Ala|
|1670| | | | |1675| | | |1680| | |
|Gly|Glu|Arg|Arg|Glu|Arg|Leu|Gln|Glu|His|Leu|Arg|Leu|Cys|Gln|
|1685| | | | |1690| | | |1695| | |
|Leu|Arg|Arg|Glu|Leu|Asp|Asp|Leu|Glu|Gln|Trp|Ile|Gln|Glu|Arg|
|1700| | | | |1705| | | |1710| | |
|Glu|Val|Val|Ala|Ala|Ser|His|Glu|Leu|Gly|Gln|Asp|Tyr|Glu|His|
|1715| | | | |1720| | | |1725| | |
|Val|Thr|Met|Leu|Arg|Asp|Lys|Phe|Arg|Glu|Phe|Ser|Arg|Asp|Thr|
|1730| | | | |1735| | | |1740| | |
|Ser|Thr|Ile|Gly|Gln|Glu|Arg|Val|Asp|Ser|Ala|Asn|Ala|Leu|Ala|
|1745| | | | |1750| | | |1755| | |
|Asn|Gly|Leu|Ile|Ala|Gly|Gly|His|Ala|Ala|Trp|Ala|Thr|Val|Ala|
|1760| | | | |1765| | | |1770| | |
|Glu|Trp|Lys|Asp|Ser|Leu|Asn|Glu|Ala|Trp|Ala|Asp|Leu|Leu|Glu|
|1775| | | | |1780| | | |1785| | |
|Leu|Leu|Asp|Thr|Arg|Gly|Gln|Val|Leu|Ala|Ala|Ala|Tyr|Glu|Leu|
|1790| | | | |1795| | | |1800| | |
|Gln|Arg|Phe|Leu|His|Gly|Ala|Arg|Gln|Ala|Leu|Ala|Arg|Val|Gln|
|1805| | | | |1810| | | |1815| | |
|His|Lys|Gln|Gln|Gln|Leu|Pro|Asp|Gly|Thr|Gly|Arg|Asp|Leu|Asn|
|1820| | | | |1825| | | |1830| | |
|Ala|Ala|Glu|Ala|Leu|Gln|Arg|Arg|His|Cys|Ala|Tyr|Glu|His|Asp|
|1835| | | | |1840| | | |1845| | |
|Ile|Gln|Ala|Leu|Ser|Thr|Gln|Val|Gln|Gln|Val|Gln|Asp|Asp|Gly|

-continued

```
        1850                1855                1860
Leu Arg Leu Gln Lys Ala Tyr Ala Gly Asp Lys Ala Glu Glu Ile
        1865                1870                1875
Gly Arg His Met Gln Ala Val Ala Glu Ala Trp Ala Gln Leu Gln
        1880                1885                1890
Gly Ser Ser Ala Ala Arg Arg Gln Leu Leu Asp Thr Thr Asp
        1895                1900                1905
Lys Phe Arg Phe Phe Lys Ala Val Arg Glu Leu Met Leu Trp Met
        1910                1915                1920
Asp Gly Ile Asn Leu Gln Met Asp Ala Gln Glu Arg Pro Arg Asp
        1925                1930                1935
Val Ser Ser Ala Asp Leu Val Ile Lys Asn Gln Gln Gly Ile Lys
        1940                1945                1950
Ala Glu Ile Glu Ala Arg Ala Asp Arg Phe Ser Ala Cys Ile Asp
        1955                1960                1965
Met Gly Gln Glu Leu Leu Ala Arg Asn His Tyr Ala Ala Glu Glu
        1970                1975                1980
Ile Ser Glu Lys Leu Ser Gln Leu Gln Ser Arg Arg Gln Glu Thr
        1985                1990                1995
Ala Glu Lys Trp Gln Glu Lys Met Asp Trp Leu Gln Leu Val Leu
        2000                2005                2010
Glu Val Leu Val Phe Gly Arg Asp Ala Gly Met Ala Glu Ala Trp
        2015                2020                2025
Leu Cys Ser Gln Glu Pro Leu Val Arg Ser Ala Glu Leu Gly Cys
        2030                2035                2040
Thr Val Asp Glu Val Glu Ser Leu Ile Lys Arg His Glu Ala Phe
        2045                2050                2055
Gln Lys Ser Ala Val Ala Trp Glu Glu Arg Phe Ser Ala Leu Glu
        2060                2065                2070
Lys Leu Thr Ala Leu Glu Glu Arg Glu Asn Glu Gln Lys Arg Lys
        2075                2080                2085
Arg Glu Glu Glu Glu Arg Arg Lys Gln Pro Pro Thr Ser Glu Pro
        2090                2095                2100
Met Ala Ser Gln Pro Glu Gly Ser Leu Val Asp Gly Gln Arg Val
        2105                2110                2115
Leu Asp Thr Ala Trp Asp Gly Thr Gln Ser Lys Leu Pro Pro Ser
        2120                2125                2130
Thr Gln Ala Pro Ser Ile Asn Gly Val Cys Thr Asp Thr Glu Ser
        2135                2140                2145
Ser Gln Pro Leu Leu Glu Gln Arg Leu Glu Gln Ser Asn Val
        2150                2155                2160
Pro Glu Gly Pro Gly Ser Gly Thr Gly Asp Glu Ser Ser Gly Pro
        2165                2170                2175
Arg Gly Glu Arg Gln Thr Leu Pro Arg Gly Pro Ala Pro Ser Pro
        2180                2185                2190
Met Pro Gln Ser Arg Ser Ser Glu Ser Ala His Val Ala Thr Leu
        2195                2200                2205
Pro Ala Arg Gly Ala Glu Leu Ser Ala Gln Glu Gln Met Glu Gly
        2210                2215                2220
Thr Leu Cys Arg Lys Gln Glu Met Glu Ala Phe Asn Lys Lys Ala
        2225                2230                2235
Ala Asn Arg Ser Trp Gln Asn Val Tyr Cys Val Leu Arg Arg Gly
        2240                2245                2250
```

| Ser | Leu | Gly | Phe | Tyr | Lys | Asp | Ala | Arg | Ala | Ala | Ser | Ala | Gly | Val |
| | | 2255 | | | | 2260 | | | | 2265 | | | | |

| Pro | Tyr | His | Gly | Glu | Val | Pro | Val | Ser | Leu | Ala | Arg | Ala | Gln | Gly |
| | 2270 | | | | 2275 | | | | | 2280 | | | | |

| Ser | Val | Ala | Phe | Asp | Tyr | Arg | Lys | Arg | Lys | His | Val | Phe | Lys | Leu |
| | | 2285 | | | | 2290 | | | | 2295 | | | | |

| Gly | Leu | Gln | Asp | Gly | Lys | Glu | Tyr | Leu | Phe | Gln | Ala | Lys | Asp | Glu |
| | 2300 | | | | 2305 | | | | | 2310 | | | | |

| Ala | Glu | Met | Ser | Ser | Trp | Leu | Arg | Val | Val | Asn | Ala | Ala | Ile | Ala |
| | 2315 | | | | 2320 | | | | | 2325 | | | | |

| Thr | Ala | Ser | Ser | Ala | Ser | Gly | Glu | Pro | Glu | Pro | Val | Val | Pro |
| | 2330 | | | | | 2335 | | | | 2340 | | | | |

| Ser | Ala | Ser | Arg | Gly | Leu | Thr | Arg | Ala | Met | Thr | Met | Pro | Pro | Val |
| | 2345 | | | | | 2350 | | | | 2355 | | | | |

| Ser | Gln | Pro | Glu | Gly | Ser | Ile | Val | Leu | Arg | Ser | Lys | Asp | Gly | Arg |
| | 2360 | | | | | 2365 | | | | 2370 | | | | |

| Glu | Arg | Glu | Arg | Glu | Lys | Arg | Phe | Ser | Phe | Phe | Lys | Lys | Asn | Lys |
| | 2375 | | | | | 2380 | | | | 2385 | | | | |

<210> SEQ ID NO 3
<211> LENGTH: 4584
<212> TYPE: DNA
<213> ORGANISM: Rattus
<220> FEATURE:
<221> NAME/KEY: CDS
<222> LOCATION: (1)..(4581)

<400> SEQUENCE: 3

```
atg agc ata cga ttg ccc cat agt ata gac aga tca gcc agt aaa aag        48
Met Ser Ile Arg Leu Pro His Ser Ile Asp Arg Ser Ala Ser Lys Lys
1               5                   10                  15 cag tct cac ctg tcc agt ccc att gca tcc tgg tta agt agc ctg tct        96
Gln Ser His Leu Ser Ser Pro Ile Ala Ser Trp Leu Ser Ser Leu Ser
            20                  25                  30 tct ctg gga gat tct aca cct gaa cgc aca tcc cct tct cac cac cgc       144
Ser Leu Gly Asp Ser Thr Pro Glu Arg Thr Ser Pro Ser His His Arg
        35                  40                  45 cag ccc tct gac act tct gag aca aca gca ggt ctt gtt cag cgc tgt       192
Gln Pro Ser Asp Thr Ser Glu Thr Thr Ala Gly Leu Val Gln Arg Cys
    50                  55                  60 gtc atc atc caa aag gac cag cat ggc ttt ggc ttc aca gtt agt gga       240
Val Ile Ile Gln Lys Asp Gln His Gly Phe Gly Phe Thr Val Ser Gly
65                  70                  75                  80 gat cgc att gta ctg gtg cag tcc gtg cgc cct gga ggc gca gcc atg       288
Asp Arg Ile Val Leu Val Gln Ser Val Arg Pro Gly Gly Ala Ala Met
                85                  90                  95 aaa gct ggt gtg aaa gag ggt gac cgg atc atc aaa gta aac ggc acc       336
Lys Ala Gly Val Lys Glu Gly Asp Arg Ile Ile Lys Val Asn Gly Thr
            100                 105                 110 atg gtg acc aat agc tca cac ctg gag gtg gta aag ctt atc aaa tct       384
Met Val Thr Asn Ser Ser His Leu Glu Val Val Lys Leu Ile Lys Ser
        115                 120                 125 ggc gcc tat gct gcg ctt acc ctc cta ggc tct tct cct ccc tcc gtc       432
Gly Ala Tyr Ala Ala Leu Thr Leu Leu Gly Ser Ser Pro Pro Ser Val
    130                 135                 140 ggc gtc tct ggg ctc cag cag aat cca tct gtg gca gga gtg ctc aga       480
Gly Val Ser Gly Leu Gln Gln Asn Pro Ser Val Ala Gly Val Leu Arg
145                 150                 155                 160
```

```
                                                                            -continued gtt aac ccc atc att cct cca cca cct ccc ccg cca ccc ttg cca cct               528
Val Asn Pro Ile Ile Pro Pro Pro Pro Pro Pro Pro Pro Leu Pro Pro
            165                 170                 175 cca cag cac att act gga ccc aaa cct ctt cag gat cct gaa gtc caa               576
Pro Gln His Ile Thr Gly Pro Lys Pro Leu Gln Asp Pro Glu Val Gln
        180                 185                 190 aag cac gcc act caa atc ctc tgg aat atg cta aga cag gag gag gaa               624
Lys His Ala Thr Gln Ile Leu Trp Asn Met Leu Arg Gln Glu Glu Glu
    195                 200                 205 gag tta cag gac ata ctt cca ccc tgt ggt gag acc agt cag aga aca               672
Glu Leu Gln Asp Ile Leu Pro Pro Cys Gly Glu Thr Ser Gln Arg Thr
210                 215                 220 tgt gag ggc cgc ctc tct gtg gac tcc cag gag gca gac agt ggc ttg               720
Cys Glu Gly Arg Leu Ser Val Asp Ser Gln Glu Ala Asp Ser Gly Leu
225                 230                 235                 240 gat tct ggg aca gaa cgc ttt ccc tcc atc agt gag tca ttg atg aat               768
Asp Ser Gly Thr Glu Arg Phe Pro Ser Ile Ser Glu Ser Leu Met Asn
                245                 250                 255 cgg aac tca gta ttg tca gat cct gga cta gac agc cct caa acc tcc               816
Arg Asn Ser Val Leu Ser Asp Pro Gly Leu Asp Ser Pro Gln Thr Ser
            260                 265                 270 cct gta atc ctg gcc agg gtg gcc cag cac cac agg cga cag ggc tca               864
Pro Val Ile Leu Ala Arg Val Ala Gln His His Arg Arg Gln Gly Ser
        275                 280                 285 gat gca gcg ttg ctc ccg ctc aac cac cag ggt ata gat caa agc cca               912
Asp Ala Ala Leu Leu Pro Leu Asn His Gln Gly Ile Asp Gln Ser Pro
    290                 295                 300 aag cct ctg att att ggc cca gag gaa gat tat gac cca ggt tat ttc               960
Lys Pro Leu Ile Ile Gly Pro Glu Glu Asp Tyr Asp Pro Gly Tyr Phe
305                 310                 315                 320 aac aat gag agt gac atc atc ttc caa gat ctt gaa aaa ctg aag tca              1008
Asn Asn Glu Ser Asp Ile Ile Phe Gln Asp Leu Glu Lys Leu Lys Ser
                325                 330                 335 cat cca gct tac ttg gta gtt ttt cta cgt tac atc ctc tct cag gca              1056
His Pro Ala Tyr Leu Val Val Phe Leu Arg Tyr Ile Leu Ser Gln Ala
            340                 345                 350 gac cct ggc ccc ctg ctt ttt tat ttg tgt tca gaa gtt tat caa cag              1104
Asp Pro Gly Pro Leu Leu Phe Tyr Leu Cys Ser Glu Val Tyr Gln Gln
        355                 360                 365 aca aat ccc aaa gat tcc cga agt ctg ggg aaa gac atc tgg aac att              1152
Thr Asn Pro Lys Asp Ser Arg Ser Leu Gly Lys Asp Ile Trp Asn Ile
    370                 375                 380 ttc ctg gag aaa aat gcg cct ctc aga gtg aag atc cct gag atg ttg              1200
Phe Leu Glu Lys Asn Ala Pro Leu Arg Val Lys Ile Pro Glu Met Leu
385                 390                 395                 400 cag gct gaa att gac cta cgc ctg cgg aac aat gag gac cct cgc aat              1248
Gln Ala Glu Ile Asp Leu Arg Leu Arg Asn Asn Glu Asp Pro Arg Asn
                405                 410                 415 gtg ctc tgt gaa gct cag gag gca gtc atg ctg gaa atc cag gag cag              1296
Val Leu Cys Glu Ala Gln Glu Ala Val Met Leu Glu Ile Gln Glu Gln
            420                 425                 430 atc aac gac tac aga tcc aag cgt act ctg ggc ctg ggc agc ctc tat              1344
Ile Asn Asp Tyr Arg Ser Lys Arg Thr Leu Gly Leu Gly Ser Leu Tyr
        435                 440                 445 ggt gaa aat gac ctg cta ggc ctg gat ggg gac cct ctt cga gaa cgc              1392
Gly Glu Asn Asp Leu Leu Gly Leu Asp Gly Asp Pro Leu Arg Glu Arg
    450                 455                 460 caa atg gct gag aag cag ctg gct gcc ctt gga gat atc ttg tcc aaa              1440
Gln Met Ala Glu Lys Gln Leu Ala Ala Leu Gly Asp Ile Leu Ser Lys
465                 470                 475                 480
```

-continued

```
tat gag gaa gat cgg agt gcc ccc atg gac ttt gct gtt aat acc ttt      1488
Tyr Glu Glu Asp Arg Ser Ala Pro Met Asp Phe Ala Val Asn Thr Phe
                485                 490                 495 atg agc cac gct ggg atc cgt ctt cgg gag tct cga tcc tcc tgc acg      1536
Met Ser His Ala Gly Ile Arg Leu Arg Glu Ser Arg Ser Ser Cys Thr
            500                 505                 510 gca gaa aag acc cag tct gcc cct gac aag gac aag tgg ctg ccc ttc      1584
Ala Glu Lys Thr Gln Ser Ala Pro Asp Lys Asp Lys Trp Leu Pro Phe
        515                 520                 525 ttc cct aag acc aag aag cag agc agc aat tcc aag aaa gaa aag gat      1632
Phe Pro Lys Thr Lys Lys Gln Ser Ser Asn Ser Lys Lys Glu Lys Asp
    530                 535                 540 gcc ttg gag gac aag aag cga aac ccc atc ctc aga tat att ggg aag      1680
Ala Leu Glu Asp Lys Lys Arg Asn Pro Ile Leu Arg Tyr Ile Gly Lys
545                 550                 555                 560 ccc aag agc tcc tct cag agc att aag cca ggc aat gtg agg aac atc      1728
Pro Lys Ser Ser Ser Gln Ser Ile Lys Pro Gly Asn Val Arg Asn Ile
                565                 570                 575 att cag cac ttt gag aac agc cat cag tat gat gtc cca gag ccg ggg      1776
Ile Gln His Phe Glu Asn Ser His Gln Tyr Asp Val Pro Glu Pro Gly
            580                 585                 590 aca caa cga ctc tca aca gga agc ttt cct gag gac ctg ctg gag agt      1824
Thr Gln Arg Leu Ser Thr Gly Ser Phe Pro Glu Asp Leu Leu Glu Ser
        595                 600                 605 gac agt tcg cgc tca gag att cga ctg ggc cgc tct ggg agc ctc aag      1872
Asp Ser Ser Arg Ser Glu Ile Arg Leu Gly Arg Ser Gly Ser Leu Lys
    610                 615                 620 ggc cgg gaa gag atg aag cga tcc cgg aaa gca gag aac gtg ccc cgg      1920
Gly Arg Glu Glu Met Lys Arg Ser Arg Lys Ala Glu Asn Val Pro Arg
625                 630                 635                 640 cct cga agt gac gtt gac atg gat gct gct gca gag gct gcc cgc ctt      1968
Pro Arg Ser Asp Val Asp Met Asp Ala Ala Ala Glu Ala Ala Arg Leu
                645                 650                 655 cac cag tca gcc tcg tcc tct gcc tcc agc ctc tcc acc agg tct ctt      2016
His Gln Ser Ala Ser Ser Ser Ala Ser Ser Leu Ser Thr Arg Ser Leu
            660                 665                 670 gag aac cca acc cct ccc ttc acc ccc aaa atg ggc cgc agg agc att      2064
Glu Asn Pro Thr Pro Pro Phe Thr Pro Lys Met Gly Arg Arg Ser Ile
        675                 680                 685 gag tcc ccc aat ctg ggg ttc tgt aca gac gtc atc ctt ccc cac ctc      2112
Glu Ser Pro Asn Leu Gly Phe Cys Thr Asp Val Ile Leu Pro His Leu
    690                 695                 700 ctg gag gat gat ctg ggc caa ttg tct gac ctg gag cca gag cca gag      2160
Leu Glu Asp Asp Leu Gly Gln Leu Ser Asp Leu Glu Pro Glu Pro Glu
705                 710                 715                 720 gtc caa aac tgg cag cat aca gta ggc aag gat gtg gtg gcc aac ctg      2208
Val Gln Asn Trp Gln His Thr Val Gly Lys Asp Val Val Ala Asn Leu
                725                 730                 735 acc cag agg gaa att gac cgg caa gag gtc atc aat gag ctt ttt gtg      2256
Thr Gln Arg Glu Ile Asp Arg Gln Glu Val Ile Asn Glu Leu Phe Val
            740                 745                 750 aca gaa gca tct cac ctg cgc aca ctc cga gtc ctg gac ctc atc ttc      2304
Thr Glu Ala Ser His Leu Arg Thr Leu Arg Val Leu Asp Leu Ile Phe
        755                 760                 765 tac cag cgc atg aga aag gag aac cta atg cct cgg gaa gag cta gcg      2352
Tyr Gln Arg Met Arg Lys Glu Asn Leu Met Pro Arg Glu Glu Leu Ala
    770                 775                 780 cgg ctc ttc cct aac ctg cct gag ctc ata gag att cac aat tcc tgg      2400
Arg Leu Phe Pro Asn Leu Pro Glu Leu Ile Glu Ile His Asn Ser Trp
```

-continued

| | | |
|---|---|---|
| tgt gag gcc atg aag aag ctc cgg gag gag ggc ccc att atc aga gac<br>Cys Glu Ala Met Lys Lys Leu Arg Glu Glu Gly Pro Ile Ile Arg Asp<br>805                         810                     815 | 2448 |
| atc agt gac ccc atg ctg gct cgg ttt gat ggt cct gcc cga gaa gaa<br>Ile Ser Asp Pro Met Leu Ala Arg Phe Asp Gly Pro Ala Arg Glu Glu<br>820                         825                    830 | 2496 |
| ctc cag caa gta gct gca caa ttc tgt tcc tat cag tca gta gcc cta<br>Leu Gln Gln Val Ala Ala Gln Phe Cys Ser Tyr Gln Ser Val Ala Leu<br>835                         840                    845 | 2544 |
| gag cta atc agg act aag caa cgt aag gag agt cgg ttc cag ctc ttc<br>Glu Leu Ile Arg Thr Lys Gln Arg Lys Glu Ser Arg Phe Gln Leu Phe<br>850                         855                    860 | 2592 |
| atg cag gag gct gag agc cac cct cag tgc cgg cgt ctg cag ctc cga<br>Met Gln Glu Ala Glu Ser His Pro Gln Cys Arg Arg Leu Gln Leu Arg<br>865                         870                    875                    880 | 2640 |
| gac ctc atc gtc tct gaa atg caa cgg ctc acc aag tac cca ctg ctg<br>Asp Leu Ile Val Ser Glu Met Gln Arg Leu Thr Lys Tyr Pro Leu Leu<br>                       885                    890                    895 | 2688 |
| cta gag aac atc atc aag cac aca gag ggt ggc acc tct gag cat gag<br>Leu Glu Asn Ile Ile Lys His Thr Glu Gly Gly Thr Ser Glu His Glu<br>900                         905                    910 | 2736 |
| aag ctc tgc cgt gcc cgg gac cag tgc cgg gag att ctc aag ttt gtg<br>Lys Leu Cys Arg Ala Arg Asp Gln Cys Arg Glu Ile Leu Lys Phe Val<br>915                         920                    925 | 2784 |
| aat gaa gca gta aag cag aca gag aac cgc cac cgg cta gag ggg tac<br>Asn Glu Ala Val Lys Gln Thr Glu Asn Arg His Arg Leu Glu Gly Tyr<br>930                         935                    940 | 2832 |
| cag aaa cgc ctg gat gcc act gcc cta gag cgg gcc agc aac ccc ttg<br>Gln Lys Arg Leu Asp Ala Thr Ala Leu Glu Arg Ala Ser Asn Pro Leu<br>945                         950                    955                    960 | 2880 |
| gca gca gag ttc aag agc ctg gat ctt aca aca agg aag atg atc cac<br>Ala Ala Glu Phe Lys Ser Leu Asp Leu Thr Thr Arg Lys Met Ile His<br>                       965                    970                    975 | 2928 |
| gag ggg cct ctg acc tgg agg atc agc aaa gac aag acc ctg gac ctc<br>Glu Gly Pro Leu Thr Trp Arg Ile Ser Lys Asp Lys Thr Leu Asp Leu<br>980                         985                    990 | 2976 |
| cag gtg ctt ctg ctt gag gac ctg gtg gta ctg ctg cag aga caa gag<br>Gln Val Leu Leu Leu Glu Asp Leu Val Val Leu Leu Gln Arg Gln Glu<br>                       995                    1000                  1005 | 3024 |
| gag cgg ctg ctg cta aag tgc cac agc aag aca gcc gtg ggc tcc<br>Glu Arg Leu Leu Leu Lys Cys His Ser Lys Thr Ala Val Gly Ser<br>1010                    1015                  1020 | 3069 |
| tcc gac agc aag cag acg ttc agc cct gtg ctg aag ctc aat gct<br>Ser Asp Ser Lys Gln Thr Phe Ser Pro Val Leu Lys Leu Asn Ala<br>1025                    1030                  1035 | 3114 |
| gtg ctc atc cgc tcc gtg gct aca gac aag cga gcc ttc ttc atc<br>Val Leu Ile Arg Ser Val Ala Thr Asp Lys Arg Ala Phe Phe Ile<br>1040                    1045                  1050 | 3159 |
| atc tgc acc tcc gag ctg ggc cct ccc cag atc tat gag ctg gtt<br>Ile Cys Thr Ser Glu Leu Gly Pro Pro Gln Ile Tyr Glu Leu Val<br>1055                    1060                  1065 | 3204 |
| gca ttg acg tca tca gac aag aat ata tgg atg gag ctc tta gaa<br>Ala Leu Thr Ser Ser Asp Lys Asn Ile Trp Met Glu Leu Leu Glu<br>1070                    1075                  1080 | 3249 |
| gag gcc gtg cag aat gcc acc aag cac cct gga gct gcc cca atc<br>Glu Ala Val Gln Asn Ala Thr Lys His Pro Gly Ala Ala Pro Ile<br>1085                    1090                  1095 | 3294 |
| ccc atc cat ccc tca cca cca gga tcc cag gag ccg gcc tac cag | 3339 |

|     |     |
| --- | --- |
| Pro Ile His Pro Ser Pro Pro Gly Ser Gln Glu Pro Ala Tyr Gln<br>1100     1105     1110 | |
| ggc tcc acc tcc agc agg gta gaa ata aat gac tca gaa gta tat<br>Gly Ser Thr Ser Ser Arg Val Glu Ile Asn Asp Ser Glu Val Tyr<br>1115     1120     1125 | 3384 |
| cac act gaa aaa gaa ccc aag aag cta cct gaa ggc ccc ggg cct<br>His Thr Glu Lys Glu Pro Lys Lys Leu Pro Glu Gly Pro Gly Pro<br>1130     1135     1140 | 3429 |
| gag cag aga gtt caa gac aag cag ctg ata gca caa ggg gag cct<br>Glu Gln Arg Val Gln Asp Lys Gln Leu Ile Ala Gln Gly Glu Pro<br>1145     1150     1155 | 3474 |
| gtg cag gaa gag gat gaa gag gaa ttg agg acc ttg cct cga gct<br>Val Gln Glu Glu Asp Glu Glu Glu Leu Arg Thr Leu Pro Arg Ala<br>1160     1165     1170 | 3519 |
| ccc ccc tcc ctg gat gga gaa aac aga ggc atc agg aca agg gac<br>Pro Pro Ser Leu Asp Gly Glu Asn Arg Gly Ile Arg Thr Arg Asp<br>1175     1180     1185 | 3564 |
| cct gtc ctt ctg gcc ctc aca ggc cct ctc atg gag gga ctt<br>Pro Val Leu Leu Ala Leu Thr Gly Pro Leu Leu Met Glu Gly Leu<br>1190     1195     1200 | 3609 |
| gct gat gct gcc ctg gaa gat gtg gag aac ttg cgt cac ctg atc<br>Ala Asp Ala Ala Leu Glu Asp Val Glu Asn Leu Arg His Leu Ile<br>1205     1210     1215 | 3654 |
| ctg tgg agc ctg ctg cct ggt cac act gtg aag act cag gct gct<br>Leu Trp Ser Leu Leu Pro Gly His Thr Val Lys Thr Gln Ala Ala<br>1220     1225     1230 | 3699 |
| ggc gag cct gag gat gac ctc aca ccc acc cct tct gtc gtg agc<br>Gly Glu Pro Glu Asp Asp Leu Thr Pro Thr Pro Ser Val Val Ser<br>1235     1240     1245 | 3744 |
| atc acc tct cac ccc tgg gac cca ggg tcc cca ggg caa gct ccc<br>Ile Thr Ser His Pro Trp Asp Pro Gly Ser Pro Gly Gln Ala Pro<br>1250     1255     1260 | 3789 |
| acc ata agt gac agc acc cga ctt gcg agg cca gag ggc agc cag<br>Thr Ile Ser Asp Ser Thr Arg Leu Ala Arg Pro Glu Gly Ser Gln<br>1265     1270     1275 | 3834 |
| cca gag ggc gag gat gtt gct gtc agt tct ctg gca cac ctg ccg<br>Pro Glu Gly Glu Asp Val Ala Val Ser Ser Leu Ala His Leu Pro<br>1280     1285     1290 | 3879 |
| cca agg acc aga agt tct ggc gtc tgg gac tct cct gag ctg gat<br>Pro Arg Thr Arg Ser Ser Gly Val Trp Asp Ser Pro Glu Leu Asp<br>1295     1300     1305 | 3924 |
| agg aat ccg gct gca gag gct gca agc aca gaa cca gca gca agt<br>Arg Asn Pro Ala Ala Glu Ala Ala Ser Thr Glu Pro Ala Ala Ser<br>1310     1315     1320 | 3969 |
| tac aag gtt gtg aga aaa gtc tct cta ctc cct ggt ggt ggt gtc<br>Tyr Lys Val Val Arg Lys Val Ser Leu Leu Pro Gly Gly Gly Val<br>1325     1330     1335 | 4014 |
| ggt gca gcc aag gtg gcg ggc agc aat gct atc cct gac agt ggc<br>Gly Ala Ala Lys Val Ala Gly Ser Asn Ala Ile Pro Asp Ser Gly<br>1340     1345     1350 | 4059 |
| cag tca gaa tct gag cta tct gaa gtg gaa ggc gga gca cag gct<br>Gln Ser Glu Ser Glu Leu Ser Glu Val Glu Gly Gly Ala Gln Ala<br>1355     1360     1365 | 4104 |
| acg ggg aac tgt ttc tat gtc agc atg cca gca gga cct ctg gac<br>Thr Gly Asn Cys Phe Tyr Val Ser Met Pro Ala Gly Pro Leu Asp<br>1370     1375     1380 | 4149 |
| tcc agc act gag cct act ggg aca ccc cca agc ccc tca cag tgt<br>Ser Ser Thr Glu Pro Thr Gly Thr Pro Pro Ser Pro Ser Gln Cys<br>1385     1390     1395 | 4194 |

```
cac agc ctc cct gca tgg cca aca gag cct cag ccc tac agg gga         4239
His Ser Leu Pro Ala Trp Pro Thr Glu Pro Gln Pro Tyr Arg Gly
    1400                1405                1410 gtc cgt ggg ggt cag tgt tcc agc ctg gtc cgc agg gat gtg gat         4284
Val Arg Gly Gly Gln Cys Ser Ser Leu Val Arg Arg Asp Val Asp
    1415                1420                1425 gtg atc ttc cat acc atc gag cag ctc acc atc aag ctt cac aga         4329
Val Ile Phe His Thr Ile Glu Gln Leu Thr Ile Lys Leu His Arg
    1430                1435                1440 ctg aag gac atg gag ctg gcc cac aga gag ctc ctc aag tcc ctt         4374
Leu Lys Asp Met Glu Leu Ala His Arg Glu Leu Leu Lys Ser Leu
    1445                1450                1455 gga gga gag tca tcg ggt gga acc aca cct gtg ggg agt ttt cac         4419
Gly Gly Glu Ser Ser Gly Gly Thr Thr Pro Val Gly Ser Phe His
    1460                1465                1470 aca gag gca gcc aga tgg aca gac tac tcc ctc tct cct cca gcc         4464
Thr Glu Ala Ala Arg Trp Thr Asp Tyr Ser Leu Ser Pro Pro Ala
    1475                1480                1485 aag gaa gcc ctg gcc tct gat tcc caa aat ggt cag gag cag ggg         4509
Lys Glu Ala Leu Ala Ser Asp Ser Gln Asn Gly Gln Glu Gln Gly
    1490                1495                1500 tcc tgc cct gaa gaa ggc tcc gac atc gcc ctg gaa gac agt gcc         4554
Ser Cys Pro Glu Glu Gly Ser Asp Ile Ala Leu Glu Asp Ser Ala
    1505                1510                1515 act gac aca gct gtg tca cca gga cca tag                             4584
Thr Asp Thr Ala Val Ser Pro Gly Pro
    1520                1525

<210> SEQ ID NO 4
<211> LENGTH: 1527
<212> TYPE: PRT
<213> ORGANISM: Rattus

<400> SEQUENCE: 4

Met Ser Ile Arg Leu Pro His Ser Ile Asp Arg Ser Ala Ser Lys Lys
1               5                   10                  15

Gln Ser His Leu Ser Ser Pro Ile Ala Ser Trp Leu Ser Ser Leu Ser
            20                  25                  30

Ser Leu Gly Asp Ser Thr Pro Glu Arg Thr Ser Pro Ser His His Arg
        35                  40                  45

Gln Pro Ser Asp Thr Ser Glu Thr Thr Ala Gly Leu Val Gln Arg Cys
    50                  55                  60

Val Ile Ile Gln Lys Asp Gln His Gly Phe Gly Phe Thr Val Ser Gly
65                  70                  75                  80

Asp Arg Ile Val Leu Val Gln Ser Val Arg Pro Gly Gly Ala Ala Met
                85                  90                  95

Lys Ala Gly Val Lys Glu Gly Asp Arg Ile Ile Lys Val Asn Gly Thr
            100                 105                 110

Met Val Thr Asn Ser Ser His Leu Glu Val Val Lys Leu Ile Lys Ser
        115                 120                 125

Gly Ala Tyr Ala Ala Leu Thr Leu Leu Gly Ser Ser Pro Ser Val
    130                 135                 140

Gly Val Ser Gly Leu Gln Gln Asn Pro Ser Val Ala Gly Val Leu Arg
145                 150                 155                 160

Val Asn Pro Ile Ile Pro Pro Pro Pro Pro Pro Leu Pro Pro
                165                 170                 175

Pro Gln His Ile Thr Gly Pro Lys Pro Leu Gln Asp Pro Glu Val Gln
            180                 185                 190
```

```
Lys His Ala Thr Gln Ile Leu Trp Asn Met Leu Arg Gln Glu Glu
        195                 200                 205

Glu Leu Gln Asp Ile Leu Pro Pro Cys Gly Glu Thr Ser Gln Arg Thr
        210                 215                 220

Cys Glu Gly Arg Leu Ser Val Asp Ser Gln Glu Ala Asp Ser Gly Leu
225                 230                 235                 240

Asp Ser Gly Thr Glu Arg Phe Pro Ser Ile Ser Glu Ser Leu Met Asn
                245                 250                 255

Arg Asn Ser Val Leu Ser Asp Pro Gly Leu Asp Ser Pro Gln Thr Ser
        260                 265                 270

Pro Val Ile Leu Ala Arg Val Ala Gln His His Arg Arg Gln Gly Ser
        275                 280                 285

Asp Ala Ala Leu Leu Pro Leu Asn His Gln Gly Ile Asp Gln Ser Pro
        290                 295                 300

Lys Pro Leu Ile Ile Gly Pro Glu Glu Asp Tyr Asp Pro Gly Tyr Phe
305                 310                 315                 320

Asn Asn Glu Ser Asp Ile Ile Phe Gln Asp Leu Glu Lys Leu Lys Ser
                325                 330                 335

His Pro Ala Tyr Leu Val Val Phe Leu Arg Tyr Ile Leu Ser Gln Ala
                340                 345                 350

Asp Pro Gly Pro Leu Leu Phe Tyr Leu Cys Ser Glu Val Tyr Gln Gln
                355                 360                 365

Thr Asn Pro Lys Asp Ser Arg Ser Leu Gly Lys Asp Ile Trp Asn Ile
        370                 375                 380

Phe Leu Glu Lys Asn Ala Pro Leu Arg Val Lys Ile Pro Glu Met Leu
385                 390                 395                 400

Gln Ala Glu Ile Asp Leu Arg Leu Arg Asn Asn Glu Asp Pro Arg Asn
                405                 410                 415

Val Leu Cys Glu Ala Gln Glu Ala Val Met Leu Glu Ile Gln Glu Gln
                420                 425                 430

Ile Asn Asp Tyr Arg Ser Lys Arg Thr Leu Gly Leu Gly Ser Leu Tyr
        435                 440                 445

Gly Glu Asn Asp Leu Leu Gly Leu Asp Gly Asp Pro Leu Arg Glu Arg
        450                 455                 460

Gln Met Ala Glu Lys Gln Leu Ala Ala Leu Gly Asp Ile Leu Ser Lys
465                 470                 475                 480

Tyr Glu Glu Asp Arg Ser Ala Pro Met Asp Phe Ala Val Asn Thr Phe
                485                 490                 495

Met Ser His Ala Gly Ile Arg Leu Arg Glu Ser Arg Ser Ser Cys Thr
                500                 505                 510

Ala Glu Lys Thr Gln Ser Ala Pro Asp Lys Asp Lys Trp Leu Pro Phe
        515                 520                 525

Phe Pro Lys Thr Lys Gln Ser Ser Asn Ser Lys Lys Glu Lys Asp
        530                 535                 540

Ala Leu Glu Asp Lys Lys Arg Asn Pro Ile Leu Arg Tyr Ile Gly Lys
545                 550                 555                 560

Pro Lys Ser Ser Ser Gln Ser Ile Lys Pro Gly Asn Val Arg Asn Ile
                565                 570                 575

Ile Gln His Phe Glu Asn Ser His Gln Tyr Asp Val Pro Glu Pro Gly
                580                 585                 590

Thr Gln Arg Leu Ser Thr Gly Ser Phe Pro Glu Asp Leu Leu Glu Ser
        595                 600                 605
```

-continued

```
Asp Ser Ser Arg Ser Glu Ile Arg Leu Gly Arg Ser Gly Ser Leu Lys
        610                 615                 620

Gly Arg Glu Glu Met Lys Arg Ser Arg Lys Ala Glu Asn Val Pro Arg
625                 630                 635                 640

Pro Arg Ser Asp Val Asp Met Asp Ala Ala Glu Ala Ala Arg Leu
                645                 650                 655

His Gln Ser Ala Ser Ser Ala Ser Ser Leu Ser Thr Arg Ser Leu
                660                 665                 670

Glu Asn Pro Thr Pro Pro Phe Thr Pro Lys Met Gly Arg Arg Ser Ile
            675                 680                 685

Glu Ser Pro Asn Leu Gly Phe Cys Thr Asp Val Ile Leu Pro His Leu
    690                 695                 700

Leu Glu Asp Asp Leu Gly Gln Leu Ser Asp Leu Glu Pro Glu Pro Glu
705                 710                 715                 720

Val Gln Asn Trp Gln His Thr Val Gly Lys Asp Val Val Ala Asn Leu
                725                 730                 735

Thr Gln Arg Glu Ile Asp Arg Gln Glu Val Ile Asn Glu Leu Phe Val
            740                 745                 750

Thr Glu Ala Ser His Leu Arg Thr Leu Arg Val Leu Asp Leu Ile Phe
    755                 760                 765

Tyr Gln Arg Met Arg Lys Glu Asn Leu Met Pro Arg Glu Glu Leu Ala
770                 775                 780

Arg Leu Phe Pro Asn Leu Pro Glu Leu Ile Glu Ile His Asn Ser Trp
785                 790                 795                 800

Cys Glu Ala Met Lys Lys Leu Arg Glu Glu Gly Pro Ile Ile Arg Asp
                805                 810                 815

Ile Ser Asp Pro Met Leu Ala Arg Phe Asp Gly Pro Ala Arg Glu Glu
            820                 825                 830

Leu Gln Gln Val Ala Ala Gln Phe Cys Ser Tyr Gln Ser Val Ala Leu
    835                 840                 845

Glu Leu Ile Arg Thr Lys Gln Arg Lys Glu Ser Arg Phe Gln Leu Phe
850                 855                 860

Met Gln Glu Ala Glu Ser His Pro Gln Cys Arg Arg Leu Gln Leu Arg
865                 870                 875                 880

Asp Leu Ile Val Ser Glu Met Gln Arg Leu Thr Lys Tyr Pro Leu Leu
                885                 890                 895

Leu Glu Asn Ile Ile Lys His Thr Glu Gly Gly Thr Ser Glu His Glu
            900                 905                 910

Lys Leu Cys Arg Ala Arg Asp Gln Cys Arg Glu Ile Leu Lys Phe Val
    915                 920                 925

Asn Glu Ala Val Lys Gln Thr Glu Asn Arg His Arg Leu Glu Gly Tyr
930                 935                 940

Gln Lys Arg Leu Asp Ala Thr Ala Leu Glu Arg Ala Ser Asn Pro Leu
945                 950                 955                 960

Ala Ala Glu Phe Lys Ser Leu Asp Leu Thr Thr Arg Lys Met Ile His
                965                 970                 975

Glu Gly Pro Leu Thr Trp Arg Ile Ser Lys Asp Lys Thr Leu Asp Leu
            980                 985                 990

Gln Val Leu Leu Leu Glu Asp Leu Val Val Leu Leu Gln Arg Gln Glu
    995                 1000                1005

Glu Arg Leu Leu Leu Lys Cys His Ser Lys Thr Ala Val Gly Ser
    1010                1015                1020

Ser Asp Ser Lys Gln Thr Phe Ser Pro Val Leu Lys Leu Asn Ala
```

-continued

```
              1025                1030                1035

Val Leu Ile Arg Ser Val Ala Thr Asp Lys Arg Ala Phe Phe Ile
    1040                1045                1050

Ile Cys Thr Ser Glu Leu Gly Pro Pro Gln Ile Tyr Glu Leu Val
    1055                1060                1065

Ala Leu Thr Ser Ser Asp Lys Asn Ile Trp Met Glu Leu Leu Glu
    1070                1075                1080

Glu Ala Val Gln Asn Ala Thr Lys His Pro Gly Ala Ala Pro Ile
    1085                1090                1095

Pro Ile His Pro Ser Pro Pro Gly Ser Gln Glu Pro Ala Tyr Gln
    1100                1105                1110

Gly Ser Thr Ser Ser Arg Val Glu Ile Asn Asp Ser Glu Val Tyr
    1115                1120                1125

His Thr Glu Lys Glu Pro Lys Lys Leu Pro Glu Gly Pro Gly Pro
    1130                1135                1140

Glu Gln Arg Val Gln Asp Lys Gln Leu Ile Ala Gln Gly Glu Pro
    1145                1150                1155

Val Gln Glu Glu Asp Glu Glu Leu Arg Thr Leu Pro Arg Ala
    1160                1165                1170

Pro Pro Ser Leu Asp Gly Glu Asn Arg Gly Ile Arg Thr Arg Asp
    1175                1180                1185

Pro Val Leu Leu Ala Leu Thr Gly Pro Leu Leu Met Glu Gly Leu
    1190                1195                1200

Ala Asp Ala Ala Leu Glu Asp Val Glu Asn Leu Arg His Leu Ile
    1205                1210                1215

Leu Trp Ser Leu Leu Pro Gly His Thr Val Lys Thr Gln Ala Ala
    1220                1225                1230

Gly Glu Pro Glu Asp Asp Leu Thr Pro Thr Pro Ser Val Val Ser
    1235                1240                1245

Ile Thr Ser His Pro Trp Asp Pro Gly Ser Pro Gly Gln Ala Pro
    1250                1255                1260

Thr Ile Ser Asp Ser Thr Arg Leu Ala Arg Pro Glu Gly Ser Gln
    1265                1270                1275

Pro Glu Gly Glu Asp Val Ala Val Ser Ser Leu Ala His Leu Pro
    1280                1285                1290

Pro Arg Thr Arg Ser Ser Gly Val Trp Asp Ser Pro Glu Leu Asp
    1295                1300                1305

Arg Asn Pro Ala Ala Glu Ala Ala Ser Thr Glu Pro Ala Ala Ser
    1310                1315                1320

Tyr Lys Val Val Arg Lys Val Ser Leu Leu Pro Gly Gly Gly Val
    1325                1330                1335

Gly Ala Ala Lys Val Ala Gly Ser Asn Ala Ile Pro Asp Ser Gly
    1340                1345                1350

Gln Ser Glu Ser Glu Leu Ser Glu Val Glu Gly Gly Ala Gln Ala
    1355                1360                1365

Thr Gly Asn Cys Phe Tyr Val Ser Met Pro Ala Gly Pro Leu Asp
    1370                1375                1380

Ser Ser Thr Glu Pro Thr Gly Thr Pro Ser Pro Ser Gln Cys
    1385                1390                1395

His Ser Leu Pro Ala Trp Pro Thr Glu Pro Gln Pro Tyr Arg Gly
    1400                1405                1410

Val Arg Gly Gly Gln Cys Ser Ser Leu Val Arg Arg Asp Val Asp
    1415                1420                1425
```

```
Val Ile Phe His Thr Ile Glu Gln Leu Thr Ile Lys Leu His Arg
        1430                1435                1440

Leu Lys Asp Met Glu Leu Ala His Arg Glu Leu Leu Lys Ser Leu
        1445                1450                1455

Gly Gly Glu Ser Ser Gly Gly Thr Thr Pro Val Gly Ser Phe His
        1460                1465                1470

Thr Glu Ala Ala Arg Trp Thr Asp Tyr Ser Leu Ser Pro Pro Ala
        1475                1480                1485

Lys Glu Ala Leu Ala Ser Asp Ser Gln Asn Gly Gln Glu Gln Gly
        1490                1495                1500

Ser Cys Pro Glu Glu Gly Ser Asp Ile Ala Leu Glu Asp Ser Ala
        1505                1510                1515

Thr Asp Thr Ala Val Ser Pro Gly Pro
        1520                1525

<210> SEQ ID NO 5
<211> LENGTH: 567
<212> TYPE: DNA
<213> ORGANISM: Rattus
<220> FEATURE:
<221> NAME/KEY: CDS
<222> LOCATION: (1)..(564)

<400> SEQUENCE: 5 atg gac gtg aac ctt gcc ccg ctc cgt gcc tgg gat gat ttc ttc ccg      48
Met Asp Val Asn Leu Ala Pro Leu Arg Ala Trp Asp Asp Phe Phe Pro
1               5                   10                  15 ggc tct gat cgt ttc gca cgg ccg gac ttc agg gat ata tcc aaa tgg      96
Gly Ser Asp Arg Phe Ala Arg Pro Asp Phe Arg Asp Ile Ser Lys Trp
            20                  25                  30 aac aac cgt gta gtg agc aat ctg ctc tat tac cag acc aac tac ctg     144
Asn Asn Arg Val Val Ser Asn Leu Leu Tyr Tyr Gln Thr Asn Tyr Leu
        35                  40                  45 gtg gtg gct gcc atg atg att tca gtc gtt ggg ttt ctg agc ccc ttc     192
Val Val Ala Ala Met Met Ile Ser Val Val Gly Phe Leu Ser Pro Phe
    50                  55                  60 aac atg atc ctt gga gga atc att gtg gtg ctg gtg ttc acg ggg ttt     240
Asn Met Ile Leu Gly Gly Ile Ile Val Val Leu Val Phe Thr Gly Phe
65                  70                  75                  80 gtg tgg gca gca cac aat aaa gac atc ctc cgc cgg atg aag aag cag     288
Val Trp Ala Ala His Asn Lys Asp Ile Leu Arg Arg Met Lys Lys Gln
                85                  90                  95 tac cca acg gcc ttt gtc atg gtg gtc atg cta gcc agc tac ttc ctc     336
Tyr Pro Thr Ala Phe Val Met Val Val Met Leu Ala Ser Tyr Phe Leu
            100                 105                 110 ata tcc atg ttt ggg ggt gtc atg gtc ttt gtg ttt ggc atc acg ttt     384
Ile Ser Met Phe Gly Gly Val Met Val Phe Val Phe Gly Ile Thr Phe
        115                 120                 125 ccc tta ttg ttg atg ttc atc cat gca tcc ctg aga ctt cga aac ctc     432
Pro Leu Leu Leu Met Phe Ile His Ala Ser Leu Arg Leu Arg Asn Leu
    130                 135                 140 aag aac aaa ctg gaa aat aaa atg gag gga ata ggc ttg aag aaa acg     480
Lys Asn Lys Leu Glu Asn Lys Met Glu Gly Ile Gly Leu Lys Lys Thr
145                 150                 155                 160 ccg atg ggc atc atc ctg gat gcc ttg gaa cag cag gaa gac agc atc     528
Pro Met Gly Ile Ile Leu Asp Ala Leu Glu Gln Gln Glu Asp Ser Ile
                165                 170                 175 aat aaa ttt gct gac tac atc agc aaa gcc agg gag taa                 567
Asn Lys Phe Ala Asp Tyr Ile Ser Lys Ala Arg Glu
```

-continued

```
               180                 185

<210> SEQ ID NO 6
<211> LENGTH: 188
<212> TYPE: PRT
<213> ORGANISM: Rattus

<400> SEQUENCE: 6

Met Asp Val Asn Leu Ala Pro Leu Arg Ala Trp Asp Asp Phe Phe Pro
1               5                   10                  15

Gly Ser Asp Arg Phe Ala Arg Pro Asp Phe Arg Asp Ile Ser Lys Trp
            20                  25                  30

Asn Asn Arg Val Val Ser Asn Leu Leu Tyr Tyr Gln Thr Asn Tyr Leu
        35                  40                  45

Val Val Ala Ala Met Met Ile Ser Val Val Gly Phe Leu Ser Pro Phe
    50                  55                  60

Asn Met Ile Leu Gly Gly Ile Ile Val Leu Val Phe Thr Gly Phe
65                  70                  75                  80

Val Trp Ala Ala His Asn Lys Asp Ile Leu Arg Arg Met Lys Lys Gln
                85                  90                  95

Tyr Pro Thr Ala Phe Val Met Val Val Met Leu Ala Ser Tyr Phe Leu
            100                 105                 110

Ile Ser Met Phe Gly Gly Val Met Val Phe Val Phe Gly Ile Thr Phe
        115                 120                 125

Pro Leu Leu Leu Met Phe Ile His Ala Ser Leu Arg Leu Arg Asn Leu
    130                 135                 140

Lys Asn Lys Leu Glu Asn Lys Met Glu Gly Ile Gly Leu Lys Lys Thr
145                 150                 155                 160

Pro Met Gly Ile Ile Leu Asp Ala Leu Glu Gln Gln Glu Asp Ser Ile
                165                 170                 175

Asn Lys Phe Ala Asp Tyr Ile Ser Lys Ala Arg Glu
            180                 185

<210> SEQ ID NO 7
<211> LENGTH: 3111
<212> TYPE: DNA
<213> ORGANISM: Rattus norvegicus
<220> FEATURE:
<221> NAME/KEY: CDS
<222> LOCATION: (251)..(452)
<221> NAME/KEY: CDS
<222> LOCATION: (584)..(1869)
<221> NAME/KEY: exon
<222> LOCATION: (251)..(452)
<221> NAME/KEY: Intron
<222> LOCATION: (252)..(451)
<221> NAME/KEY: exon
<222> LOCATION: (584)..(1869)

<400> SEQUENCE: 7
gttggccacc atggggatgt accaagtgag actgtaggga agaaggtgg tgactcgcgt        60 gcctggctac tggctgctgc tcacctcgat gctacaagat tcctagcaag atcaaaactg      120
accattaacc tacctctaca tccccctggc gccgttccag ggccaacgcc acattccctg      180
ctgggcacgc aatggccgca ccccctcccg ctacagaagg ctcttttggt acacgcagtc      240
cgaggtcgcc atg gat cgg atg aag aag atc aaa cgg cag ctg tca atg        289
            Met Asp Arg Met Lys Lys Ile Lys Arg Gln Leu Ser Met
            1               5                   10 aca ctc cga ggg ggc cga ggc ata gac aag acc aat ggt gtc cct gag      337
Thr Leu Arg Gly Gly Arg Gly Ile Asp Lys Thr Asn Gly Val Pro Glu
```

```
                15                  20                  25
cag ata ggc cta gat gag agt ggt ggt ggt ggt ggc atg acc ctt gga      385
Gln Ile Gly Leu Asp Glu Ser Gly Gly Gly Gly Gly Met Thr Leu Gly
 30                  35                  40                  45 gaa gct ccc acc cgt gtt gcc cct ggg gaa ctt cgc tct att cgg ggc      433
Glu Ala Pro Thr Arg Val Ala Pro Gly Glu Leu Arg Ser Ile Arg Gly
                     50                  55                  60 cca ctc agc tct gca cca g gtctacctgg gtttcccagt ctgctctagg           482
Pro Leu Ser Ser Ala Pro
                 65 ggccatgtac acaaatggat acgatgaaga aatatattat attgggggaa agagagtgtt   542 cttgactcca aaggcctggc ctttccctca ctctgcacca g ag  att gtg cat gaa   597
                                               Glu Ile Val His Glu
                                                            70 gac atg aag atg gga tct gat ggg gag agt gac cag gct tca gcc aca      645
Asp Met Lys Met Gly Ser Asp Gly Glu Ser Asp Gln Ala Ser Ala Thr
             75                  80                  85 tcc tca gat gag gtg cag tct cca gtg aga gtg cgc atg cgc aac cac      693
Ser Ser Asp Glu Val Gln Ser Pro Val Arg Val Arg Met Arg Asn His
 90                  95                 100 ccc cca cgc aag atc tcc act gag gat atc aac aaa tgc ctg tca cta      741
Pro Pro Arg Lys Ile Ser Thr Glu Asp Ile Asn Lys Cys Leu Ser Leu
105                 110                 115                 120 cca gct gac ata cgg ctg cct gag ggc tac ctt gag aag ctg acc ctc      789
Pro Ala Asp Ile Arg Leu Pro Glu Gly Tyr Leu Glu Lys Leu Thr Leu
                125                 130                 135 aat agc ccc atc ggt gat aag cct ctt agc cgg cgc ctc cgg cca gtc      837
Asn Ser Pro Ile Gly Asp Lys Pro Leu Ser Arg Arg Leu Arg Pro Val
                    140                 145                 150 agc ttg tct gag att ggc ttt gga aaa ctg gag acc tac atc aaa cta      885
Ser Leu Ser Glu Ile Gly Phe Gly Lys Leu Glu Thr Tyr Ile Lys Leu
                155                 160                 165 gac aag ctg ggt gag ggt acc tat gcc act gtc tac aaa ggc aaa agc      933
Asp Lys Leu Gly Glu Gly Thr Tyr Ala Thr Val Tyr Lys Gly Lys Ser
    170                 175                 180 aag ctc aca gac aac ctt gta gca ctt aag gag atc aga ctg gaa cac      981
Lys Leu Thr Asp Asn Leu Val Ala Leu Lys Glu Ile Arg Leu Glu His
185                 190                 195                 200 gaa gaa ggg gca ccc tgc act gct atc cgg gaa gta tcc ctg ctt aag     1029
Glu Glu Gly Ala Pro Cys Thr Ala Ile Arg Glu Val Ser Leu Leu Lys
                205                 210                 215 gac ctc aag cat gcc aac atc gtc aca cta cat gac att atc cac aca     1077
Asp Leu Lys His Ala Asn Ile Val Thr Leu His Asp Ile Ile His Thr
                220                 225                 230 gag aag tcc ctc acc ctt gtc ttt gaa tac ttg gac aag gac ctg aag     1125
Glu Lys Ser Leu Thr Leu Val Phe Glu Tyr Leu Asp Lys Asp Leu Lys
            235                 240                 245 cag tac ctg gat gac tgt gga aat gtc atc aac atg cac aat gtg aaa     1173
Gln Tyr Leu Asp Asp Cys Gly Asn Val Ile Asn Met His Asn Val Lys
        250                 255                 260 ctg ttc ctg ttc cag ttg ctc cgt ggc ctg gcc tac tgc cac agg cag     1221
Leu Phe Leu Phe Gln Leu Leu Arg Gly Leu Ala Tyr Cys His Arg Gln
265                 270                 275                 280 aag gtg cta cac cga gac ctc aag ccc cag aac cta ctc atc aac gag     1269
Lys Val Leu His Arg Asp Leu Lys Pro Gln Asn Leu Leu Ile Asn Glu
                285                 290                 295 agg gga gag ctc aaa ctg gca gac ttt ggc ctg gct tac gcc aag tca     1317
Arg Gly Glu Leu Lys Leu Ala Asp Phe Gly Leu Ala Tyr Ala Lys Ser
            300                 305                 310
```

```
att cct act aaa aca tac tcc aac gaa gtg gtg aca ctg tgg tac cgg      1365
Ile Pro Thr Lys Thr Tyr Ser Asn Glu Val Val Thr Leu Trp Tyr Arg
        315                 320                 325 ccc cct gac atc tta ctt ggg tcc aca gac tac tcc ggc caa att gac      1413
Pro Pro Asp Ile Leu Leu Gly Ser Thr Asp Tyr Ser Gly Gln Ile Asp
    330                 335                 340 atg tgg ggt gtt ggc tgc atc ttt tat gag atg gcc aca ggc cgg ccc      1461
Met Trp Gly Val Gly Cys Ile Phe Tyr Glu Met Ala Thr Gly Arg Pro
345                 350                 355                 360 ctc ttc cca ggc tcc aca gtg gaa gaa cag ctg cac ttc atc ttc cgc      1509
Leu Phe Pro Gly Ser Thr Val Glu Glu Gln Leu His Phe Ile Phe Arg
            365                 370                 375 att ttg gga acc cca act gag gac aca tgg cca ggt atc ctg tcc aat      1557
Ile Leu Gly Thr Pro Thr Glu Asp Thr Trp Pro Gly Ile Leu Ser Asn
        380                 385                 390 gaa gag ttt aga aca tac aac tac ccc aag tac cga gcc gag gcc ctt      1605
Glu Glu Phe Arg Thr Tyr Asn Tyr Pro Lys Tyr Arg Ala Glu Ala Leu
    395                 400                 405 ctg agg cat gca ccc cga ctt gaa tgc gat gga gct gac ctc ctc acc      1653
Leu Arg His Ala Pro Arg Leu Glu Cys Asp Gly Ala Asp Leu Leu Thr
410                 415                 420 aag ctg ctg cag ttt gag ggt cgc aat cgg atc tct gct gag gat gcc      1701
Lys Leu Leu Gln Phe Glu Gly Arg Asn Arg Ile Ser Ala Glu Asp Ala
425                 430                 435                 440 atg aaa cat cca ttc ttt ctc agc ttg ggg gag cgg atc cac aaa ctt      1749
Met Lys His Pro Phe Phe Leu Ser Leu Gly Glu Arg Ile His Lys Leu
                445                 450                 455 cct gac act act tcc ata ttt gca cta aag gag gta cag cta caa aag      1797
Pro Asp Thr Thr Ser Ile Phe Ala Leu Lys Glu Val Gln Leu Gln Lys
            460                 465                 470 gag gcc aac att cgg tcc act tct atg cct gac tca ggc agg cca gct      1845
Glu Ala Asn Ile Arg Ser Thr Ser Met Pro Asp Ser Gly Arg Pro Ala
        475                 480                 485 ttc cgt gtg gtg gat acc gag ttc taagccaagt tttaagccac agacagacca     1899
Phe Arg Val Val Asp Thr Glu Phe
    490                 495 aggcccagc aggcagcggc tggagggatg ccacacccct cacaggacag cccccatctg     1959
caatcctccc tgcttgttgc ctgcttacct gcctgagcca cactcccctg ccaacttgtc    2019
ccctgccacc tgtccaaaca ccgaactact ggcctggcct gtcaacccaa ccactggcct    2079
gtctgctggg tgctaacaaa gctctcacca ctactttgct tgatgtgtct gtctctgtct    2139
tggtagatgc tggtggaccg aatggccgtg ccagctttcc acactaaggc taggccttcc    2199
cctcttcatc acactctctc ccaggaccac taccccatgg ccagccaggg gtttggagct    2259
agcccaggcc aggctcttaa tcgactttga ctagaaggta gtgagtgatg ccttgggtct    2319
gagcatcatt tgcctgcttc ccacctgtcc cacttgcctc tgttgtatgg gctttttttt    2379
agtttctttt attgttttt tattatttta aatgaggttc tcactttta atgcaatatc      2439 tctgtataca gactggttgg gcactactcc ctgagtgtgg cactcccaca gtattttgtg    2499
caatgaagtc ccactcccac cctttgagag gtagggaccc agaccctatt cagatcctca    2559
ccatcactag accctggaat tggctatggg aaagcatgcc tcagccactc accttcctcc    2619
cctacctagc gttcccagct ataggggac ctgagaacta ccagagagtg ggagatggac     2679
atggtggggc ctacttttc cctccttcag tcccgtagcc agggcctcct tccttctcag     2739
ggtcttcccc agcccagctc tgcctagccc tcctgccctg tcctactcgg tgctgttgag    2799
```

-continued

```
tagggctct gcctggaatc gagcagctta gtgaggagcc atatataata tgtgcacaag    2859
caggaggaca tgtgggagct tgtgcccaat tgttacaccc caatccctag gagggtcagg    2919
caggccaagg acagtctcct ggatggatgg tttgctcccc ttactccacc ttaagccttg    2979
ggacccttaa gcaggtggg agggcaaggg aggtgccct cctagtgggg tttggggga     3039 ttgggttcct gaatgcacca taatcgctgt atgaaatatt aaaaaaagt ctaaagtgaa    3099 aaaaaaaaaa aa                                                      3111
```

<210> SEQ ID NO 8
<211> LENGTH: 496
<212> TYPE: PRT
<213> ORGANISM: Rattus norvegicus

<400> SEQUENCE: 8

```
Met Asp Arg Met Lys Ile Lys Arg Gln Leu Ser Met Thr Leu Arg
1               5                   10                  15

Gly Gly Arg Gly Ile Asp Lys Thr Asn Gly Val Pro Glu Gln Ile Gly
            20                  25                  30

Leu Asp Glu Ser Gly Gly Gly Gly Met Thr Leu Gly Glu Ala Pro
        35                  40                  45

Thr Arg Val Ala Pro Gly Glu Leu Arg Ser Ile Arg Gly Pro Leu Ser
    50                  55                  60

Ser Ala Pro Glu Ile Val His Glu Asp Met Lys Met Gly Ser Asp Gly
65                  70                  75                  80

Glu Ser Asp Gln Ala Ser Ala Thr Ser Ser Asp Glu Val Gln Ser Pro
                85                  90                  95

Val Arg Val Arg Met Arg Asn His Pro Pro Arg Lys Ile Ser Thr Glu
            100                 105                 110

Asp Ile Asn Lys Cys Leu Ser Leu Pro Ala Asp Ile Arg Leu Pro Glu
        115                 120                 125

Gly Tyr Leu Glu Lys Leu Thr Leu Asn Ser Pro Ile Gly Asp Lys Pro
    130                 135                 140

Leu Ser Arg Arg Leu Arg Pro Val Ser Leu Ser Glu Ile Gly Phe Gly
145                 150                 155                 160

Lys Leu Glu Thr Tyr Ile Lys Leu Asp Lys Leu Gly Glu Gly Thr Tyr
                165                 170                 175

Ala Thr Val Tyr Lys Gly Lys Ser Lys Leu Thr Asp Asn Leu Val Ala
            180                 185                 190

Leu Lys Glu Ile Arg Leu Glu His Glu Glu Gly Ala Pro Cys Thr Ala
        195                 200                 205

Ile Arg Glu Val Ser Leu Leu Lys Asp Leu Lys His Ala Asn Ile Val
    210                 215                 220

Thr Leu His Asp Ile Ile His Thr Glu Lys Ser Leu Thr Leu Val Phe
225                 230                 235                 240

Glu Tyr Leu Asp Lys Asp Leu Lys Gln Tyr Leu Asp Asp Cys Gly Asn
                245                 250                 255

Val Ile Asn Met His Asn Val Lys Leu Phe Leu Phe Gln Leu Leu Arg
            260                 265                 270

Gly Leu Ala Tyr Cys His Arg Gln Lys Val Leu His Arg Asp Leu Lys
        275                 280                 285

Pro Gln Asn Leu Leu Ile Asn Glu Arg Gly Glu Leu Lys Leu Ala Asp
    290                 295                 300

Phe Gly Leu Ala Tyr Ala Lys Ser Ile Pro Thr Lys Thr Tyr Ser Asn
305                 310                 315                 320
```

```
Glu Val Val Thr Leu Trp Tyr Arg Pro Pro Asp Ile Leu Leu Gly Ser
                325                 330                 335
Thr Asp Tyr Ser Gly Gln Ile Asp Met Trp Val Gly Cys Ile Phe
                340                 345                 350
Tyr Glu Met Ala Thr Gly Arg Pro Leu Phe Pro Gly Ser Thr Val Glu
                355                 360                 365
Glu Gln Leu His Phe Ile Phe Arg Ile Leu Gly Thr Pro Thr Glu Asp
            370                 375                 380
Thr Trp Pro Gly Ile Leu Ser Asn Glu Glu Phe Arg Thr Tyr Asn Tyr
385                 390                 395                 400
Pro Lys Tyr Arg Ala Glu Ala Leu Leu Arg His Ala Pro Arg Leu Glu
                405                 410                 415
Cys Asp Gly Ala Asp Leu Leu Thr Lys Leu Leu Gln Phe Glu Gly Arg
                420                 425                 430
Asn Arg Ile Ser Ala Glu Asp Ala Met Lys His Pro Phe Phe Leu Ser
                435                 440                 445
Leu Gly Glu Arg Ile His Lys Leu Pro Asp Thr Thr Ser Ile Phe Ala
            450                 455                 460
Leu Lys Glu Val Gln Leu Gln Lys Glu Ala Asn Ile Arg Ser Thr Ser
465                 470                 475                 480
Met Pro Asp Ser Gly Arg Pro Ala Phe Arg Val Val Asp Thr Glu Phe
                485                 490                 495
```

<210> SEQ ID NO 9
<211> LENGTH: 8
<212> TYPE: PRT
<213> ORGANISM: ARTIFICIAL
<220> FEATURE:
<223> OTHER INFORMATION: EAAT4 peptide fragment

<400> SEQUENCE: 9

Gln Glu Ala Glu Leu Thr Leu Pro
1               5

<210> SEQ ID NO 10
<211> LENGTH: 9
<212> TYPE: PRT
<213> ORGANISM: ARTIFICIAL
<220> FEATURE:
<223> OTHER INFORMATION: EAAT4 peptide fragment

<400> SEQUENCE: 10

Gly Arg Gly Gly Asn Glu Ser Val Met
1               5

<210> SEQ ID NO 11
<211> LENGTH: 234
<212> TYPE: DNA
<213> ORGANISM: ARTIFICIAL
<220> FEATURE:
<223> OTHER INFORMATION: EAAT4COOH BAIT nucleotide

<400> SEQUENCE: 11
gaggacatca cattgatcat agctgtggat tggttccttg atcgacttcg tacgatgacc      60
aatgtacttg gggactcaat tggagcagct gtcattgagc atttgtccca acgggagctg     120
gagctgcaag aggctgagct gactctaccc agcctgggga aaccctataa gtcactcatg     180
gcacaagcca aggggcatc aagggtcgg ggaggtaatg agagtgtcat gtga             234

```
<210> SEQ ID NO 12
<211> LENGTH: 77
<212> TYPE: PRT
<213> ORGANISM: ARTIFICIAL
<220> FEATURE:
<223> OTHER INFORMATION: EAAT4COOH BAIT peptide

<400> SEQUENCE: 12

Glu Asp Ile Thr Leu Ile Ile Ala Val Asp Trp Phe Leu Asp Arg Leu
1               5                   10                  15

Arg Thr Met Thr Asn Val Leu Gly Asp Ser Ile Gly Ala Ala Val Ile
            20                  25                  30

Glu His Leu Ser Gln Arg Glu Leu Glu Leu Gln Glu Ala Glu Leu Thr
        35                  40                  45

Leu Pro Ser Leu Gly Lys Pro Tyr Lys Ser Leu Met Ala Gln Ala Lys
    50                  55                  60

Gly Ala Ser Arg Gly Arg Gly Gly Asn Glu Ser Val Met
65                  70                  75

<210> SEQ ID NO 13
<211> LENGTH: 86
<212> TYPE: PRT
<213> ORGANISM: ARTIFICIAL
<220> FEATURE:
<223> OTHER INFORMATION: EEAC C-TERM BAIT RAT

<400> SEQUENCE: 13

Val Asp Trp Leu Leu Asp Arg Phe Arg Thr Met Val Asn Val Leu Gly
1               5                   10                  15

Asp Ala Phe Gly Thr Gly Ile Val Glu Lys Leu Ser Lys Lys Glu Leu
            20                  25                  30

Glu Gln Val Asp Val Ser Ser Glu Val Asn Ile Val Asn Pro Phe Ala
        35                  40                  45

Leu Glu Pro Thr Ile Leu Asp Asn Glu Asp Ser Asp Thr Lys Lys Ser
    50                  55                  60

Tyr Val Asn Gly Gly Phe Ser Val Asp Lys Ser Asp Thr Ile Ser Phe
65                  70                  75                  80

Thr Gln Thr Ser Gln Phe
                85

<210> SEQ ID NO 14
<211> LENGTH: 14
<212> TYPE: PRT
<213> ORGANISM: ARTIFICIAL
<220> FEATURE:
<223> OTHER INFORMATION: synthetic peptides representing EEAT4
      C-Terminal Ab epitopes

<400> SEQUENCE: 14

Glu Lys Gly Ala Ser Arg Gly Arg Gly Gly Asn Glu Ser Ala
1               5                   10

<210> SEQ ID NO 15
<211> LENGTH: 16
<212> TYPE: PRT
<213> ORGANISM: ARTIFICIAL
<220> FEATURE:
<223> OTHER INFORMATION: synthetic peptides representing EEAT4
      N-Terminal Ab epitopes

<400> SEQUENCE: 15

Lys Asn Ser Leu Phe Leu Arg Glu Ser Gly Ala Gly Gly Gly Cys Leu
1               5                   10                  15
```

<210> SEQ ID NO 16
<211> LENGTH: 16
<212> TYPE: PRT
<213> ORGANISM: ARTIFICIAL
<220> FEATURE:
<223> OTHER INFORMATION: synthetic peptides representing rat GTRAP4-41
      Ab epitopes

<400> SEQUENCE: 16

Lys Arg Gly Pro Ala Pro Ser Pro Met Pro Gln Ser Arg Ser Ser Glu
1               5                   10                  15

<210> SEQ ID NO 17
<211> LENGTH: 16
<212> TYPE: PRT
<213> ORGANISM: ARTIFICIAL
<220> FEATURE:
<223> OTHER INFORMATION: synthetic peptides representing rat GTRAP4-48
      Ab epitopes

<400> SEQUENCE: 17

Lys Thr Pro Glu Arg Thr Ser Pro Ser His His Arg Gln Pro Ser Asp
1               5                   10                  15

<210> SEQ ID NO 18
<211> LENGTH: 16
<212> TYPE: PRT
<213> ORGANISM: ARTIFICIAL
<220> FEATURE:
<223> OTHER INFORMATION: synthetic peptides representing GTRAP3-18 Ab
      epitopes

<400> SEQUENCE: 18

Lys Phe Phe Pro Gly Ser Asp Arg Phe Ala Arg Pro Asp Phe Arg Asp
1               5                   10                  15

<210> SEQ ID NO 19
<211> LENGTH: 17
<212> TYPE: DNA
<213> ORGANISM: ARTIFICIAL
<220> FEATURE:
<223> OTHER INFORMATION: GTRAP3-18 sense oligonucleotide

<400> SEQUENCE: 19
gtgaaccttg cccgctc                                                          17

<210> SEQ ID NO 20
<211> LENGTH: 18
<212> TYPE: DNA
<213> ORGANISM: ARTIFICIAL
<220> FEATURE:
<223> OTHER INFORMATION: GTRAP3-18 anti-sense oligonucleotide

<400> SEQUENCE: 20
gagcggggca aggttcac                                                         18

<210> SEQ ID NO 21
<211> LENGTH: 6222
<212> TYPE: DNA
<213> ORGANISM: Rattus norvegicus
<220> FEATURE:
<221> NAME/KEY: CDS
<222> LOCATION: (487)..(1869)

<400> SEQUENCE: 21
gttggccacc atggggatgt accaagtgag actgtaggga aagaaggtgg tgactcgcgt            60

-continued

```
gcctggctac tggctgctgc tcacctcgat gctacaagat tcctagcaag atcaaaactg      120
accattaacc tacctctaca tccccctggc gccgttccag ggccaacgcc acattccctg      180
ctgggcacgc aatggccgca ccccctcccg ctacagaagg ctcttttggt acacgcagtc      240
cgaggtcgcc atggatcgga tgaagaagat caaacggcag ctgtcaatga cactccgagg      300
gggccgaggc atagacaaga ccaatggtgt ccctgagcag ataggcctag atgagagtgg      360
tggtggtggt ggcatgaccc ttggagaagc tcccacccgt gttgcccctg ggaacttcg       420 ctctattcgg ggcccactca gctctgcacc aggtctacct gggtttccca gtctgctcta     480 ggggcc atg tac aca aat gga tac gat gaa gaa ata tat tat att ggg        528
       Met Tyr Thr Asn Gly Tyr Asp Glu Glu Ile Tyr Tyr Ile Gly
         1               5                  10 gga aag aga gtg ttc ttg act cca aag gcc tgg cct ttc cct cac tct        576
Gly Lys Arg Val Phe Leu Thr Pro Lys Ala Trp Pro Phe Pro His Ser
 15          20                  25                  30 gca cca gag att gtg cat gaa gac atg aag atg gga tct gat ggg gag        624
Ala Pro Glu Ile Val His Glu Asp Met Lys Met Gly Ser Asp Gly Glu
             35                  40                  45 agt gac cag gct tca gcc aca tcc tca gat gag gtg cag tct cca gtg        672
Ser Asp Gln Ala Ser Ala Thr Ser Ser Asp Glu Val Gln Ser Pro Val
     50                  55                  60 aga gtg cgc atg cgc aac cac ccc cca cgc aag atc tcc act gag gat        720
Arg Val Arg Met Arg Asn His Pro Pro Arg Lys Ile Ser Thr Glu Asp
 65                  70                  75 atc aac aaa tgc ctg tca cta cca gct gac ata cgg ctg cct gag ggc        768
Ile Asn Lys Cys Leu Ser Leu Pro Ala Asp Ile Arg Leu Pro Glu Gly
         80                  85                  90 tac ctt gag aag ctg acc ctc aat agc ccc atc ggt gat aag cct ctt        816
Tyr Leu Glu Lys Leu Thr Leu Asn Ser Pro Ile Gly Asp Lys Pro Leu
 95                  100                 105                 110 agc cgg cgc ctc cgg cca gtc agc ttg tct gag att ggc ttt gga aaa        864
Ser Arg Arg Leu Arg Pro Val Ser Leu Ser Glu Ile Gly Phe Gly Lys
             115                 120                 125 ctg gag acc tac atc aaa cta gac aag ctg ggt gag ggt acc tat gcc        912
Leu Glu Thr Tyr Ile Lys Leu Asp Lys Leu Gly Glu Gly Thr Tyr Ala
     130                 135                 140 act gtc tac aaa ggc aaa agc aag ctc aca gac aac ctt gta gca ctt        960
Thr Val Tyr Lys Gly Lys Ser Lys Leu Thr Asp Asn Leu Val Ala Leu
         145                 150                 155 aag gag atc aga ctg gaa cac gaa gaa ggg gca ccc tgc act gct atc       1008
Lys Glu Ile Arg Leu Glu His Glu Glu Gly Ala Pro Cys Thr Ala Ile
 160                 165                 170 cgg gaa gta tcc ctg ctt aag gac ctc aag cat gcc aac atc gtc aca       1056
Arg Glu Val Ser Leu Leu Lys Asp Leu Lys His Ala Asn Ile Val Thr
175                 180                 185                 190 cta cat gac att atc cac aca gag aag tcc ctc acc ctt gtc ttt gaa       1104
Leu His Asp Ile Ile His Thr Glu Lys Ser Leu Thr Leu Val Phe Glu
             195                 200                 205 tac ttg gac aag gac ctg aag cag tac ctg gat gac tgt gga aat gtc       1152
Tyr Leu Asp Lys Asp Leu Lys Gln Tyr Leu Asp Asp Cys Gly Asn Val
     210                 215                 220 atc aac atg cac aat gtg aaa ctg ttc ctg ttc cag ttg ctc cgt ggc       1200
Ile Asn Met His Asn Val Lys Leu Phe Leu Phe Gln Leu Leu Arg Gly
         225                 230                 235 ctg gcc tac tgc cac agg cag aag gtg cta cac cga gac ctc aag ccc       1248
Leu Ala Tyr Cys His Arg Gln Lys Val Leu His Arg Asp Leu Lys Pro
 240                 245                 250
```

```
cag aac cta ctc atc aac gag agg gga gag ctc aaa ctg gca gac ttt   1296
Gln Asn Leu Leu Ile Asn Glu Arg Gly Glu Leu Lys Leu Ala Asp Phe
255                 260                 265                 270 ggc ctg gct tac gcc aag tca att cct act aaa aca tac tcc aac gaa   1344
Gly Leu Ala Tyr Ala Lys Ser Ile Pro Thr Lys Thr Tyr Ser Asn Glu
                275                 280                 285 gtg gtg aca ctg tgg tac cgg ccc cct gac atc tta ctt ggg tcc aca   1392
Val Val Thr Leu Trp Tyr Arg Pro Pro Asp Ile Leu Leu Gly Ser Thr
            290                 295                 300 gac tac tcc ggc caa att gac atg tgg ggt gtt ggc tgc atc ttt tat   1440
Asp Tyr Ser Gly Gln Ile Asp Met Trp Gly Val Gly Cys Ile Phe Tyr
        305                 310                 315 gag atg gcc aca ggc cgg ccc ctc ttc cca ggc tcc aca gtg gaa gaa   1488
Glu Met Ala Thr Gly Arg Pro Leu Phe Pro Gly Ser Thr Val Glu Glu
320                 325                 330 cag ctg cac ttc atc ttc cgc att ttg gga acc cca act gag gac aca   1536
Gln Leu His Phe Ile Phe Arg Ile Leu Gly Thr Pro Thr Glu Asp Thr
335                 340                 345                 350 tgg cca ggt atc ctg tcc aat gaa gag ttt aga aca tac aac tac ccc   1584
Trp Pro Gly Ile Leu Ser Asn Glu Glu Phe Arg Thr Tyr Asn Tyr Pro
                355                 360                 365 aag tac cga gcc gag gcc ctt ctg agg cat gca ccc cga ctt gaa tgc   1632
Lys Tyr Arg Ala Glu Ala Leu Leu Arg His Ala Pro Arg Leu Glu Cys
            370                 375                 380 gat gga gct gac ctc ctc acc aag ctg ctg cag ttt gag ggt cgc aat   1680
Asp Gly Ala Asp Leu Leu Thr Lys Leu Leu Gln Phe Glu Gly Arg Asn
        385                 390                 395 cgg atc tct gct gag gat gcc atg aaa cat cca ttc ttt ctc agc ttg   1728
Arg Ile Ser Ala Glu Asp Ala Met Lys His Pro Phe Phe Leu Ser Leu
400                 405                 410 ggg gag cgg atc cac aaa ctt cct gac act act tcc ata ttt gca cta   1776
Gly Glu Arg Ile His Lys Leu Pro Asp Thr Thr Ser Ile Phe Ala Leu
415                 420                 425                 430 aag gag gta cag cta caa aag gag gcc aac att cgg tcc act tct atg   1824
Lys Glu Val Gln Leu Gln Lys Glu Ala Asn Ile Arg Ser Thr Ser Met
                435                 440                 445 cct gac tca ggc agg cca gct ttc cgt gtg gtg gat acc gag ttc       1869
Pro Asp Ser Gly Arg Pro Ala Phe Arg Val Val Asp Thr Glu Phe
            450                 455                 460 taagccaagt tttaagccac agacagacca aggccccagc aggcagcggc tggagggatg   1929
ccacacccct cacaggacag cccccatctg caatcctccc tgcttgttgc ctgcttacct   1989
gcctgagcca cactcccctg ccaacttgtc ccctgccacc tgtccaaaca ccgaactact   2049
ggcctggcct gtcaacccaa ccactggcct gtctgctggg tgctaacaaa gctctcacca   2109
ctactttgct tgatgtgtct gtctctgtct tggtagatgc tggtggaccg aatggccgtg   2169
ccagctttcc acactaaggc taggccttcc cctcttcatc acactctctc ccaggaccac   2229 tacccccatgg ccagccaggg gttttggagct agcccaggcc aggctcttaa tcgactttga   2289
ctagaaggta gtgagtgatg ccttgggtct gagcatcatt tgcctgcttc ccacctgtcc   2349
cacttgcctc tgttgtatgg gctttttttt agtttctttt attgtttttt tattatttta   2409
aatgaggttc tcacttttta atgcaatatc tctgtataca gactggttgg gcactactcc   2469
ctgagtgtgg cactcccaca gtattttgtg caatgaagtc ccactcccac cctttgagag   2529
gtagggaccc agaccctatt cagatcctca ccatcactag accctggaat tggctatggg   2589
aaagcatgcc tcagccactc accttcctcc cctaccctagc gttcccagct ataggggac    2649 ctgagaacta ccagagagtg ggagatggac atggtggggc ctacttttc cctccttcag    2709
```

-continued

```
tcccgtagcc agggcctcct tccttctcag ggtcttcccc agcccagctc tgcctagccc    2769
tcctgccctg tcctactcgg tgctgttgag tagggctct gcctggaatc gagcagctta     2829
gtgaggagcc atatataata tgtgcacaag caggaggaca tgtgggagct tgtgcccaat    2889
tgttcacccc caatccctag gagggtcagg caggccaagg acagtctcct ggatggatgg    2949
tttgctcccc ttactccacc ttaagccttg ggacccttaa gcagggtggg agggcaaggg    3009
agggtgccct cctagtgggg tttgggggga ttgggttcct gaatgcacca taatcgctgt    3069
atgaaatatt aaaaaaagt ctaaagtgaa aaaaaaaaa aagttggcca ccatgggat      3129
gtaccaagtg agactgtagg gaaagaaggt ggtgactcgc gtgcctggct actggctgct    3189
gctcacctcg atgctacaag attcctagca agatcaaaac tgaccattaa cctacctcta    3249
catcccctg gcgccgttcc agggccaacg ccacattccc tgctgggcac gcaatggccg     3309
cacccctcc cgctacagaa ggctcttttg gtacacgcag tccgaggtcg ccatggatcg     3369
gatgaagaag atcaaacggc agctgtcaat gacactccga gggggccgag gcatagacaa    3429
gaccaatggt gtccctgagc agataggcct agatgagagt ggtggtggtg gtggcatgac    3489
ccttggagaa gctcccaccc gtgttgcccc tggggaactt cgctctattc ggggcccact    3549
cagctctgca ccaggtctac ctgggttttcc cagtctgctc tagggccat gtacacaaat     3609
ggatacgatg aagaaatata ttatattggg ggaaagagag tgttcttgac tccaaaggcc    3669
tggcctttcc ctcactctgc accagagatt gtgcatgaag acatgaagat gggatctgat    3729
ggggagagtg accaggcttc agccacatcc tcagatgagg tgcagtctcc agtgagagtg    3789
cgcatgcgca accaccccc acgcaagatc tccactgagg atatcaacaa atgcctgtca    3849
ctaccagctg acatacggct gcctgagggc taccttgaga agctgaccct caatagcccc    3909
atcggtgata gcctcttag ccggcgcctc cggccagtca gcttgtctga gattggcttt     3969
ggaaaactgg agacctacat caaactagac aagctgggtg agggtaccta tgccactgtc    4029
tacaaaggca aaagcaagct cacagacaac cttgtagcac ttaaggagat cagactggaa    4089
cacgaagaag gggcaccctg cactgctatc cgggaagtat ccctgcttaa ggacctcaag    4149
catgccaaca tcgtcacact acatgacatt atccacacag agaagtccct cacccttgtc    4209
tttgaatact tggacaagga cctgaagcag tacctggatg actgtggaaa tgtcatcaac    4269
atgcacaatg tgaaactgtt cctgttccag ttgctccgtg gcctggccta ctgccacagg    4329
cagaaggtgc tacaccgaga cctcaagccc cagaacctac tcatcaacga gaggggagag    4389
ctcaaactgg cagactttgg cctggcttac gccaagtcaa ttcctactaa aacatactcc    4449
aacgaagtgg tgacactgtg gtaccggccc cctgacatct tacttgggtc cacagactac    4509
tccggccaaa ttgacatgtg gggtgttggc tgcatctttt atgagatggc cacaggccgg    4569
cccctcttcc caggctccac agtggaagaa cagctgcact tcatcttccg cattttggga    4629
accccaactg aggacacatg gccaggtatc ctgtccaatg aagagtttag aacatacaac    4689
taccccaagt accgagccga ggcccttctg aggcatgcac cccgacttga atgcgatgga    4749
gctgacctcc tcaccaagct gctgcagttt gagggtcgca atcggatctc tgctgaggat    4809
gccatgaaac atccattctt tctcagcttg ggggagcgga tccacaaact tcctgacact    4869
acttccatat ttgcactaaa ggaggtacag ctacaaaagg aggccaacat tcggtccact    4929
tctatgcctg actcaggcag gccagctttc cgtgtggtgg ataccgagtt ctaagccaag    4989
ttttaagcca cagacagacc aaggccccag caggcagcgg ctggagggat gccacacccc    5049
```

-continued

```
tcacaggaca gcccccatct gcaatcctcc ctgcttgttg cctgcttacc tgcctgagcc    5109
acactcccct gccaacttgt ccctgccac  ctgtccaaac accgaactac tggcctggcc    5169
tgtcaaccca accactggcc tgtctgctgg gtgctaacaa agctctcacc actactttgc    5229
ttgatgtgtc tgtctctgtc ttggtagatg ctggtggacc gaatggccgt gccagctttc    5289
cacactaagg ctaggccttc ccctcttcat cacactctct cccaggacca ctaccccatg    5349
gccagccagg ggtttggagc tagcccaggc caggctctta atcgactttg actagaaggt    5409
agtgagtgat gccttgggtc tgagcatcat ttgcctgctt cccacctgtc ccacttgcct    5469
ctgttgtatg ggcttttttt tagtttcttt tattgttttt ttattatttt aaatgaggtt    5529 ctcactttt  aatgcaatat ctctgtatac agactggttg ggcactactc cctgagtgtg    5589
gcactcccac agtattttgt gcaatgaagt cccactccca cccttgaga  ggtagggacc    5649 cagaccctat tcagatcctc accatcacta gaccctggaa ttggctatgg gaaagcatgc    5709
ctcagccact caccttcctc ccctacctag cgttcccagc tataggggga cctgagaact    5769
accagagagt gggagatgga catggtgggg cctactttt  ccctccttca gtcccgtagc    5829
cagggcctcc ttccttctca gggtcttccc cagcccagct ctgcctagcc ctcctgccct    5889
gtcctactcg gtgctgttga gtaggggctc tgcctggaat cgagcagctt agtgaggagc    5949
catatataat atgtgcacaa gcaggaggac atgtgggagc ttgtgcccaa ttgttacacc    6009
ccaatcccta ggagggtcag gcaggccaag gacagtctcc tggatggatg gtttgctccc    6069
cttactccac cttaagcctt gggaccctta agcagggtgg gagggcaagg gagggtgccc    6129
tcctagtggg gtttgggggg attgggttcc tgaatgcacc ataatcgctg tatgaaatat    6189
taaaaaaaag tctaaagtga aaaaaaaaaa aaa                                  6222
```

<210> SEQ ID NO 22
<211> LENGTH: 461
<212> TYPE: PRT
<213> ORGANISM: Rattus norvegicus

<400> SEQUENCE: 22

```
Met Tyr Thr Asn Gly Tyr Asp Glu Glu Ile Tyr Tyr Ile Gly Gly Lys
1               5                   10                  15

Arg Val Phe Leu Thr Pro Lys Ala Trp Pro Phe Pro His Ser Ala Pro
                20                  25                  30

Glu Ile Val His Glu Asp Met Lys Met Gly Ser Asp Gly Glu Ser Asp
            35                  40                  45

Gln Ala Ser Ala Thr Ser Ser Asp Glu Val Gln Ser Pro Val Arg Val
        50                  55                  60

Arg Met Arg Asn His Pro Pro Arg Lys Ile Ser Thr Glu Asp Ile Asn
65                  70                  75                  80

Lys Cys Leu Ser Leu Pro Ala Asp Ile Arg Leu Pro Glu Gly Tyr Leu
                85                  90                  95

Glu Lys Leu Thr Leu Asn Ser Pro Ile Gly Asp Lys Pro Leu Ser Arg
                100                 105                 110

Arg Leu Arg Pro Val Ser Leu Ser Glu Ile Gly Phe Gly Lys Leu Glu
            115                 120                 125

Thr Tyr Ile Lys Leu Asp Lys Leu Gly Glu Gly Thr Tyr Ala Thr Val
        130                 135                 140

Tyr Lys Gly Lys Ser Lys Leu Thr Asp Asn Leu Val Ala Leu Lys Glu
145                 150                 155                 160

Ile Arg Leu Glu His Glu Glu Gly Ala Pro Cys Thr Ala Ile Arg Glu
```

-continued

```
                165                 170                 175
Val Ser Leu Leu Lys Asp Leu Lys His Ala Asn Ile Val Thr Leu His
            180                 185                 190
Asp Ile Ile His Thr Glu Lys Ser Leu Thr Leu Val Phe Glu Tyr Leu
            195                 200                 205
Asp Lys Asp Leu Lys Gln Tyr Leu Asp Asp Cys Gly Asn Val Ile Asn
            210                 215                 220
Met His Asn Val Lys Leu Phe Leu Phe Gln Leu Leu Arg Gly Leu Ala
225                 230                 235                 240
Tyr Cys His Arg Gln Lys Val Leu His Arg Asp Leu Lys Pro Gln Asn
            245                 250                 255
Leu Leu Ile Asn Glu Arg Gly Glu Leu Lys Leu Ala Asp Phe Gly Leu
            260                 265                 270
Ala Tyr Ala Lys Ser Ile Pro Thr Lys Thr Tyr Ser Asn Glu Val Val
            275                 280                 285
Thr Leu Trp Tyr Arg Pro Pro Asp Ile Leu Leu Gly Ser Thr Asp Tyr
            290                 295                 300
Ser Gly Gln Ile Asp Met Trp Gly Val Gly Cys Ile Phe Tyr Glu Met
305                 310                 315                 320
Ala Thr Gly Arg Pro Leu Phe Pro Gly Ser Thr Val Glu Glu Gln Leu
            325                 330                 335
His Phe Ile Phe Arg Ile Leu Gly Thr Pro Thr Glu Asp Thr Trp Pro
            340                 345                 350
Gly Ile Leu Ser Asn Glu Glu Phe Arg Thr Tyr Asn Tyr Pro Lys Tyr
            355                 360                 365
Arg Ala Glu Ala Leu Leu Arg His Ala Pro Arg Leu Glu Cys Asp Gly
370                 375                 380
Ala Asp Leu Leu Thr Lys Leu Leu Gln Phe Glu Gly Arg Asn Arg Ile
385                 390                 395                 400
Ser Ala Glu Asp Ala Met Lys His Pro Phe Phe Leu Ser Leu Gly Glu
            405                 410                 415
Arg Ile His Lys Leu Pro Asp Thr Thr Ser Ile Phe Ala Leu Lys Glu
            420                 425                 430
Val Gln Leu Gln Lys Glu Ala Asn Ile Arg Ser Thr Ser Met Pro Asp
            435                 440                 445
Ser Gly Arg Pro Ala Phe Arg Val Val Asp Thr Glu Phe
450                 455                 460
```